US010500245B2

(12) United States Patent
Maugard et al.

(10) Patent No.: US 10,500,245 B2
(45) Date of Patent: Dec. 10, 2019

(54) COMPOSITIONS FOR PREVENTING AND/OR TREATING PATHOLOGICAL CONDITIONS ASSOCIATED WITH ALPHA-GLUCOSIDASE

(71) Applicants: UNIVERSITE DE LA ROCHELLE, La Rochelle (FR); UNIVERSITE BLAISE PASCAL-CLERMONT II, Clermont-Ferrand (FR)

(72) Inventors: Thierry Maugard, La Jarne (FR); Stephanie Bordenave-Juchereau, Le Thou (FR); Jean-Marie Piot, Perigny (FR); Yesmine Ben-Henda, La Rochelle (FR); Pascal Sirvent, Ceyrat (FR); Sebastien Peltier, Fouras (FR)

(73) Assignees: UNIVERSITE DE LA ROCHELLE, La Rochelle (FR); UNIVERSITE CLERMONT AUVERGNE, Clermont-Ferrand (FR)

( * ) Notice: Subject to any disclaimer, the term of this patent is extended or adjusted under 35 U.S.C. 154(b) by 0 days.

(21) Appl. No.: 15/119,032

(22) PCT Filed: Feb. 18, 2015

(86) PCT No.: PCT/FR2015/050397
§ 371 (c)(1),
(2) Date: Aug. 15, 2016

(87) PCT Pub. No.: WO2015/124867
PCT Pub. Date: Aug. 27, 2015

(65) Prior Publication Data
US 2018/0104303 A1    Apr. 19, 2018

(30) Foreign Application Priority Data

Feb. 18, 2014   (FR) ...................... 14 51280

(51) Int. Cl.
| | |
|---|---|
| *A61K 38/06* | (2006.01) |
| *A23L 33/18* | (2016.01) |
| *A23L 33/00* | (2016.01) |
| *A61P 3/10* | (2006.01) |
| *A61K 38/00* | (2006.01) |
| *A61K 38/01* | (2006.01) |
| *A61K 45/06* | (2006.01) |
| *A61K 38/05* | (2006.01) |

(52) U.S. Cl.
CPC .............. *A61K 38/06* (2013.01); *A23L 33/18* (2016.08); *A23L 33/30* (2016.08); *A61K 38/005* (2013.01); *A61K 38/01* (2013.01); *A61K 38/05* (2013.01); *A61K 45/06* (2013.01); *A61P 3/10* (2018.01); *A23V 2002/00* (2013.01)

(58) Field of Classification Search
CPC ........ A61K 38/05; A61K 38/06; A61K 38/01; A61K 38/005; A61K 45/06; A61P 3/10; A23L 33/30; A23L 33/18; A23V 2002/00
See application file for complete search history.

(56) References Cited

U.S. PATENT DOCUMENTS

| | | | |
|---|---|---|---|
| 5,643,874 A | 7/1997 | Bremer et al. | |
| 6,803,357 B1 * | 10/2004 | Bachovchin | A61K 31/00 514/119 |
| 2004/0229934 A1 | 11/2004 | Yusuf | |
| 2006/0035864 A1 | 2/2006 | Friesen | |
| 2008/0274987 A1 * | 11/2008 | Ahmad | C07H 15/00 514/27 |
| 2009/0075904 A1 * | 3/2009 | Boots | A61K 38/018 514/1.1 |
| 2011/0269795 A1 | 11/2011 | Becq et al. | |

FOREIGN PATENT DOCUMENTS

| | | |
|---|---|---|
| EP | 0 638 317 A1 | 2/1995 |
| EP | 1 661 909 A1 | 5/2006 |
| EP | 1 690 869 A1 | 8/2006 |
| WO | 2005/046672 A2 | 5/2005 |
| WO | 2006/005757 A2 | 1/2006 |
| WO | 2006/068480 A2 | 6/2006 |
| WO | 2006/084560 A1 | 8/2006 |
| WO | 2006/096769 A2 | 9/2006 |
| WO | 2012/085266 A2 | 6/2012 |

OTHER PUBLICATIONS

Maruyama et al, Studies on the Active Site and Antihypertensive Activity of Angiotensin I-Converting Enzyme Inhibitors Derived from Casein, Agric. Biol. Chem., 1987, 51, pp. 1581-1586.*
Amann et al, ACE Inhibitors Improve Diabetic Nephropathy Through Suppression of Renal MCP-1, Diabetes Care, 2003, 26, pp. 2421-2425.*
Chua, Angiotensin-converting enzyme inhibitors: An ACE in the hole for everyone? BC Medical Journal, 2011, 53, pp. 220-223.*
Diabetes Mellitus-Merck Manual, from http://www.merckmanuals.com/professional/print/endocrine_and_metabolic_disorders/diab . . . , pp. 1-22, accessed Apr. 2, 2013.*
De Mattia et al, Circulating Catecholamines and Metabolic Effects of Captopril in NIDDM Patients, Diabetes Care, 1996, 19, pp. 226-230.*
Shapiro et al, Inhibition of Angiotensin Converting Enzyme: Mechanism and Substrate Dependence, Biochemistry, 1984, 23, pp. 5225-5233.*
Evary, State of the Art and Clinical Perspective of Apha Glucosidase Inhibitors: A Review, IJPRS, 2016, 5, pp. 145-150.*

(Continued)

*Primary Examiner* — Karlheinz R. Skowronek
*Assistant Examiner* — Li N Komatsu
(74) *Attorney, Agent, or Firm* — Young & Thompson

(57) ABSTRACT

A composition including at least one XAP peptide, in which X represents the empty set or a valine, for use in the prevention and/or treatment of pathologies associated with alpha-glucosidase. Also, the use of a hydrolysate of at least one protein, the protein including or constituted by at least 0.05% to <5% or of at least 5% of XAP units, in which X represents the empty set or a valine, for use in the prevention and/or treatment of pathologies associated with alpha-glucosidase.

5 Claims, 9 Drawing Sheets

Figure 1:
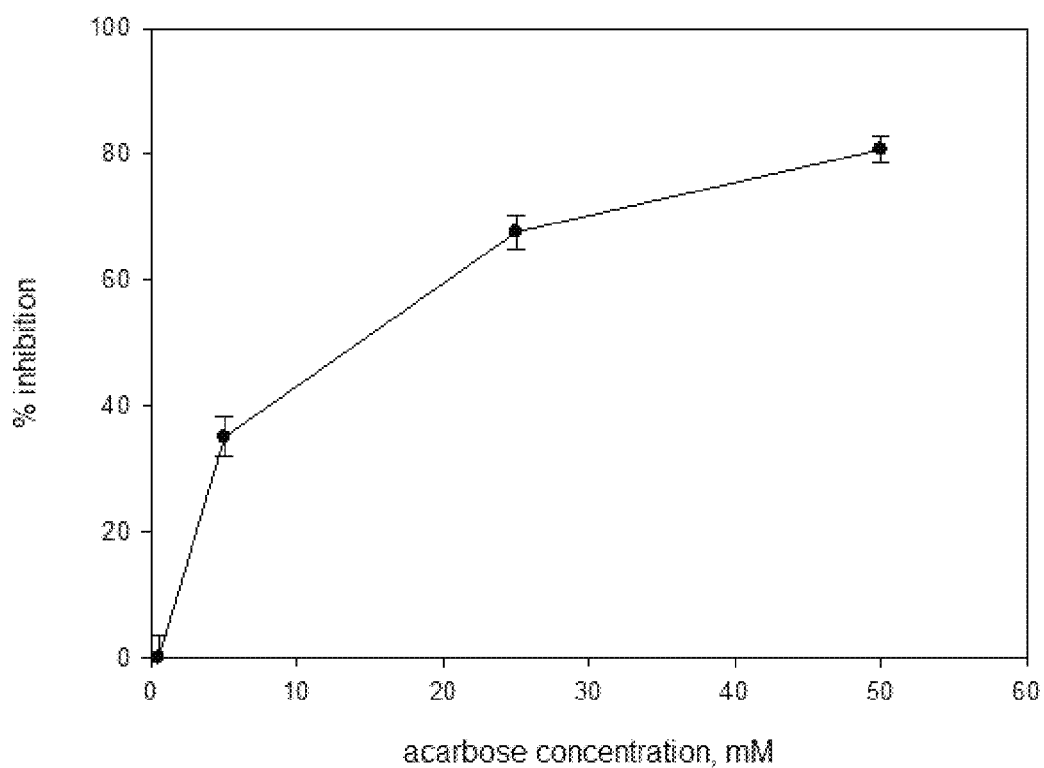

Specification includes a Sequence Listing.

(56) References Cited

OTHER PUBLICATIONS

Ben Henda et al, Measuring Angiotensin-I Converting Enzyme Inhibitory Activity by Micro Plate Assays: Comparison Using Marine Cryptides and Tentative Threshold Determinations with Captopril and Losartan, J. Agric. Food Chem., 2013, 61, pp. 10685-10690.*

International Preliminary Report on Patentability PCT/FR2015/050397 dated Sep. 1, 2016.

Chu Kwan et al.: "Angiotensin II in type 2 diabetes mellitus.", Current Protein & Peptide Science Feb. 2009, vol. 10, No. 1, Feb. 2009 (Feb. 2009), pp. 75-84, XP009178203, ISSN: 1389-2037.

International Search Report, dated May 12, 2015, from corresponding PCT application.

FR Search Report, dated May 30, 2014, from corresponding FR application.

* cited by examiner

COMPOSITIONS FOR PREVENTING AND/OR TREATING PATHOLOGICAL CONDITIONS ASSOCIATED WITH ALPHA-GLUCOSIDASE

The instant application is a 371 of PCT/FR2015/050397 filed on Feb. 18, 2015, which claims foreign priority to French Application FR 14/51280 filed on Feb. 18, 2014.

The present invention relates to the use of compositions for the prevention and/or treatment of pathologies associated with alpha-glucosidase.

The present invention relates to the use of compositions for the prevention and/or treatment of type 2 diabetes.

Type 2 diabetes is the commonest form of diabetes. It is a chronic, progressive metabolic pathology, characterized by chronic hyperglycaemia, i.e. an abnormally high concentration of sugar in the blood (glycaemia). Although insulin resistance and insufficient secretion of insulin in response to a given metabolic state constitute the main cause, other factors may contribute to a state of chronic hyperglycaemia, for example a sedentary lifestyle.

Type 2 diabetes constitutes a major public health problem. In the majority of industrialized countries, the prevalence of known cases of diabetes is between 6 and 7% for people in the age range from 45 to 64 years, gradually increasing to more than 20% for people of 80 years and over.

Various classes of products for the treatment and/or prevention of type 2 diabetes are already known. Enzyme inhibitors have in particular been proposed, especially inhibitors of dipeptidyl peptidase IV or of alpha-glucosidase.

Although dipeptidyl peptidase IV and alpha-glucosidase both have the effect of lowering postprandial glycaemia, these two enzymes have different mechanisms of action that are unrelated. Thus, it is not obvious that an inhibitor of alpha-glucosidase inhibits dipeptidyl peptidase IV, and vice versa.

In fact, dipeptidyl peptidase IV (DPP-IV) is a multifunctional transmembrane glycoprotein that is expressed in most tissues, especially those involved in the degradation of peptides (in particular the kidney, alimentary canal, liver and biliary tract, uterus, prostate and the skin). This glycoprotein has three biological properties: it binds adenosine deaminase (ADA), it contributes to the binding of cells to the extracellular matrix, and it is a peptidase.

As a peptidase, dipeptidyl peptidase IV in particular cleaves hormones such as glucagon-like peptide 1 (GLP-1). GLP-1 is an incretin, i.e. an intestinal hormone secreted by the L cells of the ileum in response to a meal. One of its roles is to promote insulin secretion in order to lower postprandial glycaemia. However, GLP-1 is quickly degraded in the plasma by DPP-IV and thus has a short half-life of approximately 1 or 2 minutes.

The inhibition of dipeptidyl peptidase IV makes it possible to increase the circulation half-life of GLP-1, which is thus active for a longer time, which is reflected in prolonged secretion of insulin in order to lower postprandial glycaemia.

Inhibitors of dipeptidyl peptidase IV have thus been proposed, in particular peptides derived from protein hydrolysates as described in international application WO 2006/068480.

The alpha-glucosidase enzyme can be subdivided into four enzymes involved in glucose metabolism (maltase, saccharase, glucoamylase and isomaltase). All these enzymes are located on the surface of the villi of the small intestine and transform complex polysaccharides into absorbable monosaccharides (glucose).

In fact, absorbed polysaccharides are degraded by salivary and pancreatic amylase to disaccharides (sucrose, lactose or maltose) and then to absorbable monosaccharides by alpha-glucosidases or beta-glucosidases (lactase and invertase).

Maltase and isomaltase catalyse the hydrolysis of maltose and dextrins to glucose.

Saccharase splits sucrose into a fructose molecule and a glucose molecule.

Glucoamylase catalyses the hydrolysis of maltotriose and dextrins to glucose.

Lactase promotes the dissociation of lactose to glucose and galactose.

Invertase is a beta-fructofuranosidase; it belongs to the saccharase family and therefore hydrolyses sucrose.

Among the known alpha-glucosidase inhibitors, there are bioactive peptides such as the peptides Ile-Ile-Ser-Ile-Gly (SEQ ID NO: 18); Ile-Ile-Ser-Ile-Gly-Arg (SEQ ID NO: 19); Val-Ph -Ile-Lys-Ala-Ala (SEQ ID NO: 20); Val-Phe-Ile-Lys-Ala-Ala-Ala (SEQ ID NO: 21) and Val-Phe-Ile-Lys-Ala (SEQ ID NO: 22), as described in Japanese application JPH 1029 2000, or chemical compounds such as acarbose (marketed in France by Bayer AG under the name Glucor and Glucobay® in Europe) and miglitol (marketed under the name Diastabol® in Europe).

Acarbose and miglitol both inhibit alpha-glucosidase competitively and reversibly, and in particular saccharase (their $IC_{50}$ with respect to saccharase is 0.5 µM and 0.19 µM respectively). They inhibit the last stage of the digestion of sugars which, as they cannot be absorbed, continue their journey through the intestine and undergo bacterial fermentation in the colon to volatile fatty acids or are eliminated in the faeces. They therefore make it possible to slow down the digestion of sugars and decrease their absorption, which leads to a decrease in postprandial glycaemia in the short term and that of the glycated haemoglobin in the medium term.

These two compounds nevertheless have side-effects, due to stagnation and fermentation of undigested sugars in the intestine, in particular digestive disorders such as abdominal pains, bloating, flatulence, and diarrhea. Moreover, these compounds on average only allow glycated haemoglobin to be lowered by 0.5 to 1%, which is reflected in an average decrease in plasma glycaemia of 0.17 to 0.35 g/L.

In comparison, inhibitors of alpha-amylase (an enzyme responsible for the hydrolysis of long-chain carbohydrates) used as a nutraceutical allow a larger decrease in glycated haemoglobin. Thus, consumption of MealShape®, a cinnamon extract marketed by the DIALPHA company, at a dose of 500 mg, taken twice, before eating a meal rich in carbohydrates (white bread), induces a decrease in postprandial glycaemia of approximately 20% (measurement of the area under the curve over a period of 1 hour, in comparison with a placebo in healthy volunteers; DIALPHA data made public but not yet published in a peer-reviewed scientific journal). MealShape® was the subject-matter of international application WO 2012/085266 A2. In the same way, ingesting 3000 mg of StarchLite® in the form of powder, under similar conditions, seems to induce a decrease in the glycaemic index of certain foodstuffs of approximately 30% (Udani J K et al. Nutr J 2009, 8: 52). StarchLite® is an extract of white bean (*Phaseolus vulgaris*) marketed by the company Ingredia Nutritional.

MealShape® and StarchLite® are nevertheless only used in the nutraceutical or food area, and not in the therapeutic area. Moreover, it is described in the literature that the consumption of large doses of cinnamon or of cinnamon extracts may prove toxic (the median lethal dose ($LD_{50}$) is 0.196 g/kg in mice).

Moreover, the enzyme inhibitor bioactive peptides are also used in an area other than the prevention and/or treatment of type 2 diabetes. In this connection, the VAP (a valine-alanine-proline tripeptide) and AP (an alanine-proline dipeptide) peptides are in particular known for their inhibitory activity on the angiotensin converting enzyme (see for example the articles Maruyama et al., *Agric. Biol. Chem.*, 51 (6), 1581-1586, 1987 and Cheung et al., *J. Biol. Chem.* 1980, 255: 401-407 or international application WO 2006/084560).

There is thus a real need to provide hypoglycaemic molecules for the treatment and/or prevention of type 2 diabetes that have fewer side-effects than the existing treatments.

There is also a real need to provide hypoglycaemic molecules for the treatment and/or prevention of type 2 diabetes that are more effective than those of the prior art.

There is also a real need to provide hypoglycaemic molecules that can be used in the treatment and/or prevention of type 2 diabetes, in the therapeutic area, but also in the food and/or nutraceutical area.

The present invention thus aims to provide hypoglycaemic molecules that are more effective and more natural than those of the prior art.

The present invention also aims to provide hypoglycaemic molecules that can be used both in the therapeutic area, and in the food and/or nutraceutical area.

Thus, the present invention relates to compositions comprising peptides that are inhibitors of alpha-glucosidase for the prevention and/or treatment of pathologies associated with alpha-glucosidase, in particular type 2 diabetes.

The present invention also relates to a pharmaceutical composition comprising such peptides.

The present invention also relates to the use of such peptides for the preparation of a nutraceutical composition or a food supplement.

The present invention also relates to a nutraceutical composition or a food composition comprising such peptides.

Finally, the present invention relates to compositions comprising hydrolysates of at least one protein having, in its amino acid sequence, amino acid units that are inhibitors of alpha-glucosidase for the prevention and/or treatment of pathologies associated with alpha-glucosidase, in particular type 2 diabetes.

The present invention also relates to a pharmaceutical composition comprising such hydrolysates.

The present invention also relates to the use of such hydrolysates for the preparation of a nutraceutical composition or a food supplement.

The present invention also relates to a nutraceutical composition or a food composition comprising such hydrolysates.

In a first aspect, the present invention thus relates to a composition comprising or consisting of at least one XAP peptide, in which X represents the empty set or a valine, for use in the prevention and/or treatment of pathologies associated with alpha-glucosidase.

The expression "X represents the empty set or a valine" means that XAP may be a VAP tripeptide or a AP dipeptide.

The VAP tripeptide is constituted by a sequence of the three amino acids, in the following order: valine then alanine and then proline. The amino acids are joined together by peptide bonds. The proline is in C-terminal position.

The AP dipeptide is constituted by a sequence of the two amino acids, in the following order: alanine and then proline. The amino acids are joined together by peptide bonds. The proline is in C-terminal position.

Said VAP and AP peptides can act on postprandial glycaemia, and may in particular make it possible to lower it.

In said VAP and AP peptides, the amino acids valine, alanine and proline may be either laevorotatory, or dextrorotatory.

The successive amino acid residues of the peptides according to the invention preferably all constituted by their laevorotatory isomers. One or more of the amino acid residues of the aforesaid peptides may nevertheless also be in the dextrorotatory form. This results in products that are less biodegradable.

In a particular and preferred aspect of the invention, the peptide used is the AP peptide.

In a particular aspect of the invention, the alpha-glucosidase is a maltase or a saccharase.

The inventors have thus found, surprisingly, that the VAP or AP peptides have a very strong activity as an inhibitor of alpha-glucosidase, in particular maltase, and in particular have a median inhibitory concentration of alpha-glucosidase, in particular maltase, of approximately 600 times and approximately 900 times lower relative to that of the two reference inhibitors of alpha-glucosidase, namely acarbose and miglitol.

In a particular aspect of the invention, the present invention thus relates to a composition comprising or constituted by at least one XAP peptide, in which X represents the empty set or a valine, for use as alpha-glucosidase inhibitor.

In fact, the invention also relates to the XAP peptides, in which X represents the empty set or a valine, for use as alpha-glucosidase inhibitor.

The inhibitory activity of the VAP and AP peptides can, for example, be measured in vitro according to the following protocol:

Solubilizing the peptides to be tested or the control molecule (for example, in the present case the VAP or AP peptides and acarbose or miglitol) in deionized water containing 10% of DMSO (dimethyl sulphoxide);

Mixing 20 µL of alpha-glucosidase in 0.1 mol/L sodium phosphate buffer (pH 6.8) to a final concentration of 0.2 U/mL with 8 µL of the sample of peptide or of acarbose or of miglitol at different concentrations (0.01 to 50 mmol/L). Acarbose or miglitol, commercial synthetic inhibitors, regarded as a reference inhibitor of alpha-glucosidase, are used here as positive control;

Incubating at 37° C. for 20 minutes;

Adding 20 µL of the substrate p-NPG (p-nitrophenyl glucopyranoside) at 2.5 mM (prepared in the same buffer as mentioned above) to the mixture in order to start the reaction;

Incubating for 30 minutes at 37° C.;

Stopping the reaction by adding 80 µL of a solution of sodium carbonate ($Na_2CO_3$) at 0.3M;

Measuring the quantity of product formed (p-nitrophenyl (p-NP) of yellow colour) by spectrophotometry (absorbance at 410 nm, VersaMax™, Microplate Reader). Preferably, the assay is performed in a 96-well microplate in triplicate.

Calculating the percentage inhibition from the following equation:

$$\% \text{ inhibition} = \left[1 - \frac{(OD \text{ sample assay} - OD \text{ assay blank})}{(OD \text{ control assay} - OD \text{ control blank})}\right] * 100$$

in which:
OD sample assay corresponds to the optical density obtained for the mixture "sample+enzyme+substrate"
OD assay blank corresponds to the optical density obtained for the mixture "sample+buffer"
OD control assay corresponds to the optical density obtained for the mixture "buffer+enzyme+substrate"
OD control blank corresponds to the optical density obtained for the buffer.

The inhibitory activity of the VAP and AP peptides can, for example, be measured in vivo according to the following protocol:

The inhibitory activity of the AP and VAP peptides and the effect of the AP and VAP peptides on the glycaemic response, can be measured in an oral test of tolerance to sucrose and to maltose in vivo in db/db mice.

Mice aged 4 weeks are used and each mouse is its own control.

Five oral tests of tolerance to sucrose and/or maltose (4 g/kg) are carried out on each mouse with a minimum interval of 72 h. The order is determined so as to cancel a potentially confounding effect of a change in the body composition of the mice during the 3 study weeks.

The 5 tests are as follows:
A control test (comprising 0.9% saline solution);
A test with the AP peptide (at a concentration of 500 mg/kg);
A test with the VAP peptide (at a concentration of 500 mg/kg);
A test with the AP peptide (at a concentration of 500 mg/kg) and with the VAP peptide (at a concentration of 500 mg/kg);
A test with acarbose (at a concentration of 10 mg/kg). This last-mentioned test with acarbose is optional for determining the inhibitory activity of the AP and VAP peptides.

Sucrose or maltose and the test products are diluted in 0.9% saline solution, and then administered directly by the gastric route.

Five minutes after administration by the gastric route, a first blood sample is taken from the tail in order to determine the glycaemia (t=0); then 6 other samples are taken after 15, 30, 45, 60, 90 and 120 minutes.

The main criterion for evaluation is measurement of the area under the glycaemic curve over a period of 2 hours following administration of sucrose or maltose (AUC, area under the curve, 0-120 minutes, in g*min/L).

The alpha-glucosidase that may be used for the purposes of the aforementioned protocols may for example be the recombinant alpha-glucosidase from *Saccharomyces cerevisiae*, which is a maltase.

Any other protocol judged by a person skilled in the art to be equivalent or more appropriate may be used.

In one aspect of the invention, the pathologies associated with alpha-glucosidase are for example type 2 diabetes, mucoviscidosis (see international application WO2005046672 A2), hepatitis C (see international application WO2006096769), and adiposis (see patent EP0638317 B1).

In a more particular aspect of the invention, the pathology associated with alpha-glucosidase is type 2 diabetes.

In a particular aspect of the invention, said peptides are used in patients who have or are at risk for prediabetes, in particular a type 2 prediabetes. Said patients do not necessarily have cardiovascular diseases, in particular arterial hypertension, coronary disease or chronic heart failure. In fact, patients who have prediabetes, in particular type 2 prediabetes, do not necessarily have arterial hypertension (AH).

Prediabetes corresponds to a state in which the glycaemia levels are higher than normal without being high enough for a diagnosis of diabetes. Prediabetes can form part of a medical concept called metabolic syndrome. The definition of metabolic syndrome involves various data including obesity of the abdominal type, abnormality of the lipid parameters, arterial hypertension, etc. Metabolic syndrome is itself a risk factor for the development of cardiovascular pathologies. Not everyone with prediabetes will necessarily develop diabetes. But when metabolic syndrome is present, this risk is multiplied by 10 relative to a healthy subject.

Prediabetes is defined by a fasting glycaemia greater than or equal to 1 g/l (in particular between 1 g/l and 1.26 g/l, regardless of the normal laboratory values), or glucose intolerance.

Diabetes is diagnosed when the fasting glycaemia is greater than or equal to 1.26 g/l, for 2 successive samples or when glycaemia is greater than or equal to 2 g/l at any time of day.

In another particular aspect of the invention, said composition for the use thereof in the prevention and/or treatment of pathologies associated with alpha-glucosidase comprises at least one VAP peptide and/or at least one AP peptide. This means that the composition according to the present invention comprises at least one VAP peptide or at least one AP peptide, or that said composition comprises at least one VAP peptide and at least one AP peptide.

In another particular aspect of the invention, said composition for the use thereof in the prevention and/or treatment of pathologies associated with alpha-glucosidase comprises or is constituted by at least one XAP peptide, in which X represents the empty set or a valine, in combination with at least one peptide of type APX'.

The expression "peptide of type APX'" corresponds to a peptide in which A is an alanine amino acid, P is a proline amino acid, and X' corresponds to an amino acid or a group of amino acids selected from the 20 amino acids universally distributed in living beings (alanine; arginine; asparagine; aspartate or aspartic acid; cysteine; glutamate or glutamic acid; glutamine; glycine; histidine; isoleucine; leucine; lysine; methionine; phenylalanine; proline; serine; threonine; tryptophan; tyrosine; valine). The amino acids are joined together by peptide bonds.

In a particular aspect of the invention, the peptide of type APX' is selected from APFPE (SEQ ID NO: 1) or APFPEVF (SEQ ID NO: 2).

Thus, in a particular aspect of the invention, said composition for the use thereof in the prevention and/or treatment of pathologies associated with alpha-glucosidase comprises or is constituted by at least one XAP peptide, in which X represents the empty set or a valine, in association with at least one APFPE and/or APFPEVF peptide.

Thus, in a particular aspect of the invention, the composition for the use thereof in the prevention and/or treatment of pathologies associated with alpha-glucosidase comprises or is constituted by at least the following combinations of peptides:

AP+APFPE (SEQ ID NO: 1), or
AP+APFPEVF (SEQ ID NO: 2), or
VAP+APFPE (SEQ ID NO: 1), or
VAP+APFPEVF (SEQ ID NO: 2), or
AP+APFPE (SEQ ID NO: 1)+APFPEVF (SEQ ID NO: 2), or
VAP+APFPE (SEQ ID NO: 1)+APFPEVF (SEQ ID NO: 2), or
AP+VAP+APFPE (SEQ ID NO: 1)+APFPEVF (SEQ ID NO: 2), or
AP+VAP+APFPE (SEQ ID NO: 1), or
AP+VAP+APFPEVF (SEQ ID NO: 2).

In another aspect of the invention, said composition for the use thereof in the prevention and/or treatment of pathologies associated with alpha-glucosidase comprises or is constituted by approximately 0.06 mg/kg to approximately 40.0 mg/kg of XAP peptide.

In another aspect of the invention, said composition for the use thereof in the prevention and/or treatment of pathologies associated with alpha-glucosidase comprises or is constituted by approximately 0.06 mg/kg to approximately 30.0 mg/kg of XAP peptide or from approximately >30.0 mg/kg to 40.0 mg/kg of XAP peptide, and in an advantageous embodiment approximately 0.06 mg/kg to approximately 0.099 mg/kg.

The doses were established assuming an adult patient weighing 75 kg.

The expression "approximately 0.06 mg/kg to approximately 30.0 mg/kg" is to be understood as possibly covering values just below 0.06 mg/kg, for example 0.059 mg/kg, or just above 30.0 mg/kg, for example 30.1 mg/kg, in particular for a patient with a weight other than 75 kg.

The expression "approximately >30.0 mg/kg to approximately 40.0 mg/kg" is to be understood as possibly covering values just above 40.0 mg/kg, for example 40.1 mg/kg, in particular for a patient with a weight other than 75 kg.

The expression "approximately >30.0 mg/kg" means values strictly above 30.0 mg/kg.

The expression "approximately 0.06 mg/kg to approximately 30.0 mg/kg" thus means that the composition according to the present invention may comprise all the values from 0.06 mg/kg to 30.0 mg/kg, in particular from 0.06 mg/kg to 0.08 mg/kg; from 0.06 mg/kg to 0.09 mg/kg; from 0.06 mg/kg to 0.1 mg/kg; from 0.06 mg/kg to 0.5 mg/kg; from 0.06 mg/kg to 1.0 mg/kg; from 0.06 mg/kg to 2.0 mg/kg; from 0.06 mg/kg to 5.0 mg/kg; from 0.06 mg/kg to 10.0 mg/kg; from 0.06 mg/kg to 15.0 mg/kg; from 0.06 mg/kg to 20.0 mg/kg; from 0.06 mg/kg to 25.0 mg/kg; from 0.06 mg/kg to 30.0 mg/kg; from 0.2 mg/kg to 0.4 mg/kg; from 0.2 to 0.5 mg/kg; from 0.6 mg/kg to 0.9 mg/kg; from 0.6 mg/kg to 1 mg/kg; from 2 mg/kg to 3 mg/kg or 4 mg/kg or 5 mg/kg or 6 mg/kg or 7 mg/kg or 8 mg/kg or 9 mg/kg or 10 mg/kg or 11 mg/kg or 12 mg/kg or 13 mg/kg or 14 mg/kg or 15 mg/kg or 16 mg/kg or 17 mg/kg or 18 mg/kg or 19 mg/kg or 20 mg/kg or 21 mg/kg or 22 mg/kg or 23 mg/kg or 24 mg/kg or 25 mg/kg or 26 mg/kg or 27 mg/kg or 28 mg/kg or 29 mg/kg or 30 mg/kg.

The expression "approximately >30.0 mg/kg to approximately 40.0 mg/kg" thus means that the composition according to the present invention may comprise all the values above 30.0 mg/kg to approximately 40.0 mg/kg, in particular 31 mg/kg, 32 mg/kg, 33 mg/kg, 34 mg/kg, 35 mg/kg, 36 mg/kg, 37 mg/kg, 38 mg/kg, 39 mg/kg and 40 mg/kg.

In one aspect, the invention thus relates to a composition for the use thereof in the prevention and/or treatment of pathologies associated with alpha-glucosidase, comprising or consisting of approximately 0.06 mg/kg to approximately 30.0 mg/kg of VAP peptide or from approximately >30.0 mg/kg to 40.0 mg/kg of VAP peptide, and/or comprising or consisting of approximately 0.06 mg/kg to approximately 30.0 mg/kg of AP peptide or from approximately >30.0 mg/kg to 40.0 mg/kg of AP peptide, and/or comprising or consisting of approximately 0.06 mg/kg to approximately 30.0 mg/kg of VAP and AP peptides or from approximately >30.0 mg/kg to 40.0 mg/kg of VAP and AP peptides.

In a particular aspect, said composition for the use thereof in the prevention and/or treatment of pathologies associated with alpha-glucosidase also comprises or is constituted by approximately 0.06 mg/kg to approximately 0.099 mg/kg of VAP peptide, and/or said composition for the use thereof in the prevention and/or treatment of pathologies associated with alpha-glucosidase also comprises or is constituted by approximately 0.06 mg/kg to approximately 0.099 mg/kg of AP peptide, and/or said composition for the use thereof in the prevention and/or treatment of pathologies associated with alpha-glucosidase also comprises or is constituted by approximately 0.06 mg/kg to approximately 0.099 mg/kg of VAP and AP peptides.

In another particular aspect, said composition for the use thereof in the prevention and/or treatment of pathologies associated with alpha-glucosidase also comprises or is constituted by approximately 0.1 mg/kg to approximately 30.0 mg/kg of VAP peptide or from approximately >30.0 mg/kg to 40.0 mg/kg of VAP peptide, and/or said composition for the use thereof in the prevention and/or treatment of pathologies associated with alpha-glucosidase also comprises or is constituted by approximately 0.1 mg/kg to approximately 30.0 mg/kg of AP peptide or from approximately >30.0 mg/kg to 40.0 mg/kg of AP peptide, and/or said composition for the use thereof in the prevention and/or treatment of pathologies associated with alpha-glucosidase also comprises or is constituted by approximately 0.1 mg/kg to approximately 30.0 mg/kg of VAP and AP peptides or from approximately >30.0 mg/kg to 40.0 mg/kg of VAP and AP peptides.

In a particular aspect of the invention, said composition for the use thereof in the prevention and/or treatment of pathologies associated with alpha-glucosidase thus comprises or is constituted by approximately 0.06 mg/kg to approximately 30.0 mg/kg of VAP peptide, in particular approximately 0.06 mg/kg to approximately 0.099 mg/kg or in particular approximately 0.1 mg/kg to approximately 30.0 mg/kg, or said composition for the use thereof in the prevention and/or treatment of pathologies associated with alpha-glucosidase comprises or is constituted by approximately >30.0 mg/kg to 40.0 mg/kg of VAP peptide.

In another particular aspect of the invention, said composition for the use thereof in the prevention and/or treatment of pathologies associated with alpha-glucosidase thus comprises or is constituted by approximately 0.06 mg/kg to approximately 30.0 mg/kg of AP peptide, in particular approximately 0.06 mg/kg to approximately 0.099 mg/kg or in particular approximately 0.1 mg/kg to approximately 30.0 mg/kg, or said composition for the use thereof in the prevention and/or treatment of pathologies associated with alpha-glucosidase comprises or is constituted by approximately >30.0 mg/kg to 40.0 mg/kg of AP peptide.

In another particular aspect of the invention, said composition for the use thereof in the prevention and/or treatment of pathologies associated with alpha-glucosidase thus comprises or is constituted by approximately 0.06 mg/kg to approximately 30.0 mg/kg of VAP and AP peptides, in particular approximately 0.06 mg/kg to approximately 0.099 mg/kg or in particular approximately 0.1 mg/kg to approximately 30.0 mg/kg, or said composition for the use thereof in the prevention and/or treatment of pathologies associated with alpha-glucosidase comprises or is constituted by approximately >30.0 mg/kg to 40.0 mg/kg of VAP and AP peptides.

In yet another aspect of the invention, said composition for the use thereof in the prevention and/or treatment of pathologies associated with alpha-glucosidase also comprises or is constituted by approximately 0.06 mg/kg to approximately 30.0 mg/kg of VAP peptide, in particular approximately 0.06 mg/kg to approximately 0.099 mg/kg or in particular approximately 0.1 mg/kg to approximately 30.0 mg/kg, and said composition for the use thereof in the prevention and/or treatment of pathologies associated with alpha-glucosidase also comprises or is constituted by approximately 0.06 mg/kg to approximately 30.0 mg/kg of AP peptide, in particular approximately 0.06 mg/kg to approximately 0.099 mg/kg or approximately 0.1 mg/kg to approximately 30.0 mg/kg.

In yet another aspect of the invention, said composition for the use thereof in the prevention and/or treatment of pathologies associated with alpha-glucosidase also comprises or is constituted by approximately >30.0 mg/kg to 40.0 mg/kg of VAP peptide, and said composition for the use thereof in the prevention and/or treatment of pathologies associated with alpha-glucosidase also comprises or is constituted by approximately >30.0 mg/kg to 40.0 mg/kg of AP peptide.

In another particular aspect, said composition for the use thereof in the prevention and/or treatment of pathologies associated with alpha-glucosidase also comprises or is constituted by 13.3 mg/kg of XAP peptide, in particular of AP peptide.

In another aspect, said composition for the use thereof in the prevention and/or treatment of pathologies associated with alpha-glucosidase is in unit form and comprises or is constituted by a quantity of XAP peptide from approximately 5 mg to 3000 mg.

In another aspect, said composition for the use thereof in the prevention and/or treatment of pathologies associated with alpha-glucosidase is in unit form and comprises or is constituted by a quantity of XAP peptide from approximately 5 mg to 2250 mg or from approximately >2250 mg to 3000 mg.

In another aspect, said composition for the use thereof in the prevention and/or treatment of pathologies associated with alpha-glucosidase comprises or is constituted by a quantity of VAP peptide from approximately 5 mg to approximately 2250 mg or from approximately >2250 mg to 3000 mg, and/or comprises or is constituted by a quantity of AP peptide from approximately 5 mg to approximately 2250 mg or from approximately >2250 mg to 3000 mg, and/or comprises or is constituted by a quantity of VAP and AP peptides from approximately 5 mg to approximately 2250 mg or from approximately >2250 mg to 3000 mg.

The expression "from approximately 5 mg to approximately 2250 mg" means that the doses may be just below 5 mg, for example 4.9 mg, and just above 2250 mg, for example 2250.1 mg. This expression thus means that all the values from 5 mg to 2250 mg are comprised, for example from 5 mg to 10 mg; from 10 mg to 15 mg; from 15 mg to 20 mg; from 20 mg to 25 mg; from 25 mg to 30 mg; from 30 mg to 35 mg; from 35 mg to 40 mg; from 45 mg to 50 mg; from 50 mg to 55 mg; from 55 mg to 60 mg; from 60 mg to 65 mg; from 65 mg to 70 mg; from 70 mg to 75 mg; from 75 mg to 80 mg; from 80 mg to 85 mg; from 85 mg to 90 mg or from 95 mg to 100 mg, but also from 5 mg to 100 mg; to 150 mg; to 200 mg; to 250 mg; to 300 mg; to 350 mg; to 400 mg; to 450 mg; to 500 mg; to 550 mg; to 600 mg; to 650 mg; to 700 mg; to 750 mg; to 800 mg; to 850 mg; to 900 mg; to 950 mg; to 1000 mg; to 1050 mg; to 1100 mg; to 1150 mg; to 1200 mg; to 1250 mg; to 1300 mg; to 1350 mg; to 1400 mg; to 1450 mg; to 1500 mg; to 1550 mg; to 1600 mg; to 1650 mg; to 1700 mg; to 1750 mg; to 1800 mg; to 1850 mg; to 1900 mg; to 1950 mg; to 2000 mg; to 2050 mg; to 2100 mg; to 2150 mg; to 2200 mg.

In a particular aspect, said composition for the use thereof in the prevention and/or treatment of pathologies associated with alpha-glucosidase comprises or is constituted by a quantity of 1000 mg of XAP peptide, in particular of AP peptide.

The expression "from approximately >2250 mg to 3000 mg" means that the doses may be just above 3000 mg, for example 3000.1 mg. This expression thus means that all the values from >2250 mg to 3000 mg are comprised, in particular 2260 mg; 2270 mg; 2280 mg and 2290 mg.

The expression "from approximately >2250 mg" means values strictly above 2250 mg.

In another aspect, said composition for the use thereof in the prevention and/or treatment of pathologies associated with alpha-glucosidase also comprises or is constituted by a quantity of VAP peptide from approximately 5 mg to approximately 7.4 mg, and/or comprises or is constituted by a quantity of AP peptide from approximately 5 mg to approximately 7.4 mg, and/or comprises or is constituted by a quantity of VAP and AP peptides from approximately 5 mg to approximately 7.4 mg.

The expression "from approximately 5 mg to approximately 7.4 mg" is to be understood as possibly indicating one of the following values: 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3 or 7.4.

In yet another aspect, said composition for the use thereof in the prevention and/or treatment of pathologies associated with alpha-glucosidase thus comprises or is constituted by a quantity of VAP peptide from approximately 7.5 mg to approximately 2250 mg or from approximately >2250 mg to 3000 mg, and/or comprises or is constituted by a quantity of AP peptide from approximately 7.5 mg to approximately 2250 mg or from approximately >2250 mg to 3000 mg, and/or comprises or is constituted by a quantity of VAP and AP peptides from approximately 7.5 mg to approximately 2250 mg or from approximately >2250 mg to 3000 mg.

In a particular aspect of the invention, said composition for the use thereof in the prevention and/or treatment of pathologies associated with alpha-glucosidase thus comprises or is constituted by a quantity of VAP peptide from approximately 5 mg to approximately 2250 mg, in particular from approximately 5 mg to approximately 7.4 mg or in particular from approximately 7.5 mg to approximately 2250 mg or a quantity of VAP peptide from approximately >2250 mg to 3000 mg.

In another particular aspect of the invention, said composition for the use thereof in the prevention and/or treatment of pathologies associated with alpha-glucosidase thus comprises or is constituted by a quantity of AP peptide from approximately 5 mg to approximately 2250 mg, in particular approximately 5 mg to approximately 7.4 mg or in particular approximately 7.5 mg to approximately 2250 mg or a quantity of AP peptide from approximately >2250 mg to 3000 mg.

In another particular aspect of the invention, said composition for the use thereof in the prevention and/or treatment of pathologies associated with alpha-glucosidase thus comprises or is constituted by a quantity of VAP and AP peptides from approximately 5 mg to approximately 2250 mg, in particular approximately 5 mg to approximately 7.4 mg or in particular approximately 7.5 mg to approximately 2250 mg.

In another particular aspect of the invention, said composition for the use thereof in the prevention and/or treatment of pathologies associated with alpha-glucosidase thus comprises or is constituted by a quantity of VAP and AP peptides from approximately >2250 mg to 3000 mg.

In another particular aspect of the invention, said composition for the use thereof in the prevention and/or treatment of pathologies associated with alpha-glucosidase thus comprises or is constituted by a quantity of VAP peptide from approximately 5 mg to approximately 2250 mg, in particular approximately 5 mg to approximately 7.4 mg or in particular approximately 7.5 mg to approximately 2250 mg, and comprises or is constituted by a quantity of AP peptide from approximately 5 mg to approximately 2250 mg, in particular approximately 5 mg to approximately 7.4 mg or in particular approximately 7.5 mg to approximately 2250 mg.

In another particular aspect of the invention, said composition for the use thereof in the prevention and/or treatment of pathologies associated with alpha-glucosidase thus comprises or is constituted by a quantity of VAP peptide from approximately >2250 mg to 3000 mg, and comprises or is constituted by a quantity of AP peptide from approximately >2250 mg to 3000 mg.

In yet another aspect, the invention relates to the composition for the use thereof in the prevention and/or treatment of pathologies associated with alpha-glucosidase as mentioned above, for use by oral administration of a quantity of XAP peptide from approximately 0.06 mg/kg to 40.0 mg/kg, three times a day at the start of a meal.

In yet another aspect, the invention relates to the composition for the use thereof in the prevention and/or treatment of pathologies associated with alpha-glucosidase as mentioned above, for use by oral administration of a quantity of XAP peptide from approximately 0.06 mg/kg to approximately 30.0 mg/kg or from approximately >30.0 mg/kg to 40 mg/kg, three times a day at the start of a meal.

The expression "approximately 0.06 mg/kg to approximately 30.0 mg/kg of XAP peptide" thus means that the composition according to the present invention may comprise all the values from 0.06 mg/kg to 30.0 mg/kg, in particular from 0.06 mg/kg to 0.08 mg/kg; from 0.06 mg/kg to 0.09 mg/kg; from 0.06 mg/kg to 0.1 mg/kg; from 0.06 mg/kg to 0.5 mg/kg; from 0.06 mg/kg to 1.0 mg/kg; from 0.06 mg/kg to 2.0 mg/kg; from 0.06 mg/kg to 5.0 mg/kg; from 0.06 mg/kg to 10.0 mg/kg; from 0.06 mg/kg to 15.0 mg/kg; from 0.06 mg/kg to 20.0 mg/kg; from 0.06 mg/kg to 25.0 mg/kg; from 0.06 mg/kg to 30.0 mg/kg.

The expression "from approximately >30.0 mg/kg to 40 mg/kg" thus means that the composition according to the present invention may comprise all the values from >30.0 mg/kg to 40 mg/kg, in particular from 31 mg/kg to 40 mg/kg; from 32 mg/kg to 40 mg/kg; from 33 mg/kg to 40 mg/kg; from 33 mg/kg to 40 mg/kg; from 34 mg/kg to 40 mg/kg; from 35 mg/kg to 40 mg/kg; from 36 mg/kg to 40 mg/kg; from 37 mg/kg to 40 mg/kg; from 38 mg/kg to 40 mg/kg; from 39 mg/kg to 40 mg/kg.

In one aspect, said composition for the use thereof in the prevention and/or treatment of pathologies associated with alpha-glucosidase thus comprises or is constituted by a quantity of VAP peptide from approximately 0.06 mg/kg to approximately 30.0 mg/kg or from approximately >30.0 mg/kg to 40 mg/kg, and/or a quantity of AP peptide from approximately 0.06 mg/kg to approximately 30.0 mg/kg or from approximately >30.0 mg/kg to 40 mg/kg, and/or a quantity of VAP and AP peptides from approximately 0.06 mg/kg to approximately 30.0 mg/kg or from approximately >30.0 mg/kg to 40 mg/kg, for oral administration three times a day at the start of a meal.

In a particular aspect, said composition for the use thereof in the prevention and/or treatment of pathologies associated with alpha-glucosidase thus comprises or is constituted by a quantity of VAP peptide from approximately 0.06 mg/kg to approximately 0.099 mg/kg, and/or a quantity of AP peptide from approximately 0.06 mg/kg to approximately 0.099 mg/kg, and/or a quantity of VAP and AP peptides from approximately 0.06 mg/kg to approximately 0.099 mg/kg, for oral administration three times a day at the start of a meal.

In yet another particular aspect, said composition for the use thereof in the prevention and/or treatment of pathologies associated with alpha-glucosidase thus comprises or is constituted by a quantity of VAP peptide from approximately 0.1 mg/kg to approximately 30.0 mg/kg or from approximately >30.0 mg/kg to 40 mg/kg, and/or a quantity of AP peptide from approximately 0.1 mg/kg to approximately 30.0 mg/kg or from approximately >30.0 mg/kg to 40 mg/kg, and/or a quantity of VAP and AP peptides from approximately 0.1 mg/kg to approximately 30.0 mg/kg or from approximately >30.0 mg/kg to 40 mg/kg, for oral administration three times a day at the start of a meal.

In a particular aspect of the invention, said composition for the use thereof in the prevention and/or treatment of pathologies comprises or is constituted by a quantity of VAP peptide from approximately 0.06 mg/kg to approximately 30.0 mg/kg, in particular approximately 0.06 mg/kg to approximately 0.099 mg/kg or in particular approximately 0.1 mg/kg to approximately 30.0 mg/kg or from approximately >30.0 mg/kg to 40 mg/kg, for oral administration three times a day at the start of a meal.

In another particular aspect, said composition for the use thereof in the prevention and/or treatment of pathologies comprises or is constituted by a quantity of AP peptide from approximately 0.06 mg/kg to approximately 30.0 mg/kg, in particular approximately 0.06 mg/kg to approximately 0.099 mg/kg or in particular approximately 0.1 mg/kg to approximately 30.0 mg/kg or from approximately >30.0 mg/kg to 40 mg/kg, for oral administration three times a day at the start of a meal.

In another particular aspect, said composition for the use thereof in the prevention and/or treatment of pathologies comprises or is constituted by a quantity of VAP and AP peptides from approximately 0.06 mg/kg to approximately 30.0 mg/kg, in particular approximately 0.06 mg/kg to approximately 0.099 mg/kg or in particular approximately 0.1 mg/kg to approximately 30.0 mg/kg or from approximately >30.0 mg/kg to 40 mg/kg, for oral administration three times a day at the start of a meal.

In yet another particular aspect, said composition for the use thereof in the prevention and/or treatment of pathologies comprises or is constituted by a quantity of VAP peptide from approximately 0.06 mg/kg to approximately 30.0 mg/kg, in particular approximately 0.06 mg/kg to approximately 0.099 mg/kg or in particular approximately 0.1 mg/kg to approximately 30.0 mg/kg and a quantity of AP peptide from approximately 0.06 mg/kg to approximately 30.0 mg/kg, in particular approximately 0.06 mg/kg to approximately 0.099 mg/kg or in particular approximately 0.1 mg/kg to approximately 30.0 mg/kg, for oral administration three times a day at the start of a meal.

In yet another particular aspect, said composition for the use thereof in the prevention and/or treatment of pathologies comprises or is constituted by a quantity from approximately >30.0 mg/kg to 40 mg/kg of VAP peptide and a quantity of AP peptide from approximately >30.0 mg/kg to 40 mg/kg, for oral administration three times a day at the start of a meal.

The present invention also relates to a pharmaceutical composition comprising a XAP peptide, in which X represents the empty set or a valine, said composition comprising or constituted by a quantity of XAP peptide from approximately 0.06 mg/kg to approximately 0.099 mg/kg, in particular approximately 0.066 mg/kg, together with a pharmaceutically acceptable vehicle.

The doses were established assuming an adult patient weighing 75 kg.

The expression "from approximately 0.06 mg/kg to approximately 0.099 mg/kg" means that the doses may be just below 0.06 mg/kg or just above 0.099 mg/kg, for example 0.059 mg/kg or 0.0999 mg/kg.

The expression "from approximately 0.06 mg/kg to approximately 0.099 mg/kg" may also indicate the following values: from 0.06 mg/kg to 0.07 mg/kg; from 0.06 mg/kg to 0.08 mg/kg; from 0.06 mg/kg to 0.09 mg/kg; from 0.07 mg/kg to 0.08 mg/kg; from 0.08 mg/kg to 0.09 mg/kg or from 0.07 mg/kg to 0.09 mg/kg.

The present invention also relates to a pharmaceutical composition as mentioned above, said composition lacking vitamin B in a particular aspect, said composition advantageously appearing to be better without vitamin B.

In another particular aspect of the invention, said pharmaceutical composition contains VAP peptide and lacks vitamin B.

In another particular aspect of the invention, said pharmaceutical composition contains AP peptide and vitamin B.

The present invention also relates to a pharmaceutical composition as mentioned above, said composition comprising or constituted by a quantity of VAP peptide from approximately 0.06 mg/kg to approximately 0.099 mg/kg, and/or a quantity of AP peptide from approximately 0.06 mg/kg to approximately 0.099 mg/kg, and/or a quantity of VAP and AP peptides from approximately 0.06 mg/kg to approximately 0.099 mg/kg.

In a particular aspect of the invention, said pharmaceutical composition comprises or is constituted by a quantity of VAP peptide from approximately 0.06 mg/kg to approximately 0.099 mg/kg.

In another particular aspect of the invention, said pharmaceutical composition comprises or is constituted by a quantity of AP peptide from approximately 0.06 mg/kg to approximately 0.099 mg/kg.

In another particular aspect of the invention, said pharmaceutical composition comprises or is constituted by a quantity of VAP and AP peptides from approximately 0.06 mg/kg to approximately 0.099 mg/kg.

In yet another particular aspect, said pharmaceutical composition comprises or is constituted by a quantity of VAP peptide from approximately 0.06 mg/kg to approximately 0.099 mg/kg, and a quantity of AP peptide from approximately 0.06 mg/kg to approximately 0.099 mg/kg.

In yet another aspect of the invention, said pharmaceutical composition comprises a XAP peptide, in which X represents the empty set or a valine, and is in unit form and comprises or is constituted by a quantity of XAP peptide from approximately 5 mg to approximately 7.4 mg, together with a pharmaceutically acceptable vehicle.

In a particular aspect of the invention, said pharmaceutical composition lacks vitamin B, said composition advantageously appearing to be better without vitamin B.

In another particular aspect of the invention, said pharmaceutical composition contains VAP peptide and lacks vitamin B.

The expression "from approximately 5 mg to approximately 7.4 mg" is to be understood as possibly indicating one of the following values: 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3 or 7.4.

In a particular aspect, said pharmaceutical composition comprises or is constituted by a quantity of VAP peptide from approximately 5 mg to approximately 7.4 mg, and/or said pharmaceutical composition comprises or is constituted by a quantity of AP peptide from approximately 5 mg to approximately 7.4 mg, and/or said pharmaceutical composition comprises or is constituted by a quantity of VAP and AP peptides from approximately 5 mg to approximately 7.4 mg. This means that in a particular aspect of the invention said pharmaceutical composition comprises or is constituted by a quantity of VAP peptide from approximately 5 mg to approximately 7.4 mg or a quantity of AP peptide from approximately 5 mg to approximately 7.4 mg or a quantity of VAP and AP peptides from approximately 5 mg to approximately 7.4 mg, or a quantity of VAP peptide from approximately 5 mg to approximately 7.4 mg and a quantity of AP peptide from approximately 5 mg to approximately 7.4 mg.

In a particular aspect, said pharmaceutical composition may also be combined with at least one peptide of type APX'.

Said pharmaceutical composition may be administered in the form of tablets, capsules, powders, pastilles, pills, granules or any other form that can be administered by the oral route, and may be in the form of sachets of powder, ampoules of liquid, bottles equipped with a dropper and the other similar forms of liquid preparations or of powder.

Preferably, the pharmaceutical composition is in the form of tablets and will be able to be swallowed with a little water at the start of a meal or crunched with the first mouthfuls of food.

In another aspect of the invention, said pharmaceutical composition may comprise one or more amylase inhibitors and/or one or more lipase inhibitors.

In addition to the therapeutic aspect mentioned above, the XAP peptides according to the present invention may also be used in the nutraceutical area (as a food supplement for example) or in the food area (functional foods).

The term nutraceutical refers to the active ingredient present in the natural state or in synthetic form in a food that provides a beneficial effect on health. For example the yoghurt Danacol® from Danone contains plant sterols not present naturally in yoghurt. They are active ingredients that have been added. A foodstuff for everyday consumption (for example a drink, a milk product, cereals, biscuits) may contain a nutraceutical active ingredient and can be regarded as a functional food if it has been demonstrated that it has a beneficial effect on one or more target functions of the body, beyond the basic nutritional effects.

There are 5 approaches for making a food functional: by removing a component that is known or identified as having harmful effects, by increasing the concentration of a natural component in a food, by adding a component normally absent from the majority of foods (but that possesses proven beneficial effects), by replacing a component or by improving the bioavailability of the food components.

Food supplements are foodstuffs whose purpose is to supplement the normal diet and which constitute a concentrated source of nutrients or of other substances having a nutritional or physiological effect, either alone or combined. Such foodstuffs are intended to be taken in measured units in small quantities.

In another aspect, the invention also relates to the use of at least one XAP peptide, in which X represents the empty set or a valine, for the preparation of a nutraceutical composition or a food supplement.

In a particular aspect, the invention relates to the use of at least one VAP peptide.

In a particular aspect, the invention relates to the use of at least one AP peptide.

In a particular aspect, the invention relates to the use of at least one VAP peptide and the use of at least one AP peptide.

In yet another aspect, the invention thus relates to a nutraceutical or food composition for inhibiting alpha-glucosidase, and in particular maltase, said composition comprising at least one XAP peptide, in which X represents the empty set or a valine, said composition comprising a quantity of XAP peptide from approximately 0.06 mg/kg to approximately 14 mg/kg.

In yet another aspect, the invention thus relates to a nutraceutical or food composition for inhibiting alpha-glucosidase, and in particular maltase, said composition comprising at least one XAP peptide, in which X represents the empty set or a valine, said composition comprising a quantity of XAP peptide from approximately 0.06 mg/kg to <0.6 mg/kg or from approximately 0.6 mg/kg to approximately 14 mg/kg.

In a particular aspect, said nutraceutical or food composition lacks vitamin B, said composition advantageously appearing to be better without vitamin B.

In another particular aspect of the invention, said nutraceutical or food composition contains VAP peptide and lacks vitamin B.

In another particular aspect of the invention, said nutraceutical or food composition contains AP peptide and vitamin B.

In another particular aspect of the invention, the nutraceutical or food composition comprises a quantity of VAP peptide from approximately 0.06 mg/kg to <0.6 mg/kg or from approximately 0.6 mg/kg to approximately 14 mg/kg, and/or a quantity of AP peptide from approximately 0.06 mg/kg to <0.6 mg/kg or from approximately 0.6 mg/kg to approximately 14 mg/kg, and/or a quantity of VAP and AP peptides from approximately 0.06 mg/kg to <0.6 mg/kg or from approximately 0.6 mg/kg to approximately 14 mg/kg.

The expression "from approximately 0.06 mg/kg to <0.6 mg/kg" is to be understood as possibly covering values just below 0.06 mg/kg, for example 0.059 mg/kg.

The expression "<0.6 mg/kg" means values strictly below 0.6 mg/kg.

The expression "from approximately 0.06 mg/kg to <0.6 mg/kg" may also indicate the following values: from 0.06 mg/kg to 0.58 mg/kg; from 0.08 mg/kg to 0.58 mg/kg; from 0.1 mg/kg to 0.58 mg/kg; from 0.12 mg/kg to 0.58 mg/kg; from 0.13 mg/kg to 0.58 mg/kg; from 0.15 to 0.58 mg/kg; from 0.20 mg/kg to 0.58 mg/kg; from 0.25 mg/kg to 0.58 mg/kg; from 0.30 mg/kg to 0.58 mg/kg; from 0.35 mg/kg to 0.58 mg/kg; from 0.40 mg/kg to 0.58 mg/kg; from 0.45 mg/kg to 0.58 mg/kg; from 0.50 mg/kg to 0.58 mg/kg; from 0.55 mg/kg to 0.58 mg/kg.

The expression "from approximately 0.6 mg/kg to approximately 14 mg/kg" is to be understood as possibly covering values just below 0.6 mg/kg, for example 0.59 mg/kg, or values just above 14 mg/kg, for example 14.1 mg/kg.

The expression "from approximately 0.6 mg/kg to approximately 14 mg/kg" may also indicate the following values: 0.6 mg/kg; 0.8 mg/kg; 1.0 mg/kg; 1.2 mg/kg; 1.4 mg/kg; 1.6 mg/kg; 1.8 mg/kg; 2.0 mg/kg; 2.2 mg/kg; 2.4 mg/kg; 2.6 mg/kg; 2.8 mg/kg; 3.0 mg/kg; 3.2 mg/kg; 3.4 mg/kg; 3.6 mg/kg; 3.8 mg/kg; 3.0 mg/kg; 3.2 mg/kg; 3.4 mg/kg; 3.6 mg/kg; 3.8 mg/kg; 4.0 mg/kg; 4.2 mg/kg; 4.4 mg/kg; 4.6 mg/kg; 4.8 mg/kg; 5.0 mg/kg; 5.2 mg/kg; 5.4 mg/kg; 5.6 mg/kg; 5.8 mg/kg; 6.0 mg/kg; 6.2 mg/kg; 6.4 mg/kg; 6.6 mg/kg; 6.8 mg/kg; 7.0 mg/kg; 7.2 mg/kg; 7.4 mg/kg; 7.6 mg/kg; 7.8 mg/kg; 8.0 mg/kg; 8.2 mg/kg; 8.4 mg/kg; 8.6 mg/kg; 8.8 mg/kg; 9.0 mg/kg; 9.2 mg/kg; 9.4 mg/kg; 9.6 mg/kg; 9.8 mg/kg; 10.0 mg/kg; 10.2 mg/kg; 10.4 mg/kg; 10.6 mg/kg; 10.8 mg/kg; 11.2 mg/kg; 11.4 mg/kg; 11.6 mg/kg; 11.8 mg/kg; 12.2 mg/kg; 12.4 mg/kg; 12.6 mg/kg; 12.8 mg/kg; 13.0 mg/kg; 13.2 mg/kg; 13.4 mg/kg; 13.6 mg/kg; 13.8 mg/kg and 14.0 mg/kg, or from 0.6 mg/kg to 0.9 mg/kg; from 2 mg/kg to 3 mg/kg or 4 mg/kg or 5 mg/kg or 6 mg/kg or 7 mg/kg or 8 mg/kg or 9 mg/kg or 10 mg/kg or 11 mg/kg or 12 mg/kg or 13 mg/kg or 14 mg/kg.

In yet another particular aspect, said nutraceutical or food composition comprises a quantity of VAP peptide from approximately 0.06 mg/kg to <0.6 mg/kg or from approximately 0.6 mg/kg to approximately 14 mg/kg.

In yet another particular aspect, said nutraceutical or food composition comprises a quantity of AP peptide from approximately 0.06 mg/kg to <0.6 mg/kg or from approximately 0.6 mg/kg to approximately 14 mg/kg.

In yet another particular aspect, said nutraceutical or food composition comprises a quantity of VAP and AP peptides from approximately 0.06 mg/kg to <0.6 mg/kg or from approximately 0.6 mg/kg to approximately 14 mg/kg.

In yet another aspect, said nutraceutical or food composition comprises a quantity of VAP peptide from approximately 0.06 mg/kg to <0.6 mg/kg or from approximately 0.6 mg/kg to approximately 14 mg/kg, and a quantity of AP peptide from approximately 0.06 mg/kg to <0.6 mg/kg or from approximately 0.6 mg/kg to approximately 14 mg/kg.

In a particular aspect, said nutraceutical or food composition may also be combined with at least one peptide of type APX'.

In a particular aspect, said nutraceutical or food composition may be administered in the form of tablets, capsules, powders, pastilles, pills, granules or any other form that can be administered by the oral route, and may be in the form of sachets of powder, ampoules of liquid, bottles equipped with a dropper and the other similar forms of liquid preparations or of powder.

Preferably, said nutraceutical or food composition is in the form of tablets and will be able to be swallowed with a little water at the start of a meal or crunched with the first mouthfuls of food.

In yet another aspect, the invention also relates to a nutraceutical or food composition for inhibiting alpha-glucosidase, and in particular maltase, said composition comprising at least one XAP peptide, in which X represents the empty set or a valine, said composition being in unit form and comprising a quantity of XAP peptide from approximately 5 mg to approximately 1000 mg.

In yet another aspect, the invention also relates to a nutraceutical or food composition for inhibiting alpha-glucosidase, and in particular maltase, said composition comprising at least one XAP peptide, in which X represents the empty set or a valine, said composition being in unit form and comprising a quantity of XAP peptide from approximately 5 mg to <50 mg or from approximately 50 mg to approximately 1000 mg.

In a particular aspect, said nutraceutical or food composition lacks vitamin B, said composition advantageously appearing to be better without vitamin B.

In another particular aspect of the invention, said nutraceutical or food composition contains VAP peptide and lacks vitamin B.

In another particular aspect of the invention, said nutraceutical or food composition contains AP peptide and vitamin B.

The expression "from approximately 5 mg to <50 mg" is to be understood as possibly covering values just below 5 mg, for example 4.9 mg.

The expression "<50 mg" means values strictly below 50 mg.

The expression "from approximately 5 mg to <50 mg" may indicate all the values from 10 mg to <50 mg, for example from 5 mg to 49 mg; from 10 mg to 49 mg; from 15 mg to 49 mg; from 20 mg to 49 mg; from 25 mg to 49 mg; from 30 mg to 49 mg; from 35 mg to 49 mg; from 40 to 49 mg; from 45 mg to 49 mg.

The expression "from approximately 50 mg to approximately 1000 mg" is to be understood as possibly covering values just below 50 mg, for example 49.9 mg, or values just above 1000 mg, for example 1000.01 mg.

The expression "from approximately 50 mg to approximately 1000 mg" may indicate all the values from 50 mg to 1000 mg, for example from 50 mg to 100 mg; from 100 mg to 200 mg; from 200 mg to 300 mg; from 300 mg to 400 mg; from 400 mg to 500 mg; from 500 mg to 600 mg; from 600 mg to 700 mg; from 800 mg to 900 mg or from 900 mg to 1000 mg.

In another aspect, the invention also relates to a nutraceutical or food composition for inhibiting alpha-glucosidase, and in particular maltase, comprising a quantity of VAP peptide from approximately 5 mg to <50 mg or from approximately 50 mg to approximately 1000 mg, and/or a quantity of AP peptide from approximately 5 mg to <50 mg or from approximately 50 mg to approximately 1000 mg, and/or a quantity of VAP and AP peptides from approximately 5 mg to <50 mg or from approximately 50 mg to approximately 1000 mg. This thus means that said nutraceutical or food composition for inhibiting alpha-glucosidase comprises a quantity of VAP peptide from approximately 5 mg to <50 mg or from approximately 50 mg to approximately 1000 mg or a quantity of AP peptide from approximately 5 mg to <50 mg or from approximately 50 mg to approximately 1000 mg or a quantity of VAP and AP peptides from approximately 5 mg to <50 mg or from approximately 50 mg to approximately 1000 mg, or a quantity of VAP peptide from approximately 5 mg to <50 mg or from approximately 50 mg to approximately 1000 mg and a quantity of AP peptide from approximately 5 mg to <50 mg or from approximately 50 mg to approximately 1000 mg.

In another embodiment, the invention relates to the use of a composition containing any peptide that is an inhibitor of alpha-glucosidase, and in particular any peptide that is an inhibitor of maltase, having a maximum $IC_{50}$ with respect to alpha-glucosidase, and in particular maltase, of 12.50 mM for the prevention and/or treatment of pathologies associated with alpha-glucosidase. $IC_{50}$ represents the necessary concentration of peptide for inhibiting 50% of the activity of the enzyme.

In yet another aspect, the invention also relates to the use of a hydrolysate of at least one protein comprising or constituted by at least 0.05% of XAP units, in place of the XAP peptide as mentioned above.

In a particular aspect, said hydrolysate is not used in combination with an insulin sensitizer. An "insulin sensitizer" means any molecule that makes it possible to lower the blood level of glucose, with the exception of the XAP peptides and/or APX'. An insulin sensitizer may for example be chromium, vanadium, vitamin B (in particular niacin), or herbs or plant extracts, preferably from *Banaba* leaves, ginseng berries, cinnamon and certain compounds in grapes. The following compounds are also considered to be "insulin sensitizers": corosolic acid, pterostilbene, methylhydroxy chalcone polymer (MHCP) and the ginsensosides. Preferred examples of "insulin sensitizers" are biguanides (such as metformin (Glucophage®), the thiazolidinediones (such as pioglitazone (Actos®) and rosiglitazone (Avandia®).

In yet another aspect, the invention also relates to the use of a hydrolysate of at least one protein comprising or constituted by at least 5% of XAP units, in place of the XAP peptide as mentioned above.

The invention thus relates to the use of a hydrolysate of at least one protein comprising or constituted by at least 0.05% to <5% of XAP units or the use of a hydrolysate of at least one protein comprising or constituted by at least 5% of XAP units, in place of the XAP peptide as mentioned above.

In another aspect, the invention also relates to the use of a hydrolysate of at least one protein comprising or constituted by at least 0.05% to <5% of XAP units or the use of a hydrolysate of at least one protein comprising or constituted by at least 5% of XAP units, as an alpha-glucosidase inhibitor.

In another particular aspect, the invention thus relates to a composition comprising or consisting of at least one hydrolysate of at least one protein, said protein comprising or constituted by at least 0.05% to <5% or of at least 5% of XAP units, in which X represents the empty set or a valine, for use in the prevention and/or treatment of pathologies associated with alpha-glucosidase.

The expression "at least one hydrolysate of at least one protein" means that the hydrolysate may be derived from a single protein or from a mixture of proteins.

In said "mixture of proteins", the proteins may be from different sources or from the same source. A mixture of proteins from different sources may for example be a mixture of salmon proteins and carp proteins. A mixture of proteins from the same source may for example be a mixture of salmon proteins.

The expression "<5% of XAP units" means values strictly below 5% of XAP units, in particular 4.9%.

The expression "said protein comprising or constituted by at least 0.05% to <5% of XAP units" means that the total amino acid sequence of said protein comprises or is constituted by at least 0.05% of XAP units, up to a value below 5%, of XAP units, relative to the sum total of the amino acids making up the sequence.

The expression "at least 0.05% of XAP units" means that said protein may comprise or be constituted by 0.05% to 100% of XAP units, and in particular 0.05%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

The expression "said protein comprising or constituted by at least 5% of XAP units" means that the total amino acid sequence of said protein comprises or is constituted by at least 5% of XAP units relative to the sum total of the amino acids making up the sequence.

The expression "at least 5% of XAP units" means that said protein may comprise or be constituted by 5% to 100% of XAP units, and in particular 5%, 10%, 15%, 20%, 25%, 30%, 35%, 40%, 45%, 50%, 55%, 60%, 65%, 70%, 75%, 80%, 85%, 90%, 95%, 100%.

Said XAP units may be distributed over the entire length of the sequence, or be localized on just one part of the sequence. In the latter case, the sequence of said protein thus comprises a succession of XAP units, for example XAP-XAP-XAP-XAP or a succession of XAP units intercalated with amino acids (AA) other than valine, alanine or proline, for example AA-XAP-XAP-AA-XAP-XAP-XAP-AA.

It being understood, as was mentioned above, that the term "XAP" is to be understood as the VAP tripeptide or the AP dipeptide, said protein comprising or constituted by at least 0.05% to <5% or of at least 5% of XAP units may be constituted by at least 0.05% to <5% or of at least 5% of VAP units or of at least 0.05% to <5% or of at least 5% of AP peptide or of at least 0.05% to <5% or of at least 5% of VAP and AP units, or of at least 0.05% to <5% or of at least 5% of VAP units and of at least 0.05% to <5% or of at least 5% of AP units.

When said protein comprises at least 0.05% to <5% or at least 5% of VAP and AP units, the sequence of the latter comprises VAP units and AP units, and the sum of the percentages of the VAP and AP units relative to the sum total of the amino acids making up the sequence has to be at least from 0.05% to <5% or 5%.

When said protein comprises at least 0.05% to <5% or at least 5% of VAP and AP units, the VAP and AP units may be distributed over the entire length of the sequence, or be localized on just one part of the sequence. Said VAP units may be distributed separately from the AP units, or the VAP units may be combined with the AP units.

In one aspect of the invention, said composition comprising or consisting of at least one hydrolysate is used in the prevention and/or treatment of pathologies associated with alpha-glucosidase, in particular type 2 diabetes.

In another aspect of the invention, the hydrolysate is used as an alpha-glucosidase inhibitor.

In another aspect, in said composition comprising or consisting of at least one hydrolysate, said protein comprises or is constituted by at least 0.05% to <5% or of at least 5% of VAP units and/or comprises or is constituted by at least 0.05% to <5% or of at least 5% of AP units. This means that in said composition comprising or consisting of at least one hydrolysate, said protein comprises or is constituted by at least 0.05% to <5% or of at least 5% of VAP units, or said protein comprises or is constituted by at least 0.05% to <5% or of at least 5% of AP units. This thus means that in said composition comprising or consisting of at least one hydrolysate, said protein comprises or is constituted by at least 0.05% to <5% or of at least 5% of VAP units and said protein comprises or is constituted by at least 0.05% to <5% or of at least 5% of AP units.

In one aspect of the invention, in said composition comprising or consisting of at least one hydrolysate, said protein comprises or is constituted by at least 0.05% to <5% or of at least 5% of VAP and AP units.

In another particular aspect, the invention thus relates to a composition for the use thereof in the prevention and/or treatment of pathologies associated with alpha-glucosidase comprising or consisting of at least one hydrolysate of at least one protein, said protein comprising or consisting of at least 0.05% to <5% or of at least 5% of XAP units, in which X represents the empty set or a valine, in combination with at least one peptide of type APX'.

In another particular aspect, the invention thus relates to a composition for the use thereof in the prevention and/or treatment of pathologies associated with alpha-glucosidase comprising or constituted by at least one hydrolysate of at least one protein, said protein comprising or consisting of at least 0.05% to <5% or of at least 5% of XAP units, in which X represents the empty set or a valine, in association with at least one APFPE (SEQ ID NO: 1) and/or APFPEVF (SEQ ID NO: 2).

Thus, in a particular aspect of the invention, the composition for the use thereof in the prevention and/or treatment of pathologies associated with alpha-glucosidase comprises or is constituted by at least the following combinations:

- a hydrolysate of at least one protein, said protein comprising or constituted by at least 0.05% to <5% or of at least 5% of AP units+the peptide APFPE (SEQ ID NO: 1), or
- a hydrolysate of at least one protein, said protein comprising or constituted by at least 0.05% to <5% or of at least 5% of AP units+the peptide APFPEVF (SEQ ID NO: 2), or
- a hydrolysate of at least one protein, said protein comprising or constituted by at least 0.05% to <5% or of at least 5% of VAP units+the peptide APFPE (SEQ ID NO: 1), or
- a hydrolysate of at least one protein, said protein comprising or constituted by at least 0.05% to <5% or of at least 5% of VAP units+the peptide APFPEVF (SEQ ID NO: 2), or
- a hydrolysate of at least one protein, said protein comprising or constituted by at least 0.05% to <5% or of at least 5% of AP units+the peptide APFPE (SEQ ID NO: 1)+the peptide APFPEVF (SEQ ID NO: 2), or
- a hydrolysate of at least one protein, said protein comprising or constituted by at least 0.05% to <5% or of at least 5% of VAP units+the peptide APFPE (SEQ ID NO: 1)+the peptide APFPEVF (SEQ ID NO: 2), or
- a hydrolysate of at least one protein, said protein comprising or constituted by at least 0.05% to <5% or of at least 5% of AP units+a hydrolysate of at least one protein, said protein comprising or consisting of at least 0.05% to <5% or of at least 5% of VAP units+the peptide APFPE (SEQ ID NO: 1)+the peptide APFPEVF (SEQ ID NO: 2), or
- a hydrolysate of at least one protein, said protein comprising or constituted by at least 0.05% to <5% or of at least 5% of AP units+a hydrolysate of at least one protein, said protein comprising or consisting of at least 0.05% to <5% or of at least 5% of VAP units+the peptide APFPE (SEQ ID NO: 1), or
- a hydrolysate of at least one protein, said protein comprising or constituted by at least 0.05% to <5% or of at least 5% of AP units+a hydrolysate of at least one protein, said protein comprising or constituted by at least 0.05% to <5% or of at least 5% of VAP units+the peptide APFPEVF (SEQ ID NO: 2).

In another particular aspect, the present invention also relates to a pharmaceutical composition comprising or consisting of at least one hydrolysate of at least one protein, said protein comprising or constituted by at least 0.05% to <5% or of at least 5% of XAP units, in which X represents the empty set or a valine.

In another particular aspect, said pharmaceutical composition comprising or consisting of at least one hydrolysate may also comprise at least one peptide of type APX'.

In a particular aspect, said pharmaceutical composition comprising or consisting of at least one hydrolysate may be administered in the form of tablets, capsules, powders, pastilles, pills, granules or any other form that can be administered by the oral route, and may be in the form of sachets of powder, ampoules of liquid, bottles equipped with a dropper and the other similar forms of liquid preparations or of powder.

In a particular aspect of the invention, the hydrolysate may also be incorporated in a food matrix. A food matrix means drinks, yoghurts, confectionery, cereals, soups, sauces, fruit and vegetable juices, fats, seasonings, bread.

Preferably, said pharmaceutical composition comprising or consisting of at least one hydrolysate is in the form of tablets and will be able to be swallowed with a little water at the start of a meal or crunched with the first mouthfuls of food.

In addition to the therapeutic aspect mentioned above, the hydrolysates of at least one protein comprising or constituted by at least 0.05% to <5% or of at least 5% of XAP units according to the present invention may also be used in the nutraceutical area or in the food area (as food supplement for example).

The invention thus relates to the use of at least one hydrolysate of at least one protein, said protein comprising or constituted by at least 0.05% to <5% or of at least 5% of XAP units, in which X represents the empty set or a valine, for the preparation of a nutraceutical composition or a food supplement.

In a particular aspect, in said use of at least one hydrolysate of at least one protein, said protein comprises or is constituted by at least 0.05% to <5% or of at least 5% of VAP units.

In a particular aspect, in said use of at least one hydrolysate of at least one protein, said protein comprises or is constituted by at least 0.05% to <5% or of at least 5% of AP units.

In a particular aspect, in said use of at least one hydrolysate of at least one protein, said protein comprises or is constituted by at least 0.05% to <5% or of at least 5% of VAP and AP units.

In a particular aspect, in said use of at least one hydrolysate of at least one protein, said protein comprises or is constituted by at least 0.05% to <5% or of at least 5% of VAP units and said protein comprises or is constituted by at least 0.05% to <5% or of at least 5% of AP units.

In another particular aspect, the invention relates to a nutraceutical or food composition comprising or consisting of at least one hydrolysate of at least one protein, said protein comprising or constituted by at least 0.05% to <5% or of at least 5% of XAP units, in which X represents the empty set or a valine.

In another particular aspect, said nutraceutical or food composition comprising or consisting of at least one hydrolysate may also comprise at least one peptide of type APX'.

In a particular aspect, said nutraceutical or food composition comprising or consisting of at least one hydrolysate may be administered in the form of tablets, capsules, powders, pastilles, pills, granules or any other form that can be administered by the oral route, and may be in the form of sachets of powder, ampoules of liquid, bottles equipped with a dropper and the other similar forms of liquid preparations or of powder.

Preferably, said nutraceutical or food composition comprising or consisting of at least one hydrolysate is in the form of tablets and will be able to be swallowed with a little water at the start of a meal or crunched with the first mouthfuls of food.

In another aspect, the invention also relates to a method for the preparation of a hydrolysate of at least one protein comprising or constituted by at least 0.05% to <5% or of at least 5% of XAP units, in which X represents the empty set or a valine.

Said hydrolysate may be obtained by a chemical route or by an enzymatic route.

Chemical hydrolysis is carried out using a strong acid, for example HCl in a quantity of 3M, from 12 hours to 24 hours.

Said chemical hydrolysis is also carried out under strict conditions of pH, more particularly at pH 2.

It should be noted, however, that this chemical hydrolysis may impair the quality of the hydrolysate obtained. Hydrolysis by the enzymatic route is thus preferred.

In one aspect, the invention thus relates to a method for the preparation of a hydrolysate of at least one protein comprising or constituted by at least 0.05% to <5% or of at least 5% of XAP units, in which X represents the empty set or a valine, comprising the following steps:
  Dissolution of at least one protein comprising or consisting of at least 0.05% to <5% or of at least 5% of XAP units in water to obtain an aqueous solution;
  Addition of at least one enzyme to said aqueous solution in a suitable quantity for hydrolysing said protein.

"Addition of at least one enzyme" means that the hydrolysate may be produced by a mixture of enzymes or by a hydrolysis sequence.

A "hydrolysis sequence" means at least two hydrolysis steps (enzyme A then enzyme B for example, enzyme A serving to achieve maximum hydrolysis).

In one aspect, the invention thus relates to a method for the preparation of a hydrolysate of at least one protein comprising or constituted by at least 0.05% to <5% or of at least 5% of XAP units, in which X represents the empty set or a valine, comprising the following steps:
  Dissolution of at least one protein comprising or constituted by at least 0.05% to <5% or of at least 5% of XAP units in water to obtain an aqueous solution;
  Addition of an enzyme to said aqueous solution in a suitable quantity for hydrolysing said protein.

In a particular aspect of the invention, dissolution of at least one protein in water consists of grinding at least one protein source.

This therefore means that the initial raw material of said method for the preparation of a hydrolysate may be either a protein, in particular a commercially available purified protein, or a ground product from at least one protein source.

Purified proteins are for example commercially available from BNLfood (Belovo) (<http://www.bnlfood.com/>); Setalg (<http://www.setalg.fr/>); Copalis (<http://www.copalis.fr/fr/>); Vegan (<http://www.veganproteins.com/>); Solabia (<http://www.solabia.fr>), etc.

A "ground product from at least one protein source" may for example be an animal flour, for example a fish flour, or a ground product from fish meat. Said protein source may for example be of vegetable origin, of marine origin or of animal origin, or even derived from insects.

When the initial raw material of said method for the preparation of a hydrolysate is in the form of powder (a fish flour for example), then a simple dissolution is required.

When the initial raw material of said method for the preparation of a hydrolysate comprises protein-rich co-products (for example fish fillets, a cake, algae, etc.), a grinding operation is then required.

In a particular aspect, the invention also relates to a method for the preparation of a hydrolysate as mentioned above, said method comprising the following steps:
  Dissolution of at least one protein comprising or constituted by at least 0.05% to <5% or of at least 5% of XAP units in water to obtain an aqueous solution;
  Incubation of said aqueous solution for 15 minutes at 90° C.;
  Addition of at least one enzyme to said aqueous solution in a suitable quantity for hydrolysing said protein;
  Incubation of the aqueous solution obtained in the preceding step for a period of from 6 to 24 hours, at a temperature from 35° C. to 55° C.

In another particular aspect, the invention also relates to a method for the preparation of a hydrolysate as mentioned above, said method comprising the following steps:
  Dissolution of at least one protein comprising or constituted by at least 0.05% to <5% or of at least 5% of XAP units in water to obtain an aqueous solution;
  Incubation of said aqueous solution for 15 minutes at 90° C.;
  Addition of an enzyme to said aqueous solution in a suitable quantity for hydrolysing said protein;
  Incubation of the aqueous solution obtained in the preceding step for a period of from 6 to 24 hours, at a temperature from 35° C. to 55° C.

The aforementioned incubation aims to denature the proteins and promote proteolysis.

The expression "a period of from 6 to 24 hours" is to be understood as all the hours from 6 to 24 hours, namely 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, and 24 hours. This also means 6 hours and 30 minutes, 7 hours and 30 minutes, 8 hours and 30 minutes, 9 hours and 30 minutes, 10 hours and 30 minutes, 11 hours and 30 minutes, 12 hours and 30 minutes, 13 hours and 30 minutes, 14 hours and 30 minutes, 15 hours and 30 minutes, 16 hours and 30 minutes, 17 hours and 30 minutes, 18 hours and 30 minutes, 19 hours and 30 minutes, 20 hours and 30 minutes, 21 hours and 30 minutes, 22 hours and 30 minutes, 23 hours and 30 minutes and 24 hours and 30 minutes.

The expression "temperature from 35° C. to 55° C." is to be understood as all the temperatures from 35° C. to 55° C., namely 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., and 55° C.

In a particular aspect of the method of preparation as mentioned above, the suitable quantity of enzyme for hydrolysing a solution of proteins from 5 to 25% (w/w) is from 0.1% to 5% of the weight of the protein extract.

In a particular aspect of the method of preparation as mentioned above, said method comprises one or more steps of adjustment of the pH as a function of the enzyme used, in particular by adding HCl or KOH and/or NaOH in a suitable quantity to obtain a pH between 3.5 and 8.

In a particular aspect of the method of preparation as mentioned above, said method comprises one or more steps of inactivating the enzyme.

The enzyme may be inactivated by increasing the temperature of the reaction medium to 95° C. for 15 minutes so as to stop the proteolysis by thermal denaturation of the enzyme.

In a particular aspect of the method of preparation as mentioned above, said method comprises a step of separating said hydrolysate obtained from the rest of the reaction medium.

In a particular aspect of the method of preparation as mentioned above, separation of the hydrolysate of at least one protein from the rest of the reaction mixture is carried out by centrifugation at a speed of between 4000 and 7000 rpm, and then removal of the pellet obtained.

In another particular aspect of the method of preparation as mentioned above, said method also comprises a filtration step prior to said centrifugation step. Filtration of the reaction medium makes it possible to remove the solid matter.

Enzymatic hydrolysis is carried out with an enzyme carefully selected to make it possible to obtain a hydrolysate of at least one protein comprising or constituted by at least 0.05% to <5% or of at least 5% of XAP units.

Enzymatic hydrolysis is carried out with a preparation of purified enzyme or with an unpurified mixture. The enzyme preparation may contain endo- or exo-peptidases, proteases or a mixture.

In a particular aspect of the method of preparation as mentioned above, the enzyme is selected from Alcalase, Flavourzyme, peptidase, Promod, pepsin, trypsin, protease N or Protamex.

In a particular aspect of the method of preparation as mentioned above, the enzyme preparation used is Flavourzyme (protease/peptidase mixture).

In another particular aspect of the method of preparation as mentioned above, the enzyme preparation used is Protamex (mixture of proteases (Alcalase from *Bacillus licheniformis* and Neutrase from *Bacillus amyloliquefaciens*)).

In another aspect, hydrolysis is carried out with a succession of enzymes, namely Protamex, and then pepsin.

Moreover, in a particular aspect of the invention, the hydrolysate of at least one protein as mentioned above may be used alone or in combination with other molecules.

For the purposes of the present invention, said VAP and AP peptides may be synthetic peptides, peptides of vegetable origin, of marine origin or of animal origin, or even peptides derived from insect proteins.

The same applies to the peptides contained in the hydrolysates defined above.

The peptides of vegetable origin may thus be derived from proteins from leguminous plants; proteins from cereals; proteins from oleaginous seeds; or proteins from oleaginous fruits.

The peptides of marine origin may thus be derived from fish proteins or proteins from algae.

The peptides of animal origin may thus be derived from egg proteins or milk proteins.

The peptides derived from insects may thus be derived from edible insect proteins.

Still for the purposes of the present invention, the protein comprising or constituted by at least 0.05% to <5% or of at least 5% of XAP units is also selected from fish protein, protein from algae, milk protein, protein from leguminous plants, protein from cereals, protein from oleaginous seeds, protein from oleaginous fruits and protein from edible insects.

In a particular aspect of the invention, said fish protein is thus selected from the proteins from carp, salmon, sardine, hake, cod and haddock.

In another particular aspect, said protein from algae is selected from the proteins from *chondrus, palmaria, ulva, porphyra, laminaria, ascophyllum, undaria* and *himanthallia*.

In another particular aspect, said egg protein is selected from ovomucin, lysozyme and ovotransferrin.

In another particular aspect, said milk protein is selected from whey and casein proteins. The milk may in particular be from a cow, mare or ewe. More particularly, said milk proteins may be a beta-lactoglobulin, a casein, in particular an alpha-S1-casein or a beta-casein, a lactoferrin.

In another particular aspect, said protein from leguminous plants is selected from the proteins from lentils, white and green beans, chick peas, beans, split peas and soya. More particularly, said protein may be a legumin, in particular a legumin A.

In another particular aspect, said protein from cereals is selected from proteins from maize, millet, barley, rye, buckwheat, quinoa and rice.

In another particular aspect, said protein from oleaginous seeds is selected from proteins from peanut, pumpkin, flax, and cucurbit.

In another particular aspect, said protein from the proteins of oleaginous fruits is selected from proteins from almonds, walnuts, peanuts, hazelnuts, pine nuts, pistachios, argon and the olive tree.

In another particular aspect, said protein from edible insect proteins is selected from proteins from crickets, locusts, grasshoppers and mealworms.

The protein according to the invention may also be a fibrous protein, in particular elastin, collagen or actin. The actin may in particular be of marine origin (derived from salmon), the elastin of animal origin (derived from bovines), and the collagen of animal or marine origin (derived from bovines or from salmon).

The invention will be better illustrated by the following examples and the figures. The examples given below aim to clarify the subject-matter of the invention and illustrate advantageous embodiments, but in no case are intended to restrict the scope of the invention.

LEGENDS OF THE FIGURES

FIG. 1 shows the variation of the percentage inhibition of the activity of alpha-glucosidase as a function of the concentration of acarbose.

The abscissa shows the concentration of acarbose (in mM), and the ordinate shows the percentage inhibition of alpha-glucosidase.

Figure 2:
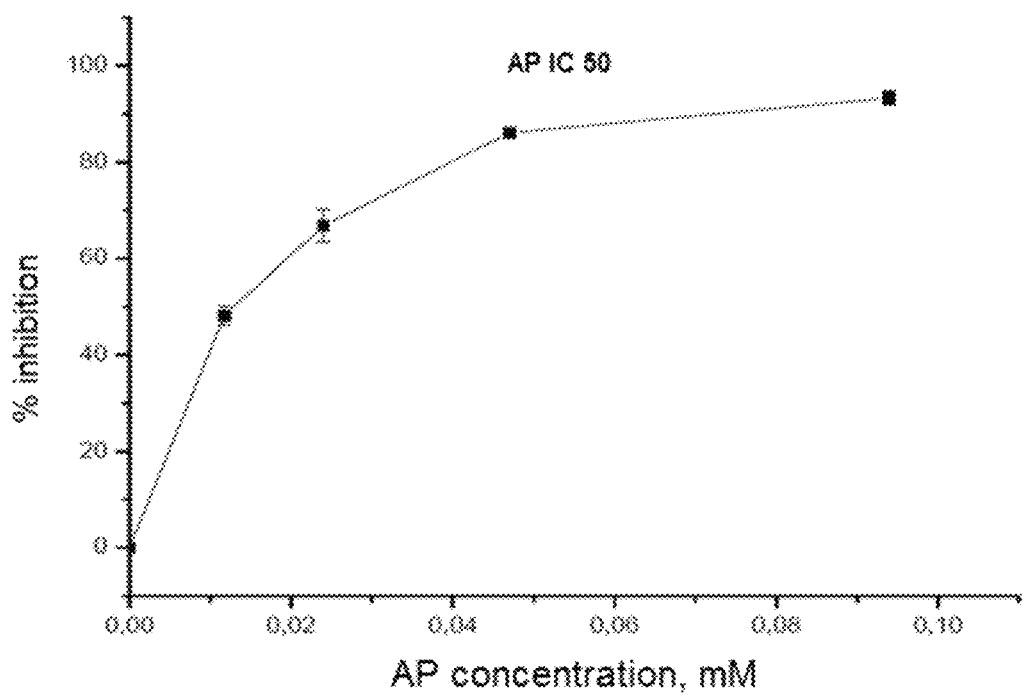

FIG. 2 shows the variation of the percentage inhibition of the activity of alpha-glucosidase as a function of the concentration of AP peptide.

The abscissa shows the concentration of AP peptide (in mM), and the ordinate shows the percentage inhibition of alpha-glucosidase.

Figure 3:
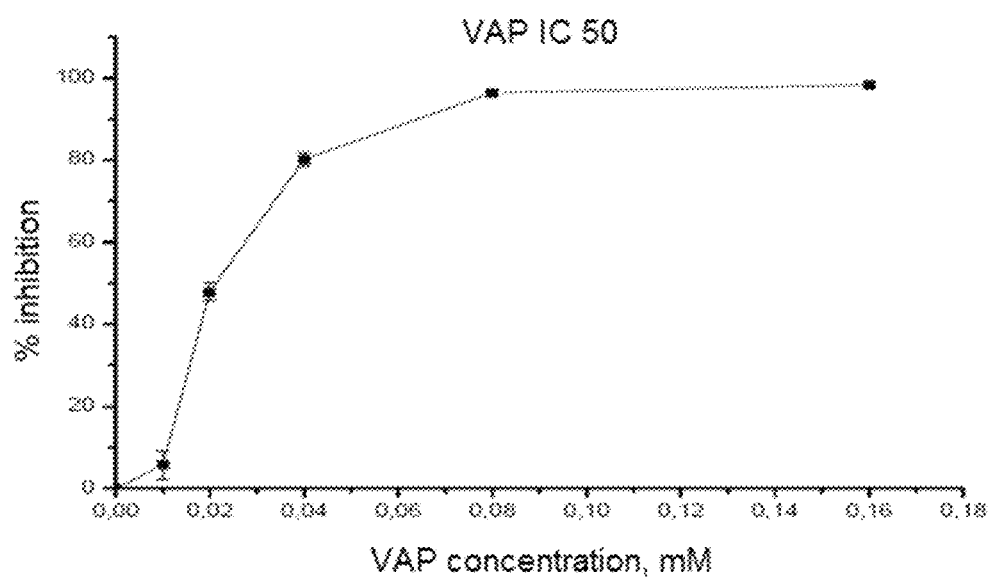

FIG. 3 shows the variation of the percentage inhibition of the activity of alpha-glucosidase as a function of the concentration of VAP peptide.

The abscissa shows the concentration of VAP peptide (in mM), and the ordinate shows the percentage inhibition of alpha-glucosidase.

Figure 4:
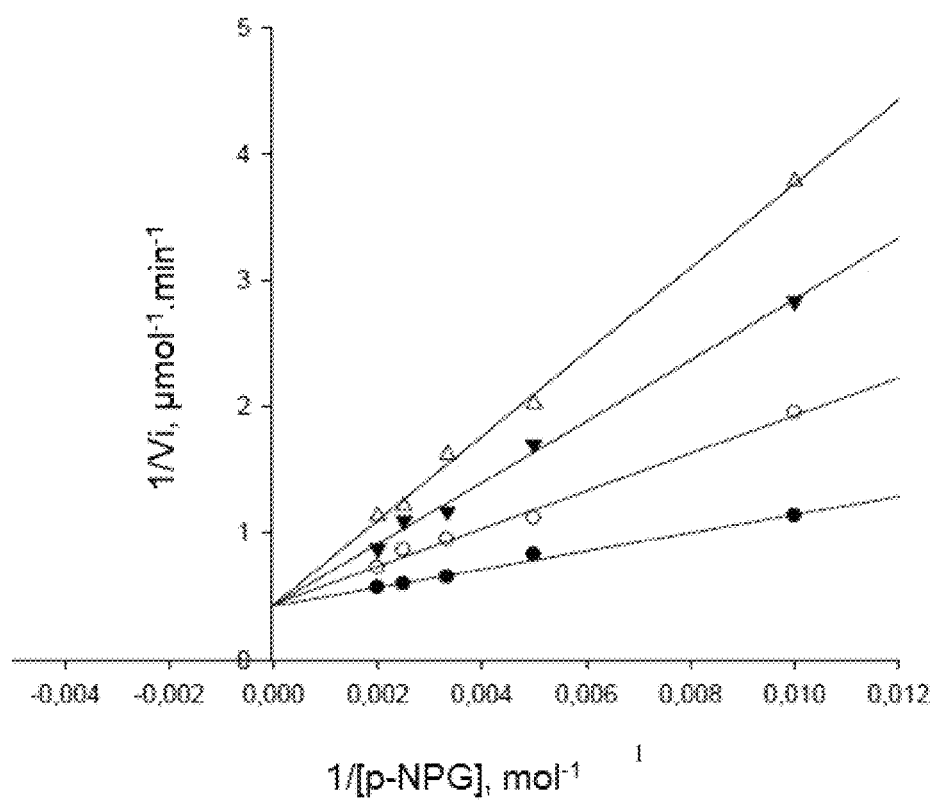

FIG. 4 shows Lineweaver-Burk linearization of the reaction of hydrolysis of p-NPG (p-nitrophenyl glucopyranoside) in the presence of different concentrations of the peptide inhibitor LKP.

The abscissa shows the concentration of the substrate (in $1/[\text{p-NPG}]$ in $\text{mol}^{-1}$), and the ordinate shows the rate in ($1/\text{Vi}$ in $\mu\text{mol}^{-1} \cdot \text{min}^{-1}$).

The four straight lines represent the following concentrations of inhibitors:
Filled circle: no inhibitor
Empty circle: test in the presence of 5 mM of LKP
Filled triangle: test in the presence of 6 mM of LKP
Empty triangle: test in the presence of 7.5 mM of LKP.
This linearization makes it possible to determine the enzyme constants Km and Vmax by representation of the inverses.

Figure 5:
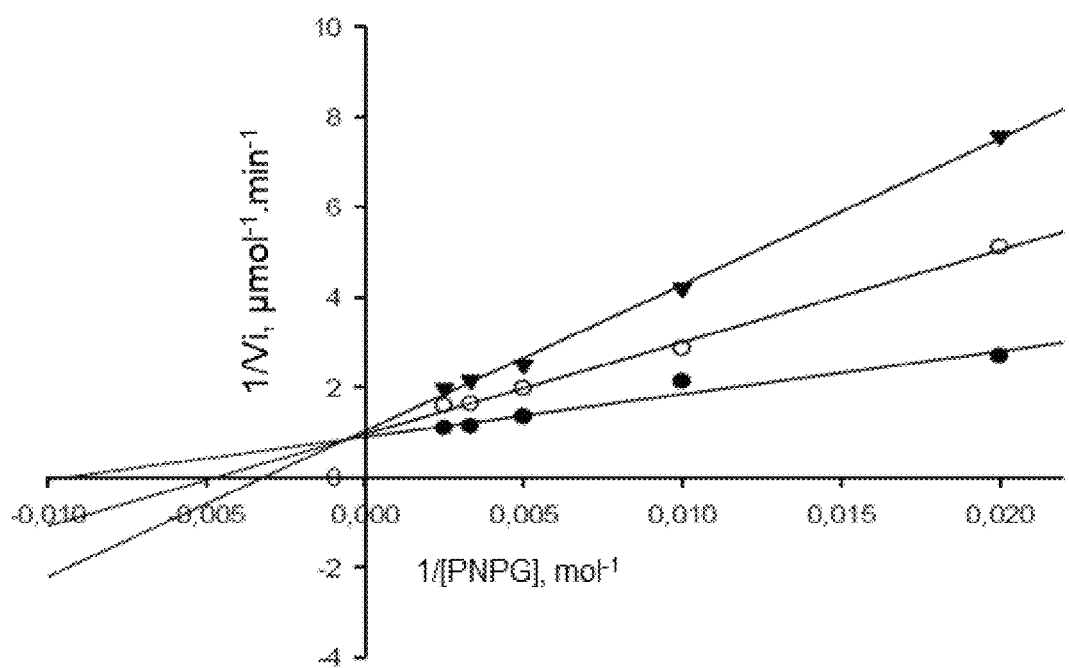

FIG. 5 shows Lineweaver-Burk linearization of the reaction of hydrolysis of p-NPG (p-nitrophenyl glucopyranoside) in the presence of different concentrations of the peptide inhibitor AP.

The abscissa shows the concentration of the substrate (in $1/[\text{p-NPG}]$ in $\mu\text{mol}^{-1}$), and the ordinate shows the rate in ($1/\text{Vi}$ in $\mu\text{mol}^{-1} \cdot \text{min}^{-1}$).

Figure 6:
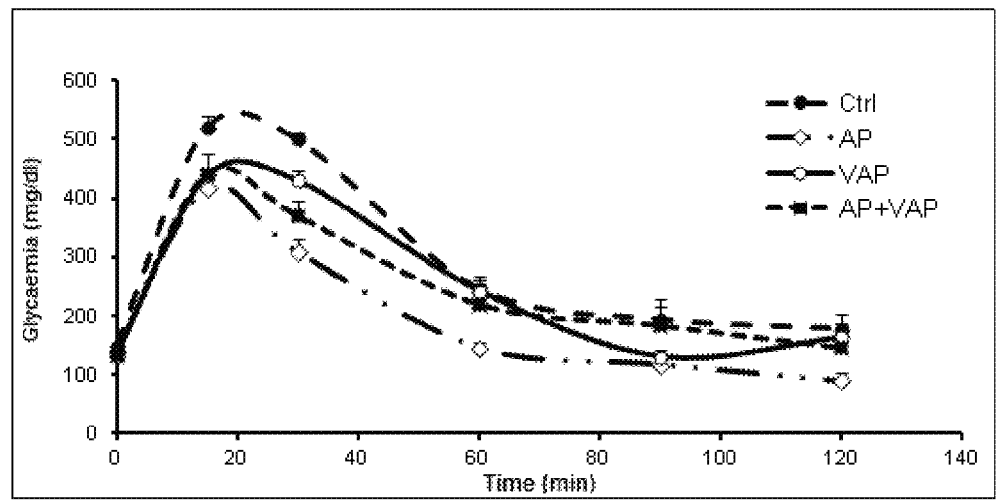

The three straight lines are as follows:
Filled circle: without enzyme
Empty circle: test in the presence of 50 µM of AP
Filled triangle: test in the presence of 100 µM of AP FIG. 6 shows the variation of glycaemia (in raw values, i.e. the total glycaemia) during the test of tolerance to maltose.

The abscissa shows the time (in minutes) and the ordinate shows the glycaemia (mg/dl).

Figure 7:
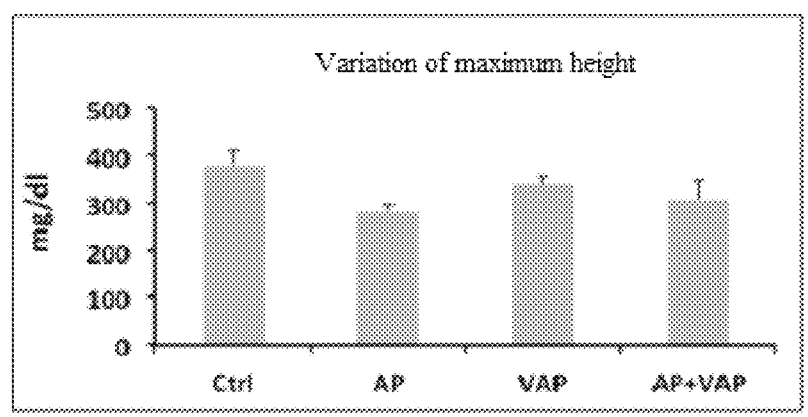

FIG. 7 shows the maximum values of glycaemia subtracted from the resting value from the oral test of tolerance to maltose.

The resting value is 150 mg/dl. The baseline glycaemia (at rest) was measured 5 minutes before the first administration by the gastric route. Taking the control condition as reference (saline solution administered before gavage with maltose), the mean baseline glycaemia was 143±34.2 mg/dl.

The abscissa shows the groups with the different peptides tested and the ordinate shows glycaemia (mg/dl).

The groups with the different peptides tested are as follows:
Ctrl represents the control group
AP represents the group tested with AP peptide
VAP represents the group tested with VAP peptide
AP+VAP represents the group tested with AP+VAP peptide The variation of the maximum height represents $\Delta_{Peak}$, i.e. the maximum total glycaemia minus the glycaemia at rest. More precisely, this represents the maximum variation of glycaemia associated with the experimental condition tested, i.e. the highest value of glycaemia minus the baseline value measured 5 minutes before the first administration by the gastric route.

Figure 8:
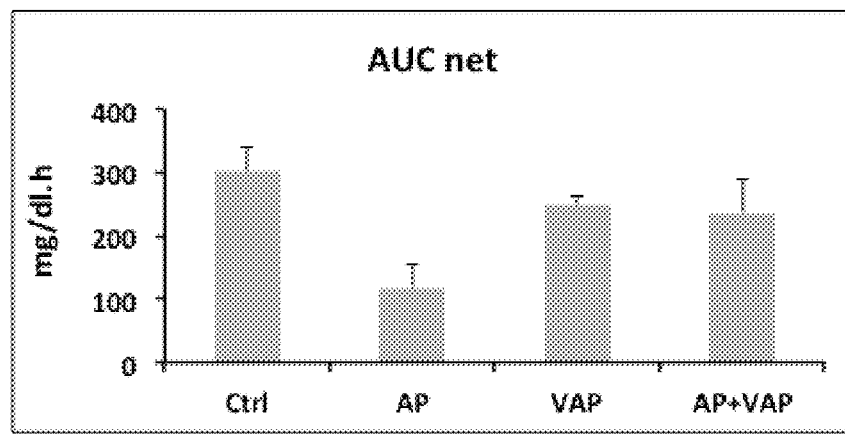

FIG. 8 shows the area under the curve subtracted from the resting value for the results of the four aforementioned groups tested (Ctrl, AP, VAP, AP+VAP).

The abscissa shows the groups with the different peptides tested and the ordinate shows the value of the area (mg/dl·hour=mg/dl·h).

Figure 9:
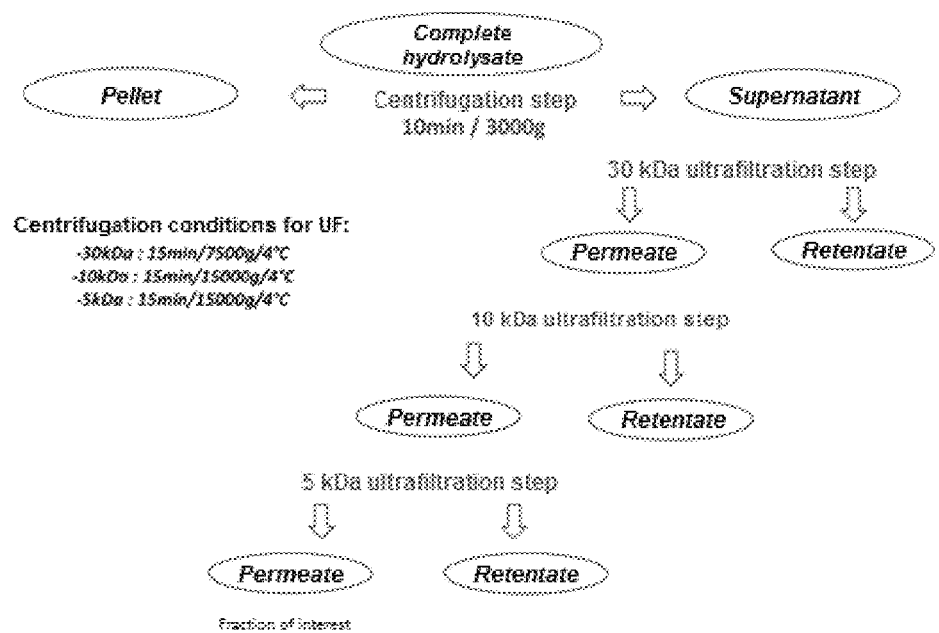

FIG. 9 shows the methodology used for fractionating and concentrating the peptides of low molecular weight resulting from hydrolysis of the proteins from goat whey.

UF denotes ultrafiltration.

30 kDa: 15 min/7500/4° C. means filtration on a 30 KDa filter for 15 minutes at 7500 g at 4° C.

10 kDa: 15 min/15000 g/4° C. means filtration on a 10 KDa filter for 15 minutes at 15000 g at 4° C.

5 kDa: 15 min/15000 g/4° C. means filtration on a 5 KDa filter for 15 minutes at 15000 g at 4° C.

Figure 10:
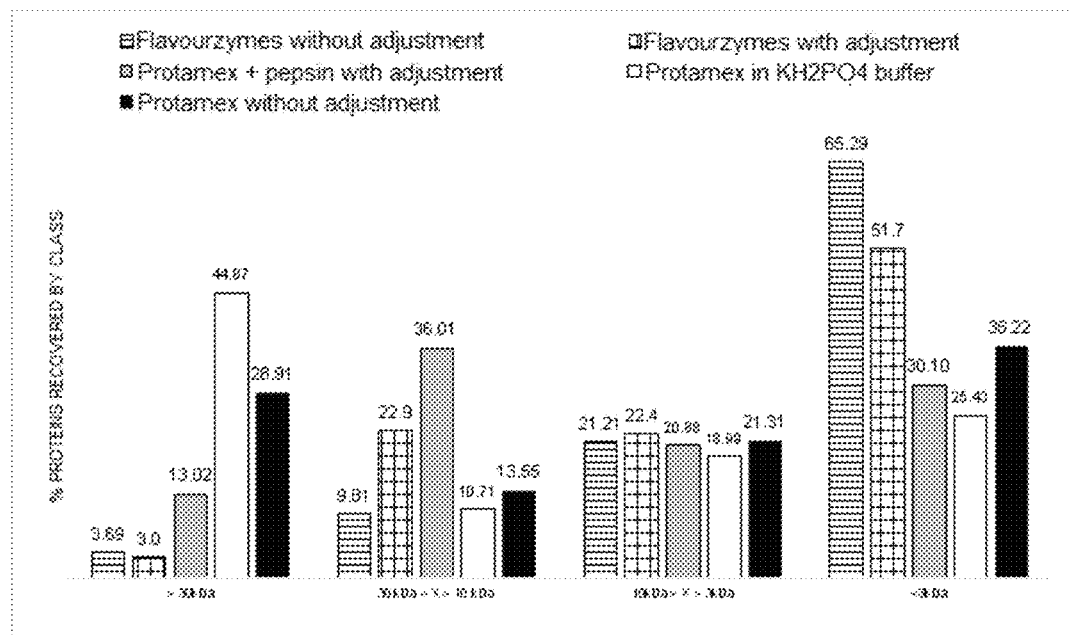

FIG. 10 shows the mass profile of the protein hydrolysates produced with an enzyme (Flavourzymes or Protamex), with or without adjustment of the pH.

The abscissa shows the size of the hydrolysates (more precisely the molecular weight) and the ordinate shows the percentage of proteins recovered by class (i.e. by molecular fraction). The different molecular fractions are as follows:

>30 kDa: proteins and peptides with mass above 30 kDa, 30 kDa>X>10 kDa: proteins and peptides with mass between 30 and 10 kDa, 10 kDa>X>3 kDa: proteins and peptides with mass between 10 and 3 kDa, <3 kDa: proteins and peptides with mass below 3 kDa.

Figure 11:
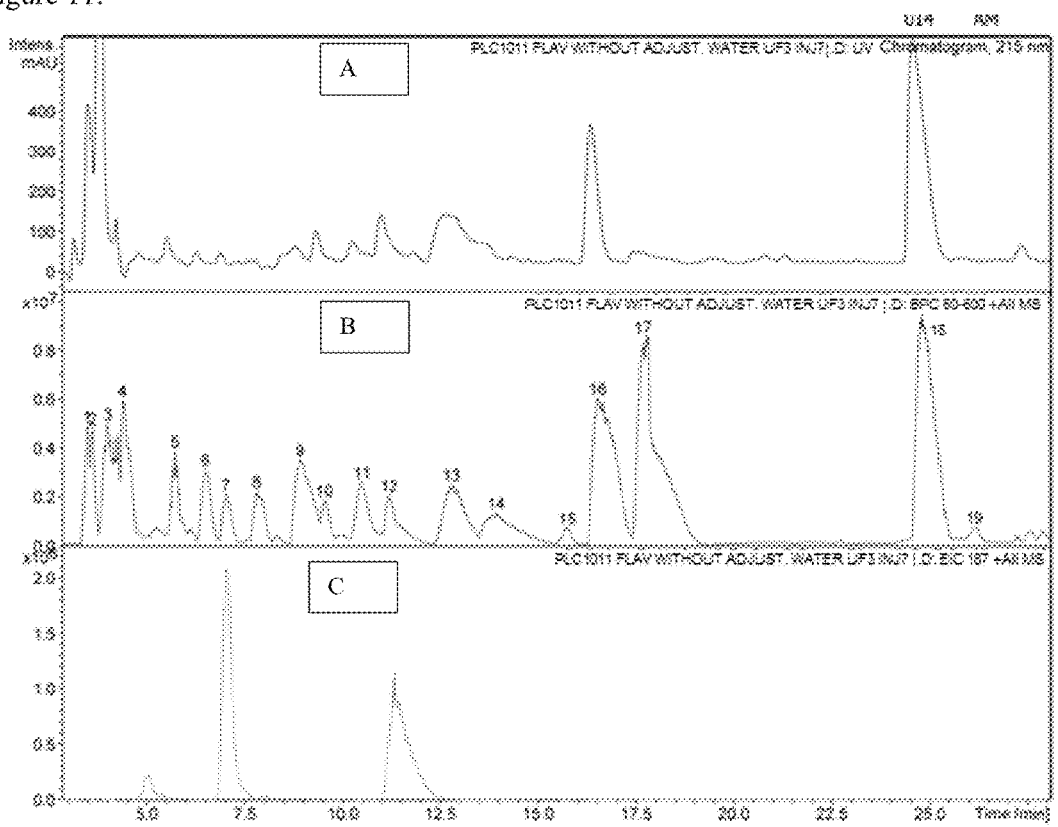

FIG. 11 shows LC-MS analysis (HPLC-MS) on a Waters BEH column, of the hydrolysate from LC by Flavourzymes in ultrapure water.

The abscissa shows the time (in minutes), and the ordinate shows the intensity (in mAU [AU=arbitrary unit]).

Case A shows the UV spectrum, arbitrary units in mAU, for UV at 215 nm;

Case B shows the complete mass spectrum in numbers of ions;

Case C shows the mass spectrum of the ion m/z 187.

EXAMPLES

Example 1: Test of Inhibition In Vitro of the Activity of Alpha-glucosidase in the Presence of Different Synthetic Peptides Material and Methods The test of inhibition of the activity of alpha-glucosidase in the presence of synthetic VW, VY, IY, KY, VY, KW, AP, LKP, GPL, VAP, and AKK peptides was carried out according to the following protocol (based on that described in Kang et al., *Journal of Medicinal Plants Research* 2012, 6: 2850-2856). The synthetic peptides were supplied by GENOSPHERE Biotechnologies.

The alpha-glucosidase used is the recombinant alpha-glucosidase from *Saccharomyces cerevisiae*, which is a maltase.

20 μL of alpha-glucosidase in 0.1 mol/L sodium phosphate buffer (pH 6.8) at a final concentration of 0.2 U/mL was mixed with 8 μL of the sample of peptide or of acarbose (marketed by Bayer AG under the name Glucor) at different concentrations (0.01 to 50 mmol/L). The samples were solubilized beforehand in deionized water containing 10% of DMSO (dimethyl sulphoxide).

Acarbose, a commercial synthetic inhibitor, regarded as the reference inhibitor of alpha-glucosidase, is used here as positive control.

After incubation at 37° C. for 20 minutes, 20 μL of the substrate p-NPG (p-nitrophenyl glucopyranoside) at 2.5 mM (prepared in the same buffer as mentioned above) was added to the mixture in order to start the reaction.

The reaction medium was incubated for 30 minutes at 37° C. and then the reaction was stopped by adding 80 μL of a solution of sodium carbonate ($Na_2CO_3$) at 0.3M.

The quantity of product formed (p-nitrophenyl (p-NP) of yellow colour) was measured by spectrophotometry (absorbance at 410 nm, VersaMax™, Microplate Reader).

The test was carried out in a 96-well microplate.

All the inhibition tests were carried out in triplicate.

The percentage inhibition was calculated from the following equation:

$$\% \text{ inhibition} = \left[1 - \frac{(OD \text{ sample assay} - OD \text{ assay blank})}{(OD \text{ control assay} - OD \text{ control blank})}\right] * 100$$

OD sample assay corresponds to the optical density obtained for the mixture "sample+enzyme+substrate".

OD assay blank corresponds to the optical density obtained for the mixture "sample+buffer".

OD control assay corresponds to the optical density obtained for the mixture "buffer+enzyme+substrate".

OD control blank corresponds to the optical density obtained for the buffer.

Results

Each VW, VY, IY, KY, VY, KW, AP, LKP, GPL, VAP, and AKK peptide was tested according to the protocol described above in the Material & Methods section.

Different concentrations of these peptides were used for determining their $IC_{50}$, i.e. the concentration required for inhibiting 50% of the activity of alpha-glucosidase.

The variation of the percentage inhibition as a function of the concentration of acarbose (positive control) is shown in FIG. 1.

The variation of the percentage inhibition as a function of the concentration of AP peptide and of VAP peptide is shown in FIG. 2 and in FIG. 3 respectively.

The results for the $IC_{50}$ of the peptides as well as of acarbose are shown in Table 1 below:

| Peptide sequence | Inhibitory activity on α-glucosidase ($IC_{50}$) in mM |
|---|---|
| Acarbose | 11.92 ± 1.44 |
| Miglitol | 39 ± 0.96 |
| LKP | 7.11 ± 0.20 |
| GPL | 4.82 ± 0.15 |
| VIY | No inhibition |
| AKK | No inhibition |
| VAP | 0.020 ± 0.0002 |
| AP | 0.0136 ± 0.001 |
| IY | 12.27 ± 0.25 |
| KY | 10.96 ± 0.1 |
| KW | 12.76 ± 0.98 |
| VW | No inhibition |
| VY | 2.7 ± 0.18 |
| IY | 12.26 ± 0.25 |

Certain peptides therefore display inhibition of the activity of α-glucosidase in vitro.

Among these peptides, the AP and VAP peptides have the highest inhibitory activity of the peptides tested, with $IC_{50}$ of 13.64±0.92 μM and 20.01±0.21 μM respectively.

The $IC_{50}$ of the AP peptide is approximately 874 times lower than that of acarbose, the positive control ($IC_{50}$=11920±1444 μM), whereas that of the VAP peptide is approximately 595 times lower.

These results therefore confirm that the VAP, AP, VY, LKP, IY, KY and KW and GPL peptides, which are widely present in the proteins of marine co-products, inhibit α-glucosidase, and in particular maltase.

Nevertheless, the LKP, GPL, IY, KY, KW and VY peptides are weak inhibitors of alpha-glucosidase, relative to the AP and VAP peptides. In fact, the IY, KY and KW peptides have $IC_{50}$ close to that of acarbose, and the LKP, GPL and VY peptides have $IC_{50}$ values approximately 355, 243 and 135 times higher, respectively, relative to those of the AP and VAP peptides.

Example 2: In-vitro Determination of the Inhibition of Alpha-glucosidase by Synthetic Peptides—Test Number 2

Material & Methods

20 µl of α-glucosidase in 0.1M potassium phosphate buffer (pH 6.8) at 1.6 U/ml is mixed with 8 µl of the peptide sample or of the reference inhibitor at different concentrations.

The samples are solubilized beforehand in milliQ water containing 10% DMSO (available from Sigma under reference 472301).

After preincubation at 37° C. for 15 min, 20 µl of the substrate p-NPG at 20 mM in 0.1M potassium phosphate buffer (pH 6.8) is added to the mixture in order to start the reaction.

The reaction medium is incubated for 30 min at 37° C. and then the reaction is stopped by adding 80 µl of a 1M solution of sodium carbonate ($Na_2CO_3$).

The quantity of product formed (p-nitrophenyl) is measured by reading the absorbance at 410 nm using the Fluostar Omega spectrophotometer (BMG Labtech, Germany).

All the inhibition tests are carried out in triplicate.

The enzyme used is recombinant alpha-glucosidase from *S. cerevisiae* (it is a maltase available from Sigma, under reference G0660-750UN).

The substrate used is 4-nitrophenyl α-D-glucopyranoside (p-NPG) (available from Sigma under reference N1377).

The peptides were supplied by Génosphère and have a purity >95%.

The inhibitors used are acarbose (available from Sigma under reference A8980), miglitol (available from Sigma under reference M1574), and voglibose (available from Sigma under reference 50359).

The results for the $IC_{50}$ of the peptides tested and of acarbose, miglitol and voglibose are shown in Table 2 below.

| Reference/Peptide sequence | MW (g/mol) | ($IC_{50}$) in mmol/l | ($IC_{50}$) in mg/ml |
| --- | --- | --- | --- |
| Acarbose | 645.6 | 11.92 ± 1.44 | 7.696 |
| Miglitol | 207.22 | 37.475 ± 0.69 | 7.766 |
| Voglibose | 267.28 | 24.41 ± 0.47 | 0.2673 |
| AP | 186 | 0.0136 ± 0.001⁻ | 0.0025 |
| VAP | 285 | 0.020 ± 0.0002 | 0.0057 |
| SAPLRVY (SEQ ID NO: 3) | 804 | 1.765 ± 0.18 | 1.4191 |
| VAPFPEV (SEQ ID NO: 4) | 757 | 2.68 ± 0.04 | 2.0288 |
| VY | 280 | 2.7 ± 0.18 | 0.7560 |
| AVPYQR (SEQ ID NO: 5) | 732 | 3.19 ± 0.18 | 2.3351 |
| VAPG (SEQ ID NO: 6) | 342 | 4.05 ± 0.09 | 1.3851 |
| VGVAPG (SEQ ID NO: 7) | 498 | 4.59 ± 0.06 | 2.2858 |
| GPL | 285 | 4.82 ± 0.15 | 1.3737 |
| LKP | 356 | 7.11 ± 0.20 | 2.5312 |
| KY | 309 | 10.96 ± 0.1 | 3.3866 |
| IY | 294 | 12.26 ± 0.25 | 3.6044 |
| KW | 332 | 12.76 ± 0.98 | 4.2363 |

Note:
MW denotes Molecular Weight

The results confirm that the AP and VAP peptides strongly inhibit α-glucosidase, relative to the 3 references: acarbose, miglitol and voglibose, known inhibitors of the glucosidases.

Example 3: In-vitro Determination of the Type of Inhibition of the Peptides LKP and AP Based on the initial rates, the Lineweaver-Burk representations for each concentration of inhibitor LKP were shown and the type of inhibition was determined. The synthetic LKP peptide was supplied by GENOSPHERE Biotechnologies.

The results are shown in FIG. 4.

According to the results, inhibition of the degradation of p-NPG by the LKP peptide is of a competitive type: all the straight lines intersect at the point 1/Vmax.

This study demonstrates that LKP peptides have inhibitory activity on pancreatic α-glucosidase.

This study was also carried out with the AP peptide, which was supplied by GENOSPHERE Biotechnologies.

Based on the initial rates, the Lineweaver-Burk representations for each concentration of inhibitor AP were shown and the type of inhibition was determined.

The results are shown in FIG. 5.

According to the results, inhibition of the degradation of p-NPG by the AP peptide is of a competitive type: all the straight lines intersect at the point 1/Vmax.

This study demonstrates that AP peptides have a strong inhibitory activity on pancreatic α-glucosidase.

Example 4: Test of In-vivo Inhibition of the Activity of Alpha-glucosidase in the Presence of Different Synthetic Peptides Material and Methods The inhibitory activity of the AP and VAP peptides and the effect of the AP and VAP peptides on the glycaemic response can be measured in an oral test of tolerance to sucrose and to maltose in vivo in db/db mice.

The mice are 4 weeks of age and each mouse is its own control.

Five oral tests of tolerance to sucrose and/or maltose (4 g/kg) are carried out on each mouse with a minimum interval of 72 h.

The order is determined so as to cancel a potentially confounding effect of a change in body composition of the mice during the 3 study weeks.

The 5 tests are as follows:

A control assay (comprising 0.9% saline solution);
A test with the AP peptide (at a concentration of 500 mg/kg);
A test with the VAP peptide (at a concentration of 500 mg/kg);
A test with the AP peptide (at a concentration of 500 mg/kg) and with the VAP peptide (at a concentration of 500 mg/kg);
A test with acarbose (at a concentration of 10 mg/kg).

The sucrose or maltose and the test products are diluted in 0.9% saline solution, and then administered directly by the gastric route.

Five minutes after administration by the gastric route, a first blood sample will be taken from the tail in order to determine the glycaemia (t=0); then 6 further samples will be taken after 15, 30, 45, 60, 90 and 120 minutes.

The main criterion for evaluation is measurement of the area under the glycaemic curve over a period of 2 hours following administration of sucrose or maltose (AUC, area under the curve, 0-120 minutes, in g*min/L).

The alpha-glucosidase that can be used for the purposes of the aforementioned protocols may for example be recombinant alpha-glucosidase from *Saccharomyces cerevisiae*, which is a maltase.

Example 5: Test of In-Vivo Inhibition of the Activity of Alpha-Glucosidase in the Presence of the Synthetic AP and VAP Peptides The inhibitory activity of the AP and VAP peptides and the effect of the AP and VAP peptides on the glycaemic response can be measured in an oral test of tolerance to maltose in vivo in db/db mice that have a glucose intolerance of genetic origin.

The mice are 4 weeks of age and each mouse is its own control.

A dose of maltose (2 g/kg) was used in order to cause a temporary increase in glycaemia.

The Experimental Protocol

Four (4) oral tests of tolerance to maltose (2 g/kg) were carried out on each mouse with a minimum interval of 48 h. The order was determined so as to cancel a potentially confounding effect of a change in body composition of the mice during the 3 study weeks.

The following 4 tests were carried out in a random order:
  Control (saline solution 0.9%);
  Ingestion of the AP peptide (500 mg/kg);
  Ingestion of the VAP peptide (500 mg/kg);
  Ingestion of the AP (500 mg/kg)+VAP (500 mg/kg) peptides.

The maltose and the test products were administered directly by the oral route (gastric gavage), diluted in 0.9% saline solution.

Experimental Samples

Five (5) minutes before administration by the gastric route, a first blood sample was taken from the tail in order to determine the glycaemia (t=0); then 5 further samples were taken after 15, 30, 60, 90 and 120 minutes.

Criteria for Evaluation
  Main Criterion: The main criterion for evaluation was measurement of the area under the glycaemic curve over the period of 2 hours following administration of maltose (AUC, area under the curve, 0-120 minutes, in mg*h/dl). The smaller the area under the curve, the more effective the peptide used. The area under the curve is more representative of the glycaemic response to oral loading with carbohydrates, as it takes into account not only the maximum level of glycaemia reached, but also the kinetics of the variation of glycaemia over the period of 2 hours following ingestion of carbohydrates.
  Secondary Criteria: The secondary criteria for evaluation were: Cmax glycaemia (maximum value measured during the 120 minutes), ΔCmax glycaemia (ΔCmax glycaemia=Cmax glycaemia—glycaemia value at t0=150), AUCnet (AUC calculated from the glycaemia values subtracted from the value at t0). The AUC (area under the curve) was estimated by the trapezium method. For AUCnet, the baseline glycaemia value multiplied by the measurement time (2 h) was subtracted from the previously calculated AUC.

The variation of glycaemia during the test of tolerance to maltose is shown in FIG. 6. It shows the gross values (i.e. the value of the direct dosage as opposed to the "net" value, for which the resting value is subtracted). The test was carried out with four groups of 8 mice, and the curve was constructed with the mean value of the results.

The AP and VAP peptides, used alone or in combination, therefore make it possible to lower the glycaemia of the mice tested.

The maximum glycaemia values subtracted from the resting value during the oral test of tolerance to maltose are shown in FIG. 7. For example, the value for AP is approximately 280 mg/dl (430−150=280, i.e. the maximum value minus the resting value measured 5 minutes before gavage. This can provide a more direct demonstration of the impact of the experimental conditions, independently of the baseline glycaemia value, which may display some variability).

These values demonstrate a significant effect of the treatment with the AP peptide on the maximum glycaemia value obtained during a test of tolerance to maltose.

The significant effect of the AP peptide is confirmed by the results for AUC, which are shown in FIG. 8.

In fact, treatment with the AP peptide shows a beneficial effect on the glucose AUC during the oral test of tolerance to maltose.

Example 6: Production of a Whey Protein Hydrolysate from Goat's Milk with Adjustment of the pH Source of the Proteins
Whey protein concentrate (WPC) isolated from raw goat's milk (80% of proteins).
Enzymes Used
Protamex (EC Number 3.4.21.14):
This is a registered trademark of Novozymes Corp. The enzyme is available from Sigma under reference P0029.
It is a mixture of proteases (Alcalase from *Bacillus licheniformis* and Neutrase from *Bacillus amyloliquefaciens*).
The activity of the enzyme is 1.5 U/g of solid.
Batch number: 119K1454V
Flavourzymes:
This is a registered trademark of Novozymes Corp. The enzyme is available from Sigma under reference P6110.
It is a protease/peptidase mixture from *Aspergillus oryzae*.
The activity of the enzyme is 500 U/g.
Batch number: SLBJ3967U
Proline Specific Endoprotease:
The enzyme is marketed by DSM under the trademark Brewers clarex (the enzyme is isolated from *Aspergillus niger*). The enzyme is available from Sigma under reference E1411.
It is a proline specific of the endopeptidases of *Flavobacterium* sp. More particularly, the enzyme specifically hydrolyses the C-terminal bonds of the prolines of the peptide sequence.
The activity of the enzyme is 5 U/mg.
Batch number: SLBD9700V
Pepsin:
The enzyme is available from Sigma under reference P7000.
It is a pepsin from pig gastric mucosa.
The activity of the enzyme is 250 U/mg of solid.
Batch number: SLBH3879V The hydrolyses are carried out on a pH-Stat 718 Stat Titrino Station from Metrohm that allows adjustment of temperature and pH, and monitoring of the hydrolyses. This station is also equipped with a 728 Stirrer cell from Metrohm, making stirring possible at 200 to 1900 r.p.m.

The solution of whey proteins from goat's milk corresponds to 5% of dry matter in water (which corresponds, in the example, to 1500 mg in 30 mL of ultrapure water).

A step of denaturation by heating the solution at 80° C. for 10 minutes is applied before hydrolysis.

In order to stop the hydrolysis reaction, the solution temperature is raised to 90° C. for 15 minutes in order to denature the enzymes still present in the medium.

The hydrolysate is then divided into aliquots and stored at −20° C. before purification and analysis.

1. The Case of Hydrolysis by a Single Enzyme: Flavourzymes

The solution is heated to a temperature of 50° C., and the pH is set at 8.0 by adding 6M NaOH. Hydrolysis begins on adding 750 µL of Flavourzymes (750 µL/30 mL/1500 mg of WPC, 5% v/w). The pH is maintained at 8 by adding 0.1M NaOH.

2. The Case of Double Hydrolysis: Protamex and Pepsin

The solution is heated to a temperature of 50° C., and the pH is set at 8.0 by adding 6M NaOH. Hydrolysis begins on adding 60 mg of Protamex (60 mg/30 mL/1500 mg of WPC, 4% w/w). The pH is maintained at 8 by adding 0.1M NaOH.

When hydrolysis has been stopped, the pH is lowered to a value of 2 before adding 30 mg of pepsin (30 mg/30 mL/1500 mg of WPC, 2% w/w). This time the pH is adjusted by adding 0.1M HCl.

Example 7: Production of a Hydrolysate of Whey Proteins from Goat's Milk without Adjustment of the pH Source of the Proteins
Whey protein concentrate (WPC) isolated from raw goat's milk (80% of proteins).
Enzymes Used
Protamex (available from Sigma under reference P0029) (60 mg/30 mL/1500 mg of WPC, 4% w/w) or Flavourzymes (available from Sigma under reference P6110) (750 µL/30 mL/1500 mg of WPC, 5% v/w).

The hydrolyses are carried out either in ultrapure water or in a potassium phosphate buffer, pH 8.0 and molarity of 50 mM.

The solution of whey proteins from goat's milk corresponds to 5% of dry matter in buffer or in ultrapure water.

A step of denaturation by heating the solution at 80° C. for 10 minutes is applied before hydrolysis.

Hydrolysis is then carried out on Radley Tech Carousel 6 supports (these are conventional reaction stations made by Radley), controlling the internal temperature of the media at 50° C. and providing stirring at 600 rpm.

In order to stop the hydrolysis reaction, after 6 h, the solution temperature is raised to 90° C. for 15 minutes in order to denature the enzymes still present in the medium.

The hydrolysate is then divided into aliquots and stored at −20° C. before fractionation and analysis.

Example 8: Fractionation of the Whey Protein Hydrolysates from Goat's Milk

The hydrolysates previously produced (Examples 6 and 7) are subjected to a series of fractionations allowing concentration of the targeted low molecular weight peptides.

A first centrifugation step has the aim of removing the proteins of high molecular weights that are not hydrolysed, which are contained in the pellet.

A series of successive ultrafiltrations with a cut-off of from 30 to 3 kDa is then applied to the supernatant, which contains the hydrolysed proteins. The ultrafiltrations are carried out with centrifugation units of reference Amicon Ultra from Millipore (2 mL with cut-offs of 30, 10 and 3 kDa). The centrifuge used is a Fisher Bioblock Scientific Sigma 3-18K-3-16K model.

The methodology used is shown in FIG. 9.

At each intermediate stage, a proportion of the permeates, retentates, pellets and supernatants is divided into aliquots and then lyophilized.

Two fractions are obtained as a result of centrifugation: the pellet (solid, at the bottom of the tube), and the supernatant (liquid fraction).

Ultrafiltration results in a retentate and a permeate being obtained.

A retentate is a term used for membrane separation techniques, describing the particles retained during filtration. The opposite of the retentate is the permeate.

The retentate is also called non-filtrate.

A permeate is the liquid from which the peptides have been removed with the aid of a membrane. The permeate is also called the filtrate.

The samples are then stored at −20° C. before analysis.

Example 9: Determination of the Mass Profile of the Whey Protein Hydrolysates from Goat's Milk At each stage of fractionation, for the hydrolysates previously produced (Examples 6 and 7), the remaining quantity of proteins was determined by the BCA method (BiCinchoninic acid Assay). This quantification makes it possible to determine the mass profile of the protein hydrolysates.
Reagents
The reagents used are bicinchoninic acid (available from Sigma under reference B9643), copper(II) sulphate (available from Sigma under reference C2284), BSA (bovine serum albumin) (available from Sigma under reference A7888).
Protocol
In a 96-well microplate, add 200 µL of BCA reagent, corresponding to a bicinchoninic acid: copper(II) sulphate mixture at a ratio of 25:0.5 (V:V), to 25 µL of the test sample.

In order to determine the concentration, a standard range of BSA is prepared and tested in concentrations between 0 and 0.6 mg/mL. Once the sample has been added, the reaction is carried out for 30 minutes at 37° C., and then the OD (optical density) is read at 526 nm.

The results are shown in FIG. 10.

The use of Flavourzymes in place of Protamex makes it possible to generate a higher proportion of peptides below 3 kDa.

More particularly, the use of Flavourzymes without adjustment of the pH is the method of hydrolysis that makes it possible to obtain, after fractionation, the largest quantity of peptides of targeted molecular weights, below 3 kDa.

In contrast, the use of a buffer and the Protamex enzyme only makes it possible to generate 25% of peptides below 3 kDa. This protocol therefore does not seem suitable for releasing peptides of low molecular weight.

Example 10: Identification of the AP Peptide in the Whey Protein Hydrolysates from Goat's Milk 1. Characteristics of the Synthetic AP Peptide by Analysis by HPLC-MS The identification is performed with an Agilent analytical HPLC (1100 LC), using the C18 Prontosil column (250×4 mm, 2.0 µm) or a Waters Xbridge BEH130 C18 column (5 µm, 4.6×250 mm) and using double detection: UV at 215 nm and mass spectrometry (MS-ion trap, with ionization of the electrospray type in positive scan mode).

The MS conditions are: scan from 60 to 600 m/z; target mass (m/z) of 187, temperature of the source 300° C. with a flow rate of 10 L/min of nitrogen. The gradient uses two solvents, solvent A consisting of milliQ water with 0.1% of TFA (trifluoroacetic acid) and solvent B consisting of acetonitrile with 0.1% of TFA, and begins at 1% of B to reach 30% after 55 min, then 50% at 60 min and finally 100% at 65 min, before returning to 1% at 75 min.

The AP peptide from Genosphère (of purity above 95%) is analysed in order to obtain the reference mass spectrum as well as the retention time with respect to UV and mass.

When separation is carried out on a C18 Prontosil column, the pure AP peptide has a retention time of 3.4 min and two characteristic m/z peaks on its mass spectrum, 187 and 116. The 187 fragment corresponds to MH+, 209 to MNa+ and 116 to fragmentation of the peptide to C-terminal proline.

When separation is carried out on a C18 Waters BEH column, the pure AP peptide has a retention time of 10.5 min and two characteristic m/z peaks on its mass spectrum, 187 and 116. The 187 fragment corresponds to MH+, 209 to MNa+, 373 to 2MH+, 395 to 2MNa+ and 116 to fragmentation of the peptide to C-terminal proline.

2. Identification of the AP Peptide in a Hydrolysate Obtained with Flavourzymes

The hydrolysates from examples 6.1 and 7 produced with the Flavourzymes enzyme with and without adjustment of the pH are analysed using HPLC-MS on the C18 Waters BEH column, where the AP peptide has a retention time close to 10.5 min. FIG. 11 shows the UV and mass spectrum as well as the extract ion chromatogram for a target mass/charge of 187 (MH+ of AP) of the hydrolysates.

Based on the EIC187, a predominant peak having a retention time corresponding to the standard AP peptide (i.e. the molecule of pure AP from chemical synthesis) of the order of 11 minutes, is found during hydrolysis by Flavourzymes, with and without adjustment of the pH. Analysis of the mass spectrum of this peak reveals the specific markers of the AP peptide (m/z=187; 116; 373), giving assurance of its presence in these hydrolysates. The second peak present in the EIC, but having a retention time of the order of 7 minutes, corresponding to the standard PA peptide (i.e. the molecule of pure PA from chemical synthesis). Analysis of the mass spectrum of this peak reveals the specific markers of the PA peptide (m/z=187; 90; 373).

There are two peptides with a mass of 187, the required AP peptide but also the PA peptide.

These analyses confirm that the hydrolysis protocol using Flavourzymes with or without adjustment of the pH makes it possible to release the AP peptide from goat whey protein concentrate.

3. Identification of the AP Peptide in a Hydrolysate Obtained with the Protamex/Pepsin Pair The hydrolysate from Example 6.2 is then analysed using HPLC-MS on the Prontosil column, where the AP peptide has a retention time of the order of 3.5 min. The extract ion chromatogram for a target mass/charge of 187 (MH+ of AP) after the first step of hydrolysis by Protamex and then after the second phase of hydrolysis by pepsin is determined.

After hydrolysis by Protamex, the predominant peak comprising m/z of 187 is found for a retention time of the order of 16 minutes. This retention time corresponds to a larger peptide. After the action of pepsin, the AP peptide of mass 187 appears in the hydrolysate at 3.5 min.

These analyses confirm that the hydrolysis protocol using two enzyme preparations, Protamex and then pepsin, makes it possible to release the AP peptide from goat whey protein concentrate.

Example 11: Choice of Proteins for Producing a Hydrolysate Containing the AP Peptide All proteins having the AP sequence (comprising or constituted by at least 0.05% to <5% or of at least 5% of AP units) can be used for the invention, and in particular the proteins with the following sequences:
1) Milk Proteins (Cow, Mare, Ewe)
a/ Beta-Lactoglobulin (Cow's Milk)
Uniprot Data: P02754
1 AP, 178 AA, 19883 Da

```
                                            (SEQ ID NO: 8)
MKCLLLALAL TCGAQALIVT QTMKGLDIQK VAGTWYSLAM

AASDISLLDA QSAPLRVYVE ELKPTPEGDL EILLQKWENG

ECAQKKIIAE KTKIPAVFKI DALNENKVLV LDTDYKKYLL

FCMENSAEPE QSLACQCLVR TPEVDDEALE KFDKALKALP

MHIRLSFNPT QLEEQCHI
``` b/ Alpha-S1-Casein (Cow's Milk)
Uniprot Data: P02754
2 AP including 1 VAP, 214 AA, 24529 Da

```
                                            (SEQ ID NO: 9)
MKLLILTCLV AVALARPKHP IKHQGLPQEV LNENLLRFFV

APFPEVFGKE KVNELSKDIG SESTEDQAME DIKQMEAESI

SSSEEIVPNS VEQKHIQKED VPSERYLGYL EQLLRLKKYK

VPQLEIVPNS AEERLHSMKE GIHAQQKEPM IGVNQELAYF

YPELFRQFYQ LDAYPSGAWY YVPLGTQYTD APSFSDIPNP

IGSENSEKTT MPLW
``` c/ Beta-Casein (Cow's Milk)
Uniprot Data: P02666
1 AP, 214 AA, 24529 Da

```
                                           (SEQ ID NO: 10)
MKVLILACLV ALALARELEE LNVPGEIVES LSSSEESITR

INKKIEKFQS EEQQQTEDEL QDKIHPFAQT QSLVYPFPGP

IPNSLPQNIP PLTQTPVVVP PFLQPEVMGV SKVKEAMAPK

HKEMPFPKYP VEPFTESQSL TLTDVENLHL PLPLLQSWMH

QPHQPLPPTV MFPPQSVLSL SQSKVLPVPQ KAVPYPQRDM

PIQAFLLYQE PVLGPVRGPF PIIV
``` d/ Lactoferrin (Cow's Milk)
Uniprot Data: P24627
5 AP including 1 VAP, 708 AA, 78056 Da

```
                                           (SEQ ID NO: 11)
MKLFVPALLS LGALGLCLAA PRKNVRWCTI SQPEWFKCRR

WQWRMKKLGA PSITCVRRAF ALECIRAIAE KKADAVTLDG
```

-continued

```
GMVFEAGRDP YKLRPVAAEI YGTKESPQTH YYAVAVVKKG

SNFQLDQLQG RKSCHTGLGR SAGWIIPMGI LRPYLSWTES

LEPLQGAVAK FFSASCVPCI DRQAYPNLCQ LCKGEGENQC

ACSSREPYFG YSGAFKCLQD GAGDVAFVKE TTVFENLPEK

ADRDQYELLC LNNSRAPVDA FKECHLAQVP SHAVVARSVD

GKEDLIWKLL SKAQEKFGKN KSRSFQLFGS PPGQRDLLFK

DSALGFLRIP SKVDSALYLG SRYLTTLKNL RETAEEVKAR

YTRVVWCAVG PEEQKKCQQW SQQSGQNVTC ATASTTDDCI

VLVLKGEADA LNLDGGYIYT AGKCGLVPVL AENRKSSKHS

SLDCVLRPTE GYLAVAVVKK ANEGLTWNSL KDKKSCHTAV

DRTAGWNIPM GLIVNQTGSC AFDEFFSQSC APGADPKSRL

CALKAGDDQG LDKCVPNSKE KYYGYTGAFR CLAEDVGDVA

FVKNDTVWEN TNGESTADWA KNLNREDFRL LCLDGTRKPV

TEAQSCHLAV APNHAVVSRS DRAAHVKQVL LHQQALFGKN

GKNCPDKFCL FKSETKNLLF NDNTECLAKL GGRPTYEEYL

GTEYVTAIAN LKKCSTSPLL EACAFLTR
```

2) Fibrous Proteins (Elastin, Collagen, Actin)
a/ Actin (Atlantic Salmon)
Uniprot Data: B5XFZ3
4 AP including 1 VAP, 376 AA, 41584 Da

```
                                      (SEQ ID NO: 12)
MVEDEVAALV IDNGSGMCKS GFAGDDAPRA VFPSIVGRPR

HVGIMVGMGQ KDSYVGDEAQ SKRGILSLKY PIDHGIVTNW

DDMEKIWHHT FYNELRVAPE EHPVLLTEAP LNPKNNREKM

TQIMFETFNS PAMYVAIQAV LSLYASGRTT GIVLDSGDGV

THTVPIYEGY ALPHAVLRLD LAGRDLTDYL MKVLTERGYS

FTTTAEREIV RDVKEKLCYV ALDYTNELAV AGSSSSLEKS

YELPDGQVIT IGSERFRCPE ALFQPALIGM EAVGIHETAY

NSIMKCDVDI RKDLYANTVL SGGSTMFSGI ADRMQKEVSA

LAPTTMKIKI ISPPERKYSV WIGGSILASL STFQQMWISK

MEYDESGPAI VHRKCF
``` b/ Collagen Alpha2 (I) (*Oncorhynchus Keta*, Chum Salmon)
Uniprot Data: Q8UUJ4
8 AP, 1352 AA, 126443 Da

```
                                      (SEQ ID NO: 13)
MLSFVDNRIL LLLAVTSLLA SCQSGPRGAK GPRGDRGPQG

PNGRDGKAGL PGVAGPPGPP GLGGNFAAQF DGGKGSDPGP

GPMGLMGSRG PNGPPGSPGP QGFTGHAGEP GEPGQTGSIG

ARGPTGSAGK PGEDGNNGRP GKPGDRGGPG TQGARGFPGT

PGLPGMKGHR GYNGLDGRKG ESGTAGAKGE TGAHGANGTP

GPAGSRGLNG ERGRAGPAGP AGARGADGST GPAGPAGPLG

AAGPPGFPGA PGPKGEIGGA GSNGPSGPQG GRGEPGINGA

VGPVGPVGNP GNNGINGAKG AAGLPGVAGA PGFPGPRGGP

GPQGPQGSTG ARGLGGDPGP SGQKGDSGAK GEPGHSGVQG

AAGPAGEEGK RGSTGEAGAT GPAGLRGARG GAGTRGLPGL

EGRGGPIGMP GARGATGPAG IRGAPGDAGR AGESGLTGAR

GLPGNSGQGG PPGKEGPSGA AGLDGRTGPP GPTGPRGQPG

NIGFPGPKGP GGEAGKGGDK GPTGATGLRG GPGADGNNGA

PGPAGVVGNA GEKGEQGPSG APGFQGLPGP AGPAGEAGKA

GNQGMPGDQG LPGPAGVKGE RGNSGPAGSA GSQGAIGARG

PAGTPGPDGG KGEPGSVGIV GAAGHQGPGG MPGERGAGGT

PGPKGEKGEG GHRGLEGNMG RDGARGAAGP SGPPGPSGAN

GEKGESGSFG PAGPAGLRGP SGERGEGGPA GPPGFAGPPG

SDGQSGPRGE KGPAGGKGDV GPAGPAGPSG QSGPSGASGP

AGPPGGRGDA GPSGLTGFPG AAGRVGGPGP AGISGPPGSA

GPAGKDGPRG LRGDAGPGGP QGEQGVVGPA GIAGDKGPSG

EGGPPGAPGT AGPQGVLGPS GFVGLPGSRG DKGLPGGPGA

VGEPGRLGPA GASGPRGPSG NIGMPGMTGT QGEAGREGNS

GNDGPPGRPG AAGFKGDRGE PGSPGALGSS GQPGPNGPAG

SAGRPGNRGE SGPTGNGGPV GAAGARGAPG PAGPRGEKGG

AGEKGDRGMK GLRGHGGLQG MPGPNGPSGE TGSAGITGPA

GPRGPAGPHG PPGKDGRAGG HGAIGPVGHR GPPGHLGPAG

PPGSPGLPGP AGPAGGGYDQ SGGYDEYRAD QPSLRAKDYE

VDATIKSLNS QIENLLTPEG SKKNPARTCR DIRLSHPEWS

SGFYWIGPNQ GCIADAIKAY CDFSTGHTCI HPHPESIARK

NWYRSSENKK HVWFGETING GTEFAYNDET LSPQSMATQL

AFMRLLANQA TQNITYHCKN SVAYMDGENG NLKKAVLLQG

SNDVELRAEG NSRFTFNVLE DGCTRHTGQW SKTVIEYRTN

KPSRLPILDI APLDIGEADQ EFGLDIGPVC FK
``` c/ The Collagen Alpha1 (II) Sequence (Bovine)
Uniprot Data: P02459
21 AP, 1487 AA, 141828 Da

```
                                      (SEQ ID NO: 14)
QMAGGFDEK AGGAQMGVMQ GPMGPMGPRG PPGPAGAPGP

QGFQGNPGEP GEPGVSGPMGPRGPPGPPGK PGDDGEAGKP

GKSGERGPPG PQGARGFPGT PGLPGVKGHR

GYPGLDGAKGEAGAPGVKGE SGSPGENGSP GPMGPRGLPG

ERGRTGPAGA AGARGNDGQP GPAGPPGVGPAGGPGFPGA

PGAKGEAGPT GARGPEGAQG PRGEPGTPGS PGPAGAAGNP

GTDGIPGAKGSAGAPGIAGA PGFPGPRGPP GPQGATGPLG

PKGQTGEPGI AGFKGEQGPK GEPGPAGPQG APGPAGEEGK

RGARGEPGGA GPAGPPGERG APGNRGFPGQ DGLAGPKGAP

GERGPSGLAGPKGANGDPGR PGEPGLPGAR GLTGRPGDAG
```

-continued

PQGKVGPSGA PGEDGRPGPP GPQGARGQPGVMGFPGPKGA

NGEPGKAGEK GLPGAPGLRG LPGKDGETGA AGPPGPAGPA

GERGEQGAPGPSGFGGLPGP PGPPGEGGKP GDGGVPGEAG

APGLVGPRGE RGFPGERGSPGSQGLQGARGLPGTPGTDGP

KGAAGPAGPP GAQGPPGLQG MPGERGAAGI AGPKGDRGDV

GEKGPEGAPG KDGGRGLTGP IGPPGPAGAN GEKGEVGPPG

PAGTAGARGA PGERGETGPP GPAGFAGPPGADGQPGAKGE

QGEAGQKGDA GAPGPQGPSG APGPQGPTGV

TGPKGARGAQGPPGATGFPGAAGRVGPPGS NGNPGPPGPP

GPSGKDGPKG ARGDSGPPGR AGDPGLQGPA

GPPGEKGEPGDDGPSGPDGP PGPQGLAGQR GIVGLPGQRG

ERGFPGLPGP SGEPGKQGAP GASGDRGPPGPVGPPGLTGP

AGEPGREGSP GADGPPGRDG AAGVKGDRGE TGAVGAPGAP

GPPGSPGPAG PIGKQGDRGE AGAQGPMGPA GPAGARGMPG

PQGPRGDKGE TGEAGERGLK GHRGFTGLQGLPGPPGPSGD

QGASGPAGPS GPRGPPGPVG PSGKDGANGI PGPIGPPGPR

GRSGETGPAGPPGNPGPPGP PGPPGPGIDM SAFAGLGQRE

KGPDPLQYMR ADEAAGNLRQ HDAEVDATLKSLNNQIESLR

SPEGSRKNPA RTCRDLKLCH PEWKSGDYWI DPNQGCTLDA

MKVFCNMETGETCVYPNPAS VPKKNWWSSK SKDKKHIWFG

ETINGGFHFS YGDDNLAPNT ANVQMTFLRL LSTEGSQNIT

YHCKNSIAYL DEAAGNLKKA LLIQGSNDVE IRAEGNSRFT

YTVLKDGCTKHTGKWGKTMI EYRSQKTSRL PIIDIAPMDI

GGPEQEFGVD IGPVCFL d/ Elastin (Bovine)
Uniprot Data: F1NOH9
9 AP of which 2 VAP, 805 AA, 72317 Da (SEQ ID NO: 15)
MAGLTAAARR PGVLLLLLCI LQPSQPGGVP GAVPGGVPGG

VFFPGAGLGG LGVGALGPGV KPAKPGVGGL AGPGLGAGLG

ALPGAFPGAL VPGGPAGAAA AYKAAAKAGA AGLGVGGIGG

VGGLGVSTGA VVPQLGAGVG AGVKPGKVPG VGLPGVYPGG

VLPGAGARFP GIGVLPGVPT GAGVKPKAPG GGGAFAGIPG

VGPFGGQQPG VPLGYPIKAP KLPGGYGLPY STGKLPYGFG

PGGVAGAAGK AGYPTGTGVG PQAAAAAAKA AAKLGAGGAG

VLPGVGVGGA GIPGAPGAIP GIGGIAGVGA PDAAAAAAAA

AKAAKFGAAG GFPGVGVPGV GVPGVGVPGV GVPGVGVPGV

GVPGVGVPGV GVPGVGVPGV GVPGVGVPGA VSPAAAAKAA

AKAAKFGARG GVGVGGIPTF GVGPGGFPGI GDAAAAQAAA

AAKAAKIGAG GVGALGGLVP GAPGAIPGVP GVGGVPGVGI

PAAAAAAKAA KAAQFGLGPG VGVAPGVGVV PGVGVVPGVG

-continued

VAPGIGLGPG GVIGAGVPAA AKSAAKAAAK AQFRAAAGLP

AGVPGLGVGV GVPGLGVGVG VPGLGVGAGV PGLGAVPGTL

AAAKAAKFGP GGVGALGGVG DLGGAGIPGG VAGVGPAAAA

AAAKAAVQLV PKHRNPHAGL GHTISWPPWP PFPRPIAVPY

VRRLPPPPYW EQPSCSCGIH PPICPSVRPS LSWFGRPAPL

AGWAPPPSTW LTCHGSLGPA STPSHTPLRR GPEPLGVKSC

TSWGRRNLRP NLDLPPRSTV SPSPPRATVL QSISPPPRPS

LCVSL

3) Egg Proteins
a/ Ovotransferrin (Hen's Egg)
Uniprot Data: P02789
5 AP, 705 AA, 75828 Da (SEQ ID NO: 16)
MKLILCTVLS LGIAAVCFAA PPKSVIRWCT ISSPEEKKCN

NLRDLTQQER ISLTCVQKAT YLDCIKAIAN NEADAISLDG

GQAFEAGLAP YKLKPIAAEV YEHTEGSTTS YYAVAVVKKG

TEFTVNDLQG KTSCHTGLGR SAGWNIPIGT LLHRGAIEWE

GIESGSVEQA VAKFFSASCV PGATIEQKLC RQCKGDPKTK

CARNAPYSGY SGAFHCLKDG KGDVAFVKHT TVNENAPDQK

DEYELLCLDG SRQPVDNYKT CNWARVAAHA VVARDDNKVE

DIWSFLSKAQ SDFGVDTKSD FHLFGPPGKK DPVLKDLLFK

DSAIMLKRVP SLMDSQLYLG FEYYSAIQSM RKDQLTPSPR

ENRIQWCAVG KDEKSKCDRW SVVSNGDVEC TVVDETKDCI

IKIMKGEADA VALDGGLVYT AGVCGLVPVM AERYDDESQC

SKTDERPASY FAVAVARKDS NVNWNNLKGK KSCHTAVGRT

AGWVIPMGLI HNRTGTCNFD EYFSEGCAPG SPPNSRLCQL

CQGSGGIPPE KCVASSHEKY FGYTGALRCL VEKGDVAFIQ

HSTVEENTGG KNKADWAKNL QMDDFELLCT DGRRANVMDY

RECNLAEVPT HAVVVRPEKA NKIRDLLERQ EKRFGVNGSE

KSKFMMFESQ NKDLLFKDLT KCLFKVREGT TYKEFLGDKF

YTVISSLKTC NPSDILQMCS FLEGK

4) Vegetable Proteins
a/ Legumin A (Pisum sativum, Pea Proteins)
Uniprot Data: P02857
1 AP, 517 AA, 58805 Da (SEQ ID NO: 17)
MAKLLALSLS FCFLLLGGCF ALREQPQQNE CQLERLDALE

PDNRIESEGG LIETWNPNNK QFRCAGVALS RATLQRNALR

RPYYSNAPQE IFIQQGNGYF GMVFPGCPET FEEPQESEQG

EGRRYRDRHQ KVNRFREGDI IAVPTGIVFW MYNDQDTPVI

AVSLTDIRSS NNQLDQMPRR FYLAGNHEQE FLQYQHQQGG

KQEQENEGNN IFSGFKRDYL EDAFNVNRHI VDRLQGRNED

EEKGAIVKVK GGLSIISPPE KQARHQRGSR QEEDEDEEKQ

```
PRHQRGSRQE EEEDEDEERQ PRHQRRRGEE EEEDKKERGG

SQKGKSRRQG DNGLEETVCT AKLRLNIGPS SSPDIYNPEA

GRIKTVTSLD LPVLRWLKLS AEHGSLHKNA MFVPHYNLNA

NSIIYALKGR ARLQVVNCNG NTVFDGELEA GRALTVPQNY

AVAAKSLSDR FSYVAFKTND RAGIARLAGT SSVINNLPLD

VVAATFNLQR NEARQLKSNN PFKFLVPARE SENRASA
```

Example 12: Production of a Hydrolysate of Pea Proteins, Fish Gelatin and Bovine Gelatin by Flavourzymes Source of the Proteins Pea proteins (available from Nutralis from de Roquette), fish gelatin (available from Sigma), bovine gelatin (available from Sigma).

Enzymes Used

Flavourzymes (available from Sigma under reference P6110) (750 µL/30 mL/1500 mg of WPC, 5% v/w).

A step of denaturation by heating a solution of proteins (5% of dry matter in ultrapure water) at 80° C. for 10 minutes is applied before hydrolysis.

Enzymatic hydrolysis by Flavourzymes is then carried out on Radley Tech Carrousel 6 supports, controlling the internal temperature of the media at 50° C. and allowing stirring at 600 rpm.

In order to stop the reaction after 6 h, the solution temperature is raised to 90° C. for 15 minutes in order to denature the enzymes still present in the medium. The hydrolysate is then divided into aliquots and stored at −20° C. before fractionation and analysis.

The hydrolysates produced by the Flavourzymes enzyme are analysed using HPLC-MS on the C18 Waters BEH column.

FIG. 11 shows the HPLC-MS chromatogram obtained with UV detection at 215 nm (A), with mass detection of the total ions (B), with mass detection selective for the ion m/z 187 characteristic of AP and PA (C).

Example 13: Hypothetical Action of a Protease of the Thermolysin Type on Proteins Containing AP and/or VAP Units 1/ Action of Thermolysin on Beta-lactoglobulin (Cow's Milk) P02754

The results from testing for peptides between 150 and 250 Da are shown in Table 3 below.

| m/z (mi) | Sequence |
|---|---|
| 187.1077 | AP |
| 189.1234 | AV |
| 203.1390 | AL |
| 203.1390 | LA |
| 218.1135 | AQ |
| 219.1339 | IS |
| 219.1339 | LS |
| 221.0954 | AM |
| 221.0954 | MA |
| 229.1547 | IP |
| 229.1547 | LP |
| 231.1703 | VL |
| 231.1703 | LV |
| 237.0904 | AM |
| 237.0904 | MA |
| 245.1860 | LL |
| 245.1860 | LI |
| 245.1860 | IL |
| 245.1860 | II |
| 247.1288 | LD |
| 247.1288 | ID |
| 248.1241 | AGT |

2/ Action of Thermolysin on Alpha-S1-casein (Cow's Milk) P02754

The results from testing for peptides between 150 and 250 Da are shown in Table 4 below.

| m/z (mi) | Sequence |
|---|---|
| 187.1077 | AP |
| 189.1234 | VA |
| 189.1234 | AV |
| 189.1234 | LG |
| 189.1234 | IG |
| 189.1234 | MK |
| 203.1390 | AL |
| 203.1390 | LA |
| 215.1390 | VP |
| 231.1703 | LV |
| 245.1860 | LL |
| 245.1860 | LI |
| 247.1111 | MP |
| 247.1288 | LD |

3/ Action of Thermolysin on Beta-casein (Cow's Milk) P02666

The results from testing for peptides between 150 and 250 Da are shown in Table 5 below.

| m/z (mi) | Sequence | m/z (mi) | Sequence | m/z (mi) | Sequence |
|---|---|---|---|---|---|
| 189.1234 | VA | 219.1339 | LS | 237.0904 | AM |
| 189.1234 | MK | 221.0954 | AM | 237.1234 | AF |
| 193.0641 | AC | 223.0747 | MG | 245.1860 | LI |
| 203.1390 | AL | 229.1547 | LP | 245.1860 | IL |
| 203.1390 | LA | 231.1703 | VL | 245.1860 | LL |
| 207.0798 | MG | 231.1703 | LV | 245.1860 | II |
| 215.1390 | VP | 231.1703 | IV | 246.1448 | LN |
| 217.1547 | VV | 233.1496 | LT | 246.1812 | MKV |
| 247.1111 | MP | 249.1267 | VM | | |

4/ Action of Thermolysin on Lactoferrin (Cow's Milk) P24627

The results from testing for peptides between 150 and 250 Da are shown in Table 6 below.

| m/z (mi) | Sequence | m/z (mi) | Sequence | m/z (mi) | Sequence |
|---|---|---|---|---|---|
| 187.1077 | AP | 229.1547 | IP | 245.1860 | LL |
| 189.1234 | VA | 231.1703 | VL | 246.1448 | LN |
| 189.1234 | AV | 231.1703 | IV | 246.1561 | AR |
| 189.1234 | LG | 231.1703 | LV | 246.1812 | VK |
| 189.1234 | MK | 233.1132 | VD | 249.1267 | MV |
| 191.1026 | AT | 233.1496 | LT | 223.0747 | MG |
| 193.0641 | AC | 235.1111 | LC | 223.1077 | FG |
| 203.1390 | AL | 237.1234 | AF | 227.1139 | AH |

-continued

| m/z (mi) | Sequence | m/z (mi) | Sequence | m/z (mi) | Sequence |
|---|---|---|---|---|---|
| 203.1390 | AI | 237.1234 | FA | 207.0798 | MG |
| 203.1390 | LA | 239.1026 | YG | 215.1390 | VP |
| 204.0979 | AN | 244.1292 | APG | 217.1547 | VV |
| 205.0819 | AD | 245.1860 | LI | 227.1139 | AH |
| 218.1135 | AQ | 246.1812 | VK | 219.1339 | LS |
| 218.1499 | AK | 249.1267 | MV | 223.1077 | FG |
| 219.0975 | AE | 223.0747 | MG | 219.1339 | VT |

5/ Action of Thermolysin on Actin (Atlantic Salmon) B5XFZ3

The results from testing for peptides between 150 and 250 Da are shown in Table 7 below.

| m/z (mi) | Sequence |
|---|---|
| 161.0921 | AA |
| 175.1077 | VG |
| 177.0870 | AS |
| 187.1077 | AP |
| 189.1234 | VA |
| 189.1234 | AV |
| 189.1234 | IG |
| 203.1390 | AL |
| 203.1390 | AI |
| 203.1390 | LA |
| 205.1183 | VS |
| 215.1390 | VP |
| 215.1390 | VP |
| 219.1339 | LS |
| 221.0954 | AM |
| 231.1703 | VL |
| 231.1703 | LV |
| 231.1703 | IV |
| 233.1132 | VD |
| 233.1496 | IT |
| 235.1111 | LC |
| 245.1860 | IL |
| 246.1448 | AVG |
| 247.1288 | LD |

6/ Action of Thermolysin on Collagen Alpha2 (I) (*Oncorhynchus keta*, Chum Salmon) Q8UUJ4

The results from testing for peptides between 150 and 250 Da are shown in Table 8 below.

| m/z (mi) | Sequence | m/z (mi) | Sequence |
|---|---|---|---|
| 175.1077 | VG | 223.1077 | FG |
| 187.1077 | AP | 229.1547 | LP |
| 189.1234 | VA | 231.1703 | VL |
| 189.1234 | AV | 233.1132 | VD |
| 189.1234 | IG | 233.1496 | IT |
| 189.1234 | LG | 234.1084 | AGS |
| 191.1026 | AT | 237.1234 | FA |
| 203.1390 | LA | 237.1234 | AF |
| 205.0819 | AD | 244.1292 | AGP |
| 207.0798 | MG | 244.1292 | APG |
| 218.1135 | AQ | 245.1860 | IL |
| 218.1135 | AAG | 245.1860 | LL |
| 219.1339 | MLS | 246.1448 | VAG |
| 219.1339 | LS | 246.1448 | AGV |
| 221.0954 | VC | 246.1448 | VGA |
| 247.1288 | LD | 246.1448 | IGG |
| 248.1241 | ATG | 247.1288 | VE |

7/ Action of Thermolysin on the Collagen Alpha1 (II) Sequence (Bovine) P02459

The results from testing for peptides between 150 and 250 Da are shown in Table 9 below.

| m/z (mi) | Sequence |
|---|---|
| 175.1077 | VG |
| 177.0870 | AS |
| 187.1077 | AP |
| 191.1026 | AT |
| 203.1390 | AL |
| 203.1390 | IA |
| 204.0979 | AGG |
| 204.0979 | AN |
| 207.0798 | MG |
| 218.1135 | AQ |
| 218.1135 | AGA |
| 218.1135 | AAG |
| 218.1135 | AGA |
| 219.0975 | AE |
| 221.0954 | VC |
| 223.0747 | MG |
| 223.1077 | FG |
| 229.1547 | LP |
| 233.1132 | VD |
| 233.1496 | IT |
| 237.0904 | MS |
| 237.1234 | AF |
| 244.1292 | APG |
| 244.1292 | AGP |
| 245.1860 | LL |
| 246.1448 | AVG |
| 246.1448 | VQ |
| 247.1288 | VE |
| 247.1288 | ID |
| 247.1288 | LD |
| 247.1288 | ID |
| 248.1241 | AGT |
| 248.1241 | ATG |

8/ Action of Thermolysin on Elastin (Bovine) F1NOH9

The results from testing for peptides between 150 and 250 Da are shown in Table 10 below.

| m/z (mi) | Sequence |
|---|---|
| 161.0921 | AA |
| 175.1077 | VG |
| 187.1077 | AP |
| 189.0870 | MAG |
| 189.1234 | AV |
| 189.1234 | LG |
| 189.1234 | IG |
| 191.1026 | AT |
| 203.1390 | AL |
| 203.1390 | LA |
| 203.1390 | IA |
| 204.0979 | AGG |
| 205.1183 | VS |
| 215.1390 | VP |
| 218.1135 | AGA |
| 218.1135 | AAG |
| 218.1135 | AQ |
| 218.1499 | AK |
| 219.1339 | IS |
| 219.1339 | LS |
| 223.1077 | FG |
| 229.1547 | LP |
| 229.1547 | IP |
| 231.1703 | VL |
| 232.1292 | VGG |
| 233.1496 | LT |
| 235.1111 | LC |
| 237.1234 | AF |

-continued

| m/z (mi) | Sequence |
|---|---|
| 239.1026 | YG |
| 244.1292 | APG |
| 245.1860 | LL |
| 246.1448 | VGA |
| 246.1448 | VAG |
| 246.1448 | AGV |
| 246.1448 | VQ |
| 246.1448 | LGG |
| 246.1448 | IGG |
| 246.1561 | AR |
| 247.1288 | LD |

9/ Action of Thermolysin on Ovotransferrin (Hen's Egg) P02789

The results from testing for peptides between 150 and 250 Da are shown in Table 11 below.

| m/z (mi) | Sequence | m/z (mi) | Sequence |
|---|---|---|---|
| 161.0921 | AA | 219.0975 | AE |
| 177.0870 | AS | 219.1339 | LS |
| 187.1077 | AP | 219.1339 | IS |
| 189.1234 | AV | 221.0954 | VC |
| 189.1234 | VA | 223.0747 | MG |
| 189.1234 | LG | 223.1077 | FG |
| 189.1234 | MK | 227.1139 | AH |
| 191.1026 | AT | 229.1547 | IP |
| 203.1390 | AI | 231.1703 | LV |
| 203.1390 | IA | 232.1292 | VN |
| 204.0979 | AN | 235.1111 | LC |
| 205.0819 | AD | 237.1234 | FA |
| 207.0798 | MG | 237.1234 | AF |
| 215.1390 | VP | 237.1234 | FA |
| 217.1547 | VV | 245.1860 | LI |
| 218.1499 | AK | 245.1860 | LL |
| 249.1267 | VM | 246.1561 | AR |
| 219.1339 | LS | 249.1267 | VM |

10/ Action of Thermolysin on Legumin A (*Pisum sativum*, Pea Proteins) P02857

The results from testing for peptides between 150 and 250 Da are shown in Table 12 below.

| m/z (mi) | Sequence |
|---|---|
| 177.0870 | AS |
| 189.1234 | VA |
| 189.1234 | AV |
| 191.1026 | AT |
| 203.1390 | AI |
| 203.1390 | LA |
| 203.1390 | IA |
| 205.1183 | VS |
| 215.1390 | VP |
| 217.1547 | VV |
| 218.1499 | MAK |
| 218.1499 | AK |
| 219.1339 | LS |
| 221.0954 | AM |
| 223.1077 | FG |
| 229.1547 | LP |
| 231.1703 | VI |
| 231.1703 | IV |
| 233.1496 | LT |
| 237.0904 | AM |
| 237.1234 | FA |
| 245.1860 | LL |
| 245.1860 | II |

| m/z (mi) | Sequence |
|---|---|
| 246.1448 | AGV |
| 246.1448 | LN |
| 246.1561 | AR |
| 246.1812 | VK |
| 247.1288 | LD |
| 248.1241 | ASA |
| 249.1267 | MV |

Example 14: In-vitro Determination of the Inhibition of DPP-IV (DiPeptidyl Peptidase-IV) by the Synthetic Peptides The inhibitory activity of synthetic peptides can be measured in vitro according to the following protocol:

25 µl of the substrate Gly-L-Pro-p-nitroanilide in 0.1 M Tris-HCL buffer (pH 8.0) at 1.6 mM is mixed with 25 µl of the peptide sample or of reference inhibitor at different concentrations. The samples are solubilized beforehand in Tris HCL buffer (pH8.0).

After preincubation at 37° C. for 10 min, 50 µl of the DPP-IV enzyme at a concentration of 0.01 U/ml in 0.1 M Tris-HCL buffer (pH 8.0) is added to the mixture in order to start the reaction. The reaction medium is incubated for 60 min at 37° C. and then the reaction is stopped by adding 100 µl of 1M sodium acetate buffer (pH4).

The quantity of product formed (p-nitroanilide) is measured by reading the absorbance at 385 nm using the Fluostar Omega spectrophotometer (BMG Labtech, Germany).

All the inhibition tests are carried out in triplicate.

The substrate used is Gly-L-Pro-p-nitroanilide hydrochloride (available from Sigma under reference G0513).

The enzyme used is DPP-IV from pig kidney (available from Sigma under reference D7052).

The reference inhibitor is Diprotin A, corresponding to the Ile-Pro-Ile tripeptide (available from Sigma under reference 19759).

The results for $IC_{50}$ of the peptides on the inhibitory activity of DPP-IV tested in vitro are shown in Table 13 below.

| Peptides | ($IC_{50}$) in mmol/l |
|---|---|
| Diprotin A (IPI) | 0.0121 ± 0.0002 |
| SAPLRVY (SEQ ID NO: 3) | 1.056 ± 0.031 |
| VAPFPEV (SEQ ID NO: 4) | 1.184 ± 0.008 |
| GPL | 1.853 ± 0.298 |
| VAPG (SEQ ID NO: 6) | 2.271 ± 0.131 |
| AP | 4.775 ± 0.284 |
| VAP | 4.817 ± 2.303 |
| AVPYQR (SEQ ID NO: 5) | 5.701 ± 0.080 |
| VGVAPG (SEQ ID NO: 7) | 10.732 ± 0.769 |
| KY | No inhibition |
| VW | No inhibition |
| VY | No inhibition |
| AVIPIPT | No inhibition |

The results confirm that the peptides used inhibit DPP-IV weakly relative to the reference, which is Diprotin A, a known inhibitor of DPP-IV. In particular, the AP and VAP peptides inhibit DPP-IV very weakly relative to the reference Diprotin A.

The invention claimed is:

1. A method for reducing glycemia by inhibiting alpha-glucosidase, said method comprising administering to a subject in need thereof a composition comprising at least one XAP peptide, in which X represents the empty set or a valine, wherein the XAP peptide is administered before or during a meal.

2. The method according to claim 1, wherein said composition comprises at least one VAP peptide and/or at least one AP peptide in combination with a peptide APX';

wherein A is alanine, P is proline, and X' is an amino acid or a group of amino acids selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

3. The method according to claim 1, wherein said composition is in unit form and comprises a quantity of XAP peptide from 5 mg to 3000 mg.

4. The method according to claim 1, wherein said composition comprises a quantity of VAP peptide from 5 mg to 3000 mg, or a quantity of AP peptide from 5 mg to 3000 mg, or a quantity of VAP and AP peptides from 5 mg to 3000 mg.

5. The method according to claim 4,
wherein said composition comprises:
a quantity of VAP peptide that is in a range selected from the group consisting of: from 5 mg to 7.4 mg, and from 7.5 mg to 3000 mg; or
a quantity of AP peptide that is in a range selected from the group consisting of: from 5 mg to 7.4 mg, and from 7.5 mg to 3000 mg; or
a quantity of VAP and AP peptides that is in a range selected from the group consisting of: from 5 mg to 7.4 mg, and from 7.5 mg to 3000 mg.

* * * * *

SEQUENCE LISTING

<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
<223> OTHER INFORMATION: synthesized

<400> SEQUENCE: 1

Ala Pro Phe Pro Glu
1               5

<210> SEQ ID NO 2
<211> LENGTH: 7
<212> TYPE: PRT
<213> ORGANISM: Artificial Sequence
<220> FEATURE:
<223> OTHER INFORMATION: synthesized

<400> SEQUENCE: 2

Ala Pro Phe Pro Glu Val Phe
1               5

<210> SEQ ID NO 3
<211> LENGTH: 7
<212> TYPE: PRT
<213> ORGANISM: Artificial Sequence
<220> FEATURE:
<223> OTHER INFORMATION: synthesized

<400> SEQUENCE: 3

Ser Ala Pro Leu Arg Val Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: synthesized

<400> SEQUENCE: 4

Val Ala Pro Phe Pro Glu Val
1               5

<210> SEQ ID NO 5
<211> LENGTH: 6
<212> TYPE: PRT
<213> ORGANISM: Artificial Sequence
<220> FEATURE:
<223> OTHER INFORMATION: synthesized

<400> SEQUENCE: 5

Ala Val Pro Tyr Gln Arg
1               5

<210> SEQ ID NO 6
<211> LENGTH: 4
<212> TYPE: PRT
<213> ORGANISM: Artificial Sequence
<220> FEATURE:
<223> OTHER INFORMATION: synthesized

<400> SEQUENCE: 6

Val Ala Pro Gly
1

<210> SEQ ID NO 7
<211> LENGTH: 6
<212> TYPE: PRT
<213> ORGANISM: Artificial Sequence
<220> FEATURE:
<223> OTHER INFORMATION: synthesized

<400> SEQUENCE: 7

Val Gly Val Ala Pro Gly
1               5

<210> SEQ ID NO 8
<211> LENGTH: 178
<212> TYPE: PRT
<213> ORGANISM: Bos taurus

<400> SEQUENCE: 8

Met Lys Cys Leu Leu Leu Ala Leu Ala Leu Thr Cys Gly Ala Gln Ala
1               5                   10                  15

Leu Ile Val Thr Gln Thr Met Lys Gly Leu Asp Ile Gln Lys Val Ala
                20                  25                  30

Gly Thr Trp Tyr Ser Leu Ala Met Ala Ala Ser Asp Ile Ser Leu Leu
            35                  40                  45

Asp Ala Gln Ser Ala Pro Leu Arg Val Tyr Val Glu Glu Leu Lys Pro
        50                  55                  60

Thr Pro Glu Gly Asp Leu Glu Ile Leu Leu Gln Lys Trp Glu Asn Gly
65                  70                  75                  80

Glu Cys Ala Gln Lys Lys Ile Ile Ala Glu Lys Thr Lys Ile Pro Ala
                85                  90                  95

Val Phe Lys Ile Asp Ala Leu Asn Glu Asn Lys Val Leu Val Leu Asp
                100                 105                 110

Thr Asp Tyr Lys Lys Tyr Leu Leu Phe Cys Met Glu Asn Ser Ala Glu
            115                 120                 125

Pro Glu Gln Ser Leu Ala Cys Gln Cys Leu Val Arg Thr Pro Glu Val
        130                 135                 140

Asp Asp Glu Ala Leu Glu Lys Phe Asp Lys Ala Leu Lys Ala Leu Pro
145                 150                 155                 160

Met His Ile Arg Leu Ser Phe Asn Pro Thr Gln Leu Glu Glu Gln Cys
                165                 170                 175

His Ile

<210> SEQ ID NO 9
<211> LENGTH: 214
<212> TYPE: PRT
<213> ORGANISM: Bos taurus

<400> SEQUENCE: 9

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
                20                  25                  30

Glu Asn Leu Leu Arg Phe Phe Val Ala Pro Phe Pro Glu Val Phe Gly
            35                  40                  45

Lys Glu Lys Val Asn Glu Leu Ser Lys Asp Ile Gly Ser Glu Ser Thr
        50                  55                  60

Glu Asp Gln Ala Met Glu Asp Ile Lys Gln Met Glu Ala Glu Ser Ile
65                  70                  75                  80

```
Ser Ser Ser Glu Glu Ile Val Pro Asn Ser Val Gln Lys His Ile
            85                  90                  95

Gln Lys Glu Asp Val Pro Ser Glu Arg Tyr Leu Gly Tyr Leu Glu Gln
           100                 105                 110

Leu Leu Arg Leu Lys Lys Tyr Lys Val Pro Gln Leu Glu Ile Val Pro
           115                 120                 125

Asn Ser Ala Glu Glu Arg Leu His Ser Met Lys Glu Gly Ile His Ala
           130                 135                 140

Gln Gln Lys Glu Pro Met Ile Gly Val Asn Gln Glu Leu Ala Tyr Phe
145                     150                 155                 160

Tyr Pro Glu Leu Phe Arg Gln Phe Tyr Gln Leu Asp Ala Tyr Pro Ser
               165                 170                 175

Gly Ala Trp Tyr Tyr Val Pro Leu Gly Thr Gln Tyr Thr Asp Ala Pro
               180                 185                 190

Ser Phe Ser Asp Ile Pro Asn Pro Ile Gly Ser Glu Asn Ser Glu Lys
               195                 200                 205

Thr Thr Met Pro Leu Trp
    210

<210> SEQ ID NO 10
<211> LENGTH: 224
<212> TYPE: PRT
<213> ORGANISM: Bos taurus

<400> SEQUENCE: 10

Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
            35                  40                  45

Gln Ser Glu Glu Gln Gln Gln Thr Glu Asp Glu Leu Gln Asp Lys Ile
        50                  55                  60

His Pro Phe Ala Gln Thr Gln Ser Leu Val Tyr Pro Phe Pro Gly Pro
65                  70                  75                  80

Ile Pro Asn Ser Leu Pro Gln Asn Ile Pro Pro Leu Thr Gln Thr Pro
                85                  90                  95

Val Val Val Pro Pro Phe Leu Gln Pro Glu Val Met Gly Val Ser Lys
           100                 105                 110

Val Lys Glu Ala Met Ala Pro Lys His Lys Glu Met Pro Phe Pro Lys
           115                 120                 125

Tyr Pro Val Glu Pro Phe Thr Glu Ser Gln Ser Leu Thr Leu Thr Asp
           130                 135                 140

Val Glu Asn Leu His Leu Pro Leu Pro Leu Leu Gln Ser Trp Met His
145                     150                 155                 160

Gln Pro His Gln Pro Leu Pro Pro Thr Val Met Phe Pro Pro Gln Ser
               165                 170                 175

Val Leu Ser Leu Ser Gln Ser Lys Val Leu Pro Val Pro Gln Lys Ala
               180                 185                 190

Val Pro Tyr Pro Gln Arg Asp Met Pro Ile Gln Ala Phe Leu Leu Tyr
               195                 200                 205

Gln Glu Pro Val Leu Gly Pro Val Arg Gly Pro Phe Pro Ile Ile Val
           210                 215                 220
```

<210> SEQ ID NO 11
<211> LENGTH: 708
<212> TYPE: PRT
<213> ORGANISM: Bos taurus

<400> SEQUENCE: 11

```
Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Arg Ala Phe Ala Leu Glu Cys
    50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
    210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
        275                 280                 285

Leu Leu Ser Lys Ala Gln Glu Lys Phe Gly Lys Asn Lys Ser Arg Ser
    290                 295                 300

Phe Gln Leu Phe Gly Ser Pro Gly Gln Arg Asp Leu Leu Phe Lys Asp
305                 310                 315                 320

Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
            340                 345                 350

Thr Ala Glu Glu Val Lys Ala Arg Tyr Thr Arg Val Val Trp Cys Ala
        355                 360                 365

Val Gly Pro Glu Glu Gln Lys Lys Cys Gln Gln Trp Ser Gln Gln Ser
    370                 375                 380
```

```
Gly Gln Asn Val Thr Cys Ala Thr Ala Ser Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
                420                 425                 430

Asn Arg Lys Ser Ser Lys His Ser Ser Leu Asp Cys Val Leu Arg Pro
                435                 440                 445

Thr Glu Gly Tyr Leu Ala Val Ala Val Val Lys Lys Ala Asn Glu Gly
                450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
                485                 490                 495

Thr Gly Ser Cys Ala Phe Asp Glu Phe Phe Ser Gln Ser Cys Ala Pro
                500                 505                 510

Gly Ala Asp Pro Lys Ser Arg Leu Cys Ala Leu Cys Ala Gly Asp Asp
                515                 520                 525

Gln Gly Leu Asp Lys Cys Val Pro Asn Ser Lys Glu Lys Tyr Tyr Gly
                530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
                580                 585                 590

Leu Asp Gly Thr Arg Lys Pro Val Thr Glu Ala Gln Ser Cys His Leu
                595                 600                 605

Ala Val Ala Pro Asn His Ala Val Val Ser Arg Ser Asp Arg Ala Ala
                610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
                660                 665                 670

Arg Pro Thr Tyr Glu Glu Tyr Leu Gly Thr Glu Tyr Val Thr Ala Ile
                675                 680                 685

Ala Asn Leu Lys Lys Cys Ser Thr Ser Pro Leu Leu Glu Ala Cys Ala
690                 695                 700

Phe Leu Thr Arg
705

<210> SEQ ID NO 12
<211> LENGTH: 376
<212> TYPE: PRT
<213> ORGANISM: Salmo

<400> SEQUENCE: 12

Met Val Glu Asp Glu Val Ala Ala Leu Val Ile Asp Asn Gly Ser Gly
1               5                   10                  15

Met Cys Lys Ser Gly Phe Ala Gly Asp Asp Ala Pro Arg Ala Val Phe
                20                  25                  30

Pro Ser Ile Val Gly Arg Pro Arg His Val Gly Ile Met Val Gly Met
                35                  40                  45
```

```
Gly Gln Lys Asp Ser Tyr Val Gly Asp Glu Ala Gln Ser Lys Arg Gly
         50                  55                  60

Ile Leu Ser Leu Lys Tyr Pro Ile Asp His Gly Ile Val Thr Asn Trp
 65                  70                  75                  80

Asp Asp Met Glu Lys Ile Trp His His Thr Phe Tyr Asn Glu Leu Arg
                 85                  90                  95

Val Ala Pro Glu Glu His Pro Val Leu Leu Thr Glu Ala Pro Leu Asn
                100                 105                 110

Pro Lys Asn Asn Arg Glu Lys Met Thr Gln Ile Met Phe Glu Thr Phe
            115                 120                 125

Asn Ser Pro Ala Met Tyr Val Ala Ile Gln Ala Val Leu Ser Leu Tyr
        130                 135                 140

Ala Ser Gly Arg Thr Thr Gly Ile Val Leu Asp Ser Gly Asp Gly Val
145                 150                 155                 160

Thr His Thr Val Pro Ile Tyr Glu Gly Tyr Ala Leu Pro His Ala Val
                165                 170                 175

Leu Arg Leu Asp Leu Ala Gly Arg Asp Leu Thr Asp Tyr Leu Met Lys
                180                 185                 190

Val Leu Thr Glu Arg Gly Tyr Ser Phe Thr Thr Thr Ala Glu Arg Glu
            195                 200                 205

Ile Val Arg Asp Val Lys Glu Lys Leu Cys Tyr Val Ala Leu Asp Tyr
        210                 215                 220

Thr Asn Glu Leu Ala Val Ala Gly Ser Ser Ser Ser Leu Glu Lys Ser
225                 230                 235                 240

Tyr Glu Leu Pro Asp Gly Gln Val Ile Thr Ile Gly Ser Glu Arg Phe
                245                 250                 255

Arg Cys Pro Glu Ala Leu Phe Gln Pro Ala Leu Ile Gly Met Glu Ala
                260                 265                 270

Val Gly Ile His Glu Thr Ala Tyr Asn Ser Ile Met Lys Cys Asp Val
            275                 280                 285

Asp Ile Arg Lys Asp Leu Tyr Ala Asn Thr Val Leu Ser Gly Gly Ser
        290                 295                 300

Thr Met Phe Ser Gly Ile Ala Asp Arg Met Gln Lys Glu Val Ser Ala
305                 310                 315                 320

Leu Ala Pro Thr Thr Met Lys Ile Lys Ile Ile Ser Pro Pro Glu Arg
                325                 330                 335

Lys Tyr Ser Val Trp Ile Gly Gly Ser Ile Leu Ala Ser Leu Ser Thr
                340                 345                 350

Phe Gln Gln Met Trp Ile Ser Lys Met Glu Tyr Asp Glu Ser Gly Pro
            355                 360                 365

Ala Ile Val His Arg Lys Cys Phe
        370                 375

<210> SEQ ID NO 13
<211> LENGTH: 1352
<212> TYPE: PRT
<213> ORGANISM: Salmo

<400> SEQUENCE: 13

Met Leu Ser Phe Val Asp Asn Arg Ile Leu Leu Leu Ala Val Thr
  1               5                  10                  15

Ser Leu Leu Ala Ser Cys Gln Ser Gly Pro Arg Gly Ala Lys Gly Pro
             20                  25                  30

Arg Gly Asp Arg Gly Pro Gln Gly Pro Asn Gly Arg Asp Gly Lys Ala
```

```
            35                  40                  45
Gly Leu Pro Gly Val Ala Gly Pro Pro Gly Pro Pro Gly Leu Gly Gly
 50                  55                  60

Asn Phe Ala Ala Gln Phe Asp Gly Gly Lys Gly Ser Asp Pro Gly Pro
 65                  70                  75                  80

Gly Pro Met Gly Leu Met Gly Ser Arg Gly Pro Asn Gly Pro Pro Gly
                 85                  90                  95

Ser Pro Gly Pro Gln Gly Phe Thr Gly His Ala Gly Glu Pro Gly Glu
            100                 105                 110

Pro Gly Gln Thr Gly Ser Ile Gly Ala Arg Gly Pro Thr Gly Ser Ala
            115                 120                 125

Gly Lys Pro Gly Glu Asp Gly Asn Asn Gly Arg Pro Gly Lys Pro Gly
            130                 135                 140

Asp Arg Gly Gly Pro Gly Thr Gln Gly Ala Arg Gly Phe Pro Gly Thr
145                 150                 155                 160

Pro Gly Leu Pro Gly Met Lys Gly His Arg Gly Tyr Asn Gly Leu Asp
                165                 170                 175

Gly Arg Lys Gly Glu Ser Gly Thr Ala Gly Ala Lys Gly Glu Thr Gly
            180                 185                 190

Ala His Gly Ala Asn Gly Thr Pro Gly Pro Ala Gly Ser Arg Gly Leu
            195                 200                 205

Asn Gly Glu Arg Gly Arg Ala Gly Pro Ala Gly Pro Ala Gly Ala Arg
210                 215                 220

Gly Ala Asp Gly Ser Thr Gly Pro Ala Gly Pro Ala Gly Pro Leu Gly
225                 230                 235                 240

Ala Ala Gly Pro Pro Gly Phe Pro Gly Ala Pro Gly Pro Lys Gly Glu
                245                 250                 255

Ile Gly Gly Ala Gly Ser Asn Gly Pro Ser Gly Pro Gln Gly Gly Arg
            260                 265                 270

Gly Glu Pro Gly Ile Asn Gly Ala Val Gly Pro Val Gly Pro Val Gly
            275                 280                 285

Asn Pro Gly Asn Asn Gly Ile Asn Gly Ala Lys Gly Ala Ala Gly Leu
290                 295                 300

Pro Gly Val Ala Gly Ala Pro Gly Phe Pro Gly Pro Arg Gly Gly Pro
305                 310                 315                 320

Gly Pro Gln Gly Pro Gln Gly Ser Thr Gly Ala Arg Gly Leu Gly Gly
                325                 330                 335

Asp Pro Gly Pro Ser Gly Gln Lys Gly Asp Ser Gly Ala Lys Gly Glu
            340                 345                 350

Pro Gly His Ser Gly Val Gln Gly Ala Ala Gly Pro Ala Gly Glu Glu
            355                 360                 365

Gly Lys Arg Gly Ser Thr Gly Glu Ala Gly Ala Thr Gly Pro Ala Gly
            370                 375                 380

Leu Arg Gly Ala Arg Gly Gly Ala Gly Thr Arg Gly Leu Pro Gly Leu
385                 390                 395                 400

Glu Gly Arg Gly Gly Pro Ile Gly Met Pro Gly Ala Arg Gly Ala Thr
                405                 410                 415

Gly Pro Ala Gly Ile Arg Gly Ala Pro Gly Asp Ala Gly Arg Ala Gly
            420                 425                 430

Glu Ser Gly Leu Thr Gly Ala Arg Gly Leu Pro Gly Asn Ser Gly Gln
            435                 440                 445

Gly Gly Pro Pro Gly Lys Glu Gly Pro Ser Gly Ala Ala Gly Leu Asp
450                 455                 460
```

-continued

```
Gly Arg Thr Gly Pro Pro Gly Pro Thr Gly Pro Arg Gly Gln Pro Gly
465                 470                 475                 480

Asn Ile Gly Phe Pro Gly Pro Lys Gly Pro Gly Glu Ala Gly Lys
            485                 490                 495

Gly Gly Asp Lys Gly Pro Thr Gly Ala Thr Gly Leu Arg Gly Gly Pro
        500                 505                 510

Gly Ala Asp Gly Asn Asn Gly Ala Pro Gly Pro Ala Gly Val Val Gly
            515                 520                 525

Asn Ala Gly Glu Lys Gly Glu Gln Gly Pro Ser Gly Ala Pro Gly Phe
530                 535                 540

Gln Gly Leu Pro Gly Pro Ala Gly Pro Ala Gly Glu Ala Gly Lys Ala
545                 550                 555                 560

Gly Asn Gln Gly Met Pro Gly Asp Gln Gly Leu Pro Gly Pro Ala Gly
                565                 570                 575

Val Lys Gly Glu Arg Gly Asn Ser Gly Pro Ala Gly Ser Ala Gly Ser
            580                 585                 590

Gln Gly Ala Ile Gly Ala Arg Gly Pro Ala Gly Thr Pro Gly Pro Asp
        595                 600                 605

Gly Gly Lys Gly Glu Pro Gly Ser Val Gly Ile Val Gly Ala Ala Gly
610                 615                 620

His Gln Gly Pro Gly Gly Met Pro Gly Glu Arg Gly Ala Gly Gly Thr
625                 630                 635                 640

Pro Gly Pro Lys Gly Glu Lys Gly Glu Gly Gly His Arg Gly Leu Glu
                645                 650                 655

Gly Asn Met Gly Arg Asp Gly Ala Arg Gly Ala Ala Gly Pro Ser Gly
            660                 665                 670

Pro Pro Gly Pro Ser Gly Ala Asn Gly Glu Lys Gly Glu Ser Gly Ser
        675                 680                 685

Phe Gly Pro Ala Gly Pro Ala Gly Leu Arg Gly Pro Ser Gly Glu Arg
690                 695                 700

Gly Glu Gly Gly Pro Ala Gly Pro Gly Phe Ala Gly Pro Pro Gly
705                 710                 715                 720

Ser Asp Gly Gln Ser Gly Pro Arg Gly Glu Lys Gly Pro Ala Gly Gly
                725                 730                 735

Lys Gly Asp Val Gly Pro Ala Gly Pro Ala Gly Pro Ser Gly Gln Ser
            740                 745                 750

Gly Pro Ser Gly Ala Ser Gly Pro Ala Gly Pro Pro Gly Gly Arg Gly
        755                 760                 765

Asp Ala Gly Pro Ser Gly Leu Thr Gly Phe Pro Gly Ala Ala Gly Arg
        770                 775                 780

Val Gly Gly Pro Gly Pro Ala Gly Ile Ser Gly Pro Pro Gly Ser Ala
785                 790                 795                 800

Gly Pro Ala Gly Lys Asp Gly Pro Arg Gly Leu Arg Gly Asp Ala Gly
                805                 810                 815

Pro Gly Gly Pro Gln Gly Glu Gln Gly Val Val Gly Pro Ala Gly Ile
            820                 825                 830

Ala Gly Asp Lys Gly Pro Ser Gly Glu Gly Pro Pro Gly Ala Pro
        835                 840                 845

Gly Thr Ala Gly Pro Gln Gly Val Leu Gly Pro Ser Gly Phe Val Gly
850                 855                 860

Leu Pro Gly Ser Arg Gly Asp Lys Gly Leu Pro Gly Gly Pro Gly Ala
865                 870                 875                 880
```

-continued

Val Gly Glu Pro Gly Arg Leu Gly Pro Ala Gly Ser Gly Pro Arg
            885                 890                 895

Gly Pro Ser Gly Asn Ile Gly Met Pro Gly Met Thr Gly Thr Gln Gly
        900                 905                 910

Glu Ala Gly Arg Glu Gly Asn Ser Gly Asn Asp Gly Pro Pro Gly Arg
            915                 920                 925

Pro Gly Ala Ala Gly Phe Lys Gly Asp Arg Gly Glu Pro Gly Ser Pro
    930                 935                 940

Gly Ala Leu Gly Ser Ser Gly Gln Pro Gly Asn Gly Pro Ala Gly
945                 950                 955                 960

Ser Ala Gly Arg Pro Gly Asn Arg Gly Glu Ser Gly Pro Thr Gly Asn
            965                 970                 975

Gly Gly Pro Val Gly Ala Ala Gly Ala Arg Gly Ala Pro Gly Pro Ala
        980                 985                 990

Gly Pro Arg Gly Glu Lys Gly Gly Ala Gly Glu Lys Gly Asp Arg Gly
        995                 1000                1005

Met Lys Gly Leu Arg Gly His Gly Gly Leu Gln Gly Met Pro Gly
    1010                1015                1020

Pro Asn Gly Pro Ser Gly Glu Thr Gly Ser Ala Gly Ile Thr Gly
    1025                1030                1035

Pro Ala Gly Pro Arg Gly Pro Ala Gly Pro His Gly Pro Pro Gly
    1040                1045                1050

Lys Asp Gly Arg Ala Gly Gly His Gly Ala Ile Gly Pro Val Gly
    1055                1060                1065

His Arg Gly Pro Pro Gly His Leu Gly Pro Ala Gly Pro Pro Gly
    1070                1075                1080

Ser Pro Gly Leu Pro Gly Pro Ala Gly Pro Ala Gly Gly Gly Tyr
    1085                1090                1095

Asp Gln Ser Gly Gly Tyr Asp Glu Tyr Arg Ala Asp Gln Pro Ser
    1100                1105                1110

Leu Arg Ala Lys Asp Tyr Glu Val Asp Ala Thr Ile Lys Ser Leu
    1115                1120                1125

Asn Ser Gln Ile Glu Asn Leu Leu Thr Pro Glu Gly Ser Lys Lys
    1130                1135                1140

Asn Pro Ala Arg Thr Cys Arg Asp Ile Arg Leu Ser His Pro Glu
    1145                1150                1155

Trp Ser Ser Gly Phe Tyr Trp Ile Gly Pro Asn Gln Gly Cys Ile
    1160                1165                1170

Ala Asp Ala Ile Lys Ala Tyr Cys Asp Phe Ser Thr Gly His Thr
    1175                1180                1185

Cys Ile His Pro His Pro Glu Ser Ile Ala Arg Lys Asn Trp Tyr
    1190                1195                1200

Arg Ser Ser Glu Asn Lys Lys His Val Trp Phe Gly Glu Thr Ile
    1205                1210                1215

Asn Gly Gly Thr Glu Phe Ala Tyr Asn Asp Glu Thr Leu Ser Pro
    1220                1225                1230

Gln Ser Met Ala Thr Gln Leu Ala Phe Met Arg Leu Leu Ala Asn
    1235                1240                1245

Gln Ala Thr Gln Asn Ile Thr Tyr His Cys Lys Asn Ser Val Ala
    1250                1255                1260

Tyr Met Asp Gly Glu Asn Gly Asn Leu Lys Lys Ala Val Leu Leu
    1265                1270                1275

Gln Gly Ser Asn Asp Val Glu Leu Arg Ala Glu Gly Asn Ser Arg

```
                    1280                1285                1290
Phe Thr Phe Asn Val Leu Glu Asp Gly Cys Thr Arg His Thr Gly
        1295                1300                1305

Gln Trp Ser Lys Thr Val Ile Glu Tyr Arg Thr Asn Lys Pro Ser
    1310                1315                1320

Arg Leu Pro Ile Leu Asp Ile Ala Pro Leu Asp Ile Gly Glu Ala
    1325                1330                1335

Asp Gln Glu Phe Gly Leu Asp Ile Gly Pro Val Cys Phe Lys
    1340                1345                1350

<210> SEQ ID NO 14
<211> LENGTH: 1306
<212> TYPE: PRT
<213> ORGANISM: Bos taurus

<400> SEQUENCE: 14

Gln Met Ala Gly Gly Phe Asp Glu Lys Ala Gly Gly Ala Gln Met Gly
1               5                   10                  15

Val Met Gln Gly Pro Met Gly Pro Met Gly Pro Arg Gly Pro Pro Gly
            20                  25                  30

Pro Ala Gly Ala Pro Gly Pro Gln Gly Phe Gln Gly Asn Pro Gly Glu
        35                  40                  45

Pro Gly Glu Pro Gly Val Ser Gly Pro Met Gly Pro Arg Gly Pro Pro
    50                  55                  60

Gly Pro Pro Gly Lys Pro Gly Asp Asp Gly Glu Ala Gly Lys Pro Gly
65                  70                  75                  80

Lys Ser Gly Glu Arg Gly Pro Pro Gly Pro Gln Gly Ala Arg Gly Phe
                85                  90                  95

Pro Gly Thr Pro Gly Leu Pro Gly Val Lys Gly His Arg Gly Tyr Pro
            100                 105                 110

Gly Leu Asp Gly Ala Lys Gly Glu Ala Gly Ala Pro Gly Val Lys Gly
        115                 120                 125

Glu Ser Gly Ser Pro Gly Glu Asn Gly Ser Pro Gly Pro Met Gly Pro
    130                 135                 140

Arg Gly Leu Pro Gly Glu Arg Gly Arg Thr Gly Pro Ala Gly Ala Ala
145                 150                 155                 160

Gly Ala Arg Gly Asn Asp Gly Gln Pro Gly Pro Ala Gly Pro Pro Gly
                165                 170                 175

Pro Val Gly Pro Ala Gly Gly Pro Gly Phe Pro Gly Ala Pro Gly Ala
            180                 185                 190

Lys Gly Glu Ala Gly Pro Thr Gly Ala Arg Gly Pro Glu Gly Ala Gln
        195                 200                 205

Gly Pro Arg Gly Glu Pro Gly Thr Pro Gly Ser Pro Gly Pro Ala Gly
    210                 215                 220

Ala Ala Gly Asn Pro Gly Thr Asp Gly Ile Pro Gly Ala Lys Gly Ser
225                 230                 235                 240

Ala Gly Ala Pro Gly Ile Ala Gly Ala Pro Gly Phe Pro Gly Pro Arg
                245                 250                 255

Gly Pro Pro Gly Pro Gln Gly Ala Thr Gly Pro Leu Gly Pro Lys Gly
            260                 265                 270

Gln Thr Gly Glu Pro Gly Ile Ala Gly Phe Lys Gly Glu Gln Gly Pro
        275                 280                 285

Lys Gly Glu Pro Gly Pro Ala Gly Pro Gln Gly Ala Pro Gly Pro Ala
    290                 295                 300
```

Gly Glu Glu Gly Lys Arg Gly Ala Arg Gly Glu Pro Gly Gly Ala Gly
305                 310                 315                 320

Pro Ala Gly Pro Pro Gly Glu Arg Gly Ala Pro Gly Asn Arg Gly Phe
            325                 330                 335

Pro Gly Gln Asp Gly Leu Ala Gly Pro Lys Gly Ala Pro Gly Glu Arg
            340                 345                 350

Gly Pro Ser Gly Leu Ala Gly Pro Lys Gly Ala Asn Gly Asp Pro Gly
            355                 360                 365

Arg Pro Gly Glu Pro Gly Leu Pro Gly Ala Arg Gly Leu Thr Gly Arg
        370                 375                 380

Pro Gly Asp Ala Gly Pro Gln Gly Lys Val Gly Pro Ser Gly Ala Pro
385                 390                 395                 400

Gly Glu Asp Gly Arg Pro Gly Pro Gly Pro Gln Gly Ala Arg Gly
                405                 410                 415

Gln Pro Gly Val Met Gly Phe Pro Gly Pro Lys Gly Ala Asn Gly Glu
            420                 425                 430

Pro Gly Lys Ala Gly Glu Lys Gly Leu Pro Gly Ala Pro Gly Leu Arg
        435                 440                 445

Gly Leu Pro Gly Lys Asp Gly Glu Thr Gly Ala Ala Gly Pro Pro Gly
        450                 455                 460

Pro Ala Gly Pro Ala Gly Glu Arg Gly Glu Gln Gly Ala Pro Gly Pro
465                 470                 475                 480

Ser Gly Phe Gly Gly Leu Pro Gly Pro Pro Gly Pro Pro Gly Glu Gly
            485                 490                 495

Gly Lys Pro Gly Asp Gly Gly Val Pro Gly Glu Ala Gly Ala Pro Gly
        500                 505                 510

Leu Val Gly Pro Arg Gly Glu Arg Gly Phe Pro Gly Glu Arg Gly Ser
        515                 520                 525

Pro Gly Ser Gln Gly Leu Gln Gly Ala Arg Gly Leu Pro Gly Thr Pro
530                 535                 540

Gly Thr Asp Gly Pro Lys Gly Ala Ala Gly Pro Ala Gly Pro Pro Gly
545                 550                 555                 560

Ala Gln Gly Pro Pro Gly Leu Gln Gly Met Pro Gly Glu Arg Gly Ala
            565                 570                 575

Ala Gly Ile Ala Gly Pro Lys Gly Asp Arg Gly Asp Val Gly Glu Lys
            580                 585                 590

Gly Pro Glu Gly Ala Pro Gly Lys Asp Gly Gly Arg Gly Leu Thr Gly
        595                 600                 605

Pro Ile Gly Pro Pro Gly Pro Ala Gly Ala Asn Gly Glu Lys Gly Glu
        610                 615                 620

Val Gly Pro Pro Gly Pro Ala Gly Thr Ala Gly Ala Arg Gly Ala Pro
625                 630                 635                 640

Gly Glu Arg Gly Glu Thr Gly Pro Pro Gly Pro Ala Gly Phe Ala Gly
            645                 650                 655

Pro Pro Gly Ala Asp Gly Gln Pro Gly Ala Lys Gly Glu Gln Gly Glu
            660                 665                 670

Ala Gly Gln Lys Gly Asp Ala Gly Ala Pro Gly Pro Gln Gly Pro Ser
        675                 680                 685

Gly Ala Pro Gly Pro Gln Gly Pro Thr Gly Val Thr Gly Pro Lys Gly
        690                 695                 700

Ala Arg Gly Ala Gln Gly Pro Pro Gly Ala Thr Gly Phe Pro Gly Ala
        705                 710                 715                 720

Ala Gly Arg Val Gly Pro Pro Gly Ser Asn Gly Asn Pro Gly Pro Pro

```
                    725                 730                 735
Gly Pro Pro Gly Pro Ser Gly Lys Asp Gly Pro Lys Gly Ala Arg Gly
                740                 745                 750
Asp Ser Gly Pro Pro Gly Arg Ala Gly Asp Pro Gly Leu Gln Gly Pro
                755                 760                 765
Ala Gly Pro Pro Gly Glu Lys Gly Glu Pro Gly Asp Asp Gly Pro Ser
                770                 775                 780
Gly Pro Asp Gly Pro Pro Gly Pro Gln Gly Leu Ala Gly Gln Arg Gly
785                 790                 795                 800
Ile Val Gly Leu Pro Gly Gln Arg Gly Glu Arg Gly Phe Pro Gly Leu
                805                 810                 815
Pro Gly Pro Ser Gly Glu Pro Gly Lys Gln Gly Ala Pro Gly Ala Ser
                820                 825                 830
Gly Asp Arg Gly Pro Pro Gly Pro Val Gly Pro Pro Gly Leu Thr Gly
                835                 840                 845
Pro Ala Gly Glu Pro Gly Arg Glu Gly Ser Pro Gly Ala Asp Gly Pro
                850                 855                 860
Pro Gly Arg Asp Gly Ala Ala Gly Val Lys Gly Asp Arg Gly Glu Thr
865                 870                 875                 880
Gly Ala Val Gly Ala Pro Gly Ala Pro Gly Pro Pro Gly Ser Pro Gly
                885                 890                 895
Pro Ala Gly Pro Ile Gly Lys Gln Gly Asp Arg Gly Glu Ala Gly Ala
                900                 905                 910
Gln Gly Pro Met Gly Pro Ala Gly Pro Ala Gly Ala Arg Gly Met Pro
                915                 920                 925
Gly Pro Gln Gly Pro Arg Gly Asp Lys Gly Glu Thr Gly Glu Ala Gly
                930                 935                 940
Glu Arg Gly Leu Lys Gly His Arg Gly Phe Thr Gly Leu Gln Gly Leu
945                 950                 955                 960
Pro Gly Pro Pro Gly Pro Ser Gly Asp Gln Gly Ala Ser Gly Pro Ala
                965                 970                 975
Gly Pro Ser Gly Pro Arg Gly Pro Pro Gly Pro Val Gly Pro Ser Gly
                980                 985                 990
Lys Asp Gly Ala Asn Gly Ile Pro  Gly Pro Ile Gly Pro  Pro Gly Pro
                995                 1000                1005
Arg Gly Arg Ser Gly Glu Thr  Gly Pro Ala Gly Pro  Pro Gly Asn
                1010                1015                1020
Pro Gly Pro Pro Gly Pro  Gly Pro Pro Gly Pro  Gly Ile Asp
                1025                1030                1035
Met Ser Ala Phe Ala Gly Leu  Gly Gln Arg Glu Lys  Gly Pro Asp
                1040                1045                1050
Pro Leu Gln Tyr Met Arg Ala  Asp Glu Ala Ala Gly  Asn Leu Arg
                1055                1060                1065
Gln His Asp Ala Glu Val Asp  Ala Thr Leu Lys Ser  Leu Asn Asn
                1070                1075                1080
Gln Ile Glu Ser Leu Arg Ser  Pro Glu Gly Ser Arg  Lys Asn Pro
                1085                1090                1095
Ala Arg Thr Cys Arg Asp Leu  Lys Leu Cys His Pro  Glu Trp Lys
                1100                1105                1110
Ser Gly Asp Tyr Trp Ile Asp  Pro Asn Gln Gly Cys  Thr Leu Asp
                1115                1120                1125
Ala Met Lys Val Phe Cys Asn  Met Glu Thr Gly Glu  Thr Cys Val
                1130                1135                1140
```

```
Tyr Pro Asn Pro Ala Ser Val Pro Lys Lys Asn Trp Trp Ser Ser
    1145                1150                1155

Lys Ser Lys Asp Lys Lys His Ile Trp Phe Gly Glu Thr Ile Asn
    1160                1165                1170

Gly Gly Phe His Phe Ser Tyr Gly Asp Asp Asn Leu Ala Pro Asn
    1175                1180                1185

Thr Ala Asn Val Gln Met Thr Phe Leu Arg Leu Leu Ser Thr Glu
    1190                1195                1200

Gly Ser Gln Asn Ile Thr Tyr His Cys Lys Asn Ser Ile Ala Tyr
    1205                1210                1215

Leu Asp Glu Ala Ala Gly Asn Leu Lys Lys Ala Leu Leu Ile Gln
    1220                1225                1230

Gly Ser Asn Asp Val Glu Ile Arg Ala Glu Gly Asn Ser Arg Phe
    1235                1240                1245

Thr Tyr Thr Val Leu Lys Asp Gly Cys Thr Lys His Thr Gly Lys
    1250                1255                1260

Trp Gly Lys Thr Met Ile Glu Tyr Arg Ser Gln Lys Thr Ser Arg
    1265                1270                1275

Leu Pro Ile Ile Asp Ile Ala Pro Met Asp Ile Gly Gly Pro Glu
    1280                1285                1290

Gln Glu Phe Gly Val Asp Ile Gly Pro Val Cys Phe Leu
    1295                1300                1305

<210> SEQ ID NO 15
<211> LENGTH: 805
<212> TYPE: PRT
<213> ORGANISM: Bos taurus

<400> SEQUENCE: 15

Met Ala Gly Leu Thr Ala Ala Arg Arg Pro Gly Val Leu Leu Leu
1               5                   10                  15

Leu Leu Cys Ile Leu Gln Pro Ser Gln Pro Gly Val Pro Gly Ala
                20                  25                  30

Val Pro Gly Gly Val Pro Gly Gly Val Phe Phe Pro Gly Ala Gly Leu
            35                  40                  45

Gly Gly Leu Gly Val Gly Ala Leu Gly Pro Gly Val Lys Pro Ala Lys
        50                  55                  60

Pro Gly Val Gly Gly Leu Ala Gly Pro Gly Leu Gly Ala Gly Leu Gly
65                  70                  75                  80

Ala Leu Pro Gly Ala Phe Pro Gly Ala Leu Val Pro Gly Gly Pro Ala
                85                  90                  95

Gly Ala Ala Ala Ala Tyr Lys Ala Ala Ala Lys Ala Gly Ala Ala Gly
                100                 105                 110

Leu Gly Val Gly Gly Ile Gly Gly Val Gly Gly Leu Gly Val Ser Thr
            115                 120                 125

Gly Ala Val Val Pro Gln Leu Gly Ala Gly Val Gly Ala Gly Val Lys
        130                 135                 140

Pro Gly Lys Val Pro Gly Val Gly Leu Pro Gly Val Tyr Pro Gly Gly
145                 150                 155                 160

Val Leu Pro Gly Ala Gly Ala Arg Phe Pro Gly Ile Gly Val Leu Pro
                165                 170                 175

Gly Val Pro Thr Gly Ala Gly Val Lys Pro Lys Ala Pro Gly Gly Gly
            180                 185                 190

Gly Ala Phe Ala Gly Ile Pro Gly Val Gly Pro Phe Gly Gly Gln Gln
```

-continued

```
              195                 200                 205
Pro Gly Val Pro Leu Gly Tyr Pro Ile Lys Ala Pro Lys Leu Pro Gly
            210                 215                 220
Gly Tyr Gly Leu Pro Tyr Ser Thr Gly Lys Leu Pro Tyr Gly Phe Gly
225                 230                 235                 240
Pro Gly Gly Val Ala Gly Ala Gly Lys Ala Gly Tyr Pro Thr Gly
                245                 250                 255
Thr Gly Val Gly Pro Gln Ala Ala Ala Ala Ala Lys Ala Ala
                260                 265                 270
Lys Leu Gly Ala Gly Gly Ala Gly Val Leu Pro Gly Val Gly Val Gly
                275                 280                 285
Gly Ala Gly Ile Pro Gly Ala Pro Gly Ala Ile Pro Gly Ile Gly Gly
            290                 295                 300
Ile Ala Gly Val Gly Ala Pro Asp Ala Ala Ala Ala Ala Ala
305                 310                 315                 320
Ala Lys Ala Ala Lys Phe Gly Ala Ala Gly Gly Phe Pro Gly Val Gly
                325                 330                 335
Val Pro Gly Val Gly Val Pro Gly Val Gly Val Pro Gly Val Gly Val
                340                 345                 350
Pro Gly Val Gly Val Pro Gly Val Gly Val Pro Gly Val Gly Val Pro
                355                 360                 365
Gly Val Gly Val Pro Gly Val Gly Val Pro Gly Val Gly Val Pro Gly
            370                 375                 380
Val Gly Val Pro Gly Ala Val Ser Pro Ala Ala Ala Lys Ala Ala
385                 390                 395                 400
Ala Lys Ala Ala Lys Phe Gly Ala Arg Gly Val Gly Val Gly Gly
                405                 410                 415
Ile Pro Thr Phe Gly Val Gly Pro Gly Gly Phe Pro Gly Ile Gly Asp
            420                 425                 430
Ala Ala Ala Ala Gln Ala Ala Ala Ala Lys Ala Ala Lys Ile Gly
            435                 440                 445
Ala Gly Gly Val Gly Ala Leu Gly Gly Leu Val Pro Gly Ala Pro Gly
            450                 455                 460
Ala Ile Pro Gly Val Pro Gly Val Gly Val Pro Gly Val Gly Ile
465                 470                 475                 480
Pro Ala Ala Ala Ala Lys Ala Ala Lys Ala Ala Gln Phe Gly
                485                 490                 495
Leu Gly Pro Gly Val Gly Val Ala Pro Gly Val Gly Val Val Pro Gly
                500                 505                 510
Val Gly Val Val Pro Gly Val Gly Val Ala Pro Gly Ile Gly Leu Gly
                515                 520                 525
Pro Gly Gly Val Ile Gly Ala Gly Val Pro Ala Ala Ala Lys Ser Ala
            530                 535                 540
Ala Lys Ala Ala Ala Lys Ala Gln Phe Arg Ala Ala Ala Gly Leu Pro
545                 550                 555                 560
Ala Gly Val Pro Gly Leu Gly Val Gly Val Gly Pro Gly Leu Gly
                565                 570                 575
Val Gly Val Gly Val Pro Gly Leu Gly Val Gly Ala Gly Val Pro Gly
                580                 585                 590
Leu Gly Ala Val Pro Gly Thr Leu Ala Ala Lys Ala Ala Lys Phe
                595                 600                 605
Gly Pro Gly Gly Val Gly Ala Leu Gly Gly Val Gly Asp Leu Gly Gly
            610                 615                 620
```

```
Ala Gly Ile Pro Gly Gly Val Ala Gly Val Gly Pro Ala Ala Ala
625                 630                 635                 640

Ala Ala Ala Lys Ala Ala Val Gln Leu Val Pro Lys His Arg Asn Pro
            645                 650                 655

His Ala Gly Leu Gly His Thr Ile Ser Trp Pro Pro Trp Pro Pro Phe
        660                 665                 670

Pro Arg Pro Ile Ala Val Pro Tyr Val Arg Arg Leu Pro Pro Pro
        675                 680                 685

Tyr Trp Glu Gln Pro Ser Cys Ser Cys Gly Ile His Pro Pro Ile Cys
        690                 695                 700

Pro Ser Val Arg Pro Ser Leu Ser Trp Phe Gly Arg Pro Ala Pro Leu
705                 710                 715                 720

Ala Gly Trp Ala Pro Pro Ser Thr Trp Leu Thr Cys His Gly Ser
            725                 730                 735

Leu Gly Pro Ala Ser Thr Pro Ser His Thr Pro Leu Arg Arg Gly Pro
            740                 745                 750

Glu Pro Leu Gly Val Lys Ser Cys Thr Ser Trp Gly Arg Arg Asn Leu
        755                 760                 765

Arg Pro Asn Leu Asp Leu Pro Pro Arg Ser Thr Val Ser Pro Ser Pro
770                 775                 780

Pro Arg Ala Thr Val Leu Gln Ser Ile Ser Pro Pro Arg Pro Ser
785                 790                 795                 800

Leu Cys Val Ser Leu
            805

<210> SEQ ID NO 16
<211> LENGTH: 705
<212> TYPE: PRT
<213> ORGANISM: Gallus gallus

<400> SEQUENCE: 16

Met Lys Leu Ile Leu Cys Thr Val Leu Ser Leu Gly Ile Ala Ala Val
1               5                   10                  15

Cys Phe Ala Ala Pro Pro Lys Ser Val Ile Arg Trp Cys Thr Ile Ser
            20                  25                  30

Ser Pro Glu Glu Lys Lys Cys Asn Asn Leu Arg Asp Leu Thr Gln Gln
        35                  40                  45

Glu Arg Ile Ser Leu Thr Cys Val Gln Lys Ala Thr Tyr Leu Asp Cys
    50                  55                  60

Ile Lys Ala Ile Ala Asn Asn Glu Ala Asp Ala Ile Ser Leu Asp Gly
65                  70                  75                  80

Gly Gln Ala Phe Glu Ala Gly Leu Ala Pro Tyr Lys Leu Lys Pro Ile
                85                  90                  95

Ala Ala Glu Val Tyr Glu His Thr Glu Gly Ser Thr Thr Ser Tyr Tyr
            100                 105                 110

Ala Val Ala Val Val Lys Lys Gly Thr Glu Phe Thr Val Asn Asp Leu
        115                 120                 125

Gln Gly Lys Thr Ser Cys His Thr Gly Leu Gly Arg Ser Ala Gly Trp
    130                 135                 140

Asn Ile Pro Ile Gly Thr Leu Leu His Arg Gly Ala Ile Glu Trp Glu
145                 150                 155                 160

Gly Ile Glu Ser Gly Ser Val Glu Gln Ala Val Ala Lys Phe Phe Ser
                165                 170                 175

Ala Ser Cys Val Pro Gly Ala Thr Ile Glu Gln Lys Leu Cys Arg Gln
```

-continued

```
              180                 185                 190
Cys Lys Gly Asp Pro Lys Thr Lys Cys Ala Arg Asn Ala Pro Tyr Ser
            195                 200                 205
Gly Tyr Ser Gly Ala Phe His Cys Leu Lys Asp Gly Lys Gly Asp Val
            210                 215                 220
Ala Phe Val Lys His Thr Thr Val Asn Glu Asn Ala Pro Asp Gln Lys
225                 230                 235                 240
Asp Glu Tyr Glu Leu Leu Cys Leu Asp Gly Ser Arg Gln Pro Val Asp
                245                 250                 255
Asn Tyr Lys Thr Cys Asn Trp Ala Arg Val Ala Ala His Ala Val Val
                260                 265                 270
Ala Arg Asp Asp Asn Lys Val Glu Asp Ile Trp Ser Phe Leu Ser Lys
            275                 280                 285
Ala Gln Ser Asp Phe Gly Val Asp Thr Lys Ser Asp Phe His Leu Phe
            290                 295                 300
Gly Pro Pro Gly Lys Lys Asp Pro Val Leu Lys Asp Leu Leu Phe Lys
305                 310                 315                 320
Asp Ser Ala Ile Met Leu Lys Arg Val Pro Ser Leu Met Asp Ser Gln
                325                 330                 335
Leu Tyr Leu Gly Phe Glu Tyr Tyr Ser Ala Ile Gln Ser Met Arg Lys
                340                 345                 350
Asp Gln Leu Thr Pro Ser Pro Arg Glu Asn Arg Ile Gln Trp Cys Ala
            355                 360                 365
Val Gly Lys Asp Glu Lys Ser Lys Cys Asp Arg Trp Ser Val Val Ser
            370                 375                 380
Asn Gly Asp Val Glu Cys Thr Val Val Asp Glu Thr Lys Asp Cys Ile
385                 390                 395                 400
Ile Lys Ile Met Lys Gly Glu Ala Asp Ala Val Ala Leu Asp Gly Gly
                405                 410                 415
Leu Val Tyr Thr Ala Gly Val Cys Gly Leu Val Pro Val Met Ala Glu
            420                 425                 430
Arg Tyr Asp Asp Glu Ser Gln Cys Ser Lys Thr Asp Glu Arg Pro Ala
            435                 440                 445
Ser Tyr Phe Ala Val Ala Val Ala Arg Lys Asp Ser Asn Val Asn Trp
            450                 455                 460
Asn Asn Leu Lys Gly Lys Lys Ser Cys His Thr Ala Val Gly Arg Thr
465                 470                 475                 480
Ala Gly Trp Val Ile Pro Met Gly Leu Ile His Asn Arg Thr Gly Thr
                485                 490                 495
Cys Asn Phe Asp Glu Tyr Phe Ser Glu Gly Cys Ala Pro Gly Ser Pro
                500                 505                 510
Pro Asn Ser Arg Leu Cys Gln Leu Cys Gln Gly Ser Gly Gly Ile Pro
            515                 520                 525
Pro Glu Lys Cys Val Ala Ser Ser His Glu Lys Tyr Phe Gly Tyr Thr
            530                 535                 540
Gly Ala Leu Arg Cys Leu Val Glu Lys Gly Asp Val Ala Phe Ile Gln
545                 550                 555                 560
His Ser Thr Val Glu Glu Asn Thr Gly Gly Lys Asn Lys Ala Asp Trp
                565                 570                 575
Ala Lys Asn Leu Gln Met Asp Asp Phe Glu Leu Leu Cys Thr Asp Gly
            580                 585                 590
Arg Arg Ala Asn Val Met Asp Tyr Arg Glu Cys Asn Leu Ala Glu Val
            595                 600                 605
```

```
Pro Thr His Ala Val Val Arg Pro Glu Lys Ala Asn Lys Ile Arg
    610             615                 620

Asp Leu Leu Glu Arg Gln Glu Lys Arg Phe Gly Val Asn Gly Ser Glu
625             630              635                 640

Lys Ser Lys Phe Met Met Phe Glu Ser Gln Asn Lys Asp Leu Leu Phe
            645                 650                 655

Lys Asp Leu Thr Lys Cys Leu Phe Lys Val Arg Glu Gly Thr Thr Tyr
            660                 665                 670

Lys Glu Phe Leu Gly Asp Lys Phe Tyr Thr Val Ile Ser Ser Leu Lys
        675                 680                 685

Thr Cys Asn Pro Ser Asp Ile Leu Gln Met Cys Ser Phe Leu Glu Gly
    690                 695                 700

Lys
705

<210> SEQ ID NO 17
<211> LENGTH: 517
<212> TYPE: PRT
<213> ORGANISM: Pisum sativum

<400> SEQUENCE: 17

Met Ala Lys Leu Leu Ala Leu Ser Leu Ser Phe Cys Phe Leu Leu Leu
1               5                   10                  15

Gly Gly Cys Phe Ala Leu Arg Glu Gln Pro Gln Gln Asn Glu Cys Gln
            20                  25                  30

Leu Glu Arg Leu Asp Ala Leu Glu Pro Asp Asn Arg Ile Glu Ser Glu
        35                  40                  45

Gly Gly Leu Ile Glu Thr Trp Asn Pro Asn Asn Lys Gln Phe Arg Cys
    50                  55                  60

Ala Gly Val Ala Leu Ser Arg Ala Thr Leu Gln Arg Asn Ala Leu Arg
65              70                  75                  80

Arg Pro Tyr Tyr Ser Asn Ala Pro Gln Glu Ile Phe Ile Gln Gln Gly
                85                  90                  95

Asn Gly Tyr Phe Gly Met Val Phe Pro Gly Cys Pro Glu Thr Phe Glu
            100                 105                 110

Glu Pro Gln Glu Ser Glu Gln Gly Glu Gly Arg Arg Tyr Arg Asp Arg
        115                 120                 125

His Gln Lys Val Asn Arg Phe Arg Glu Gly Asp Ile Ile Ala Val Pro
    130                 135                 140

Thr Gly Ile Val Phe Trp Met Tyr Asn Asp Gln Asp Thr Pro Val Ile
145                 150                 155                 160

Ala Val Ser Leu Thr Asp Ile Arg Ser Ser Asn Asn Gln Leu Asp Gln
                165                 170                 175

Met Pro Arg Arg Phe Tyr Leu Ala Gly Asn His Glu Gln Glu Phe Leu
            180                 185                 190

Gln Tyr Gln His Gln Gly Gly Lys Gln Glu Gln Glu Asn Glu Gly
        195                 200                 205

Asn Asn Ile Phe Ser Gly Phe Lys Arg Asp Tyr Leu Glu Asp Ala Phe
    210                 215                 220

Asn Val Asn Arg His Ile Val Asp Arg Leu Gln Gly Arg Asn Glu Asp
225                 230                 235                 240

Glu Glu Lys Gly Ala Ile Val Lys Val Lys Gly Gly Leu Ser Ile Ile
                245                 250                 255

Ser Pro Pro Glu Lys Gln Ala Arg His Gln Arg Gly Ser Arg Gln Glu
```

```
            260                 265                 270
Glu Asp Glu Asp Glu Lys Gln Pro Arg His Gln Arg Gly Ser Arg
        275                 280                 285
Gln Glu Glu Glu Asp Glu Asp Glu Glu Arg Gln Pro Arg His Gln
        290                 295                 300
Arg Arg Arg Gly Glu Glu Glu Glu Asp Lys Lys Glu Arg Gly Gly
305                 310                 315                 320
Ser Gln Lys Gly Lys Ser Arg Arg Gln Gly Asp Asn Gly Leu Glu Glu
                325                 330                 335
Thr Val Cys Thr Ala Lys Leu Arg Leu Asn Ile Gly Pro Ser Ser Ser
                340                 345                 350
Pro Asp Ile Tyr Asn Pro Glu Ala Gly Arg Ile Lys Thr Val Thr Ser
                355                 360                 365
Leu Asp Leu Pro Val Leu Arg Trp Leu Lys Leu Ser Ala Glu His Gly
                370                 375                 380
Ser Leu His Lys Asn Ala Met Phe Val Pro His Tyr Asn Leu Asn Ala
385                 390                 395                 400
Asn Ser Ile Ile Tyr Ala Leu Lys Gly Arg Ala Arg Leu Gln Val Val
                405                 410                 415
Asn Cys Asn Gly Asn Thr Val Phe Asp Gly Leu Glu Ala Gly Arg
                420                 425                 430
Ala Leu Thr Val Pro Gln Asn Tyr Ala Val Ala Lys Ser Leu Ser
                435                 440                 445
Asp Arg Phe Ser Tyr Val Ala Phe Lys Thr Asn Asp Arg Ala Gly Ile
        450                 455                 460
Ala Arg Leu Ala Gly Thr Ser Ser Val Ile Asn Asn Leu Pro Leu Asp
465                 470                 475                 480
Val Val Ala Ala Thr Phe Asn Leu Gln Arg Asn Glu Ala Arg Gln Leu
                485                 490                 495
Lys Ser Asn Asn Pro Phe Lys Phe Leu Val Pro Ala Arg Glu Ser Glu
                500                 505                 510
Asn Arg Ala Ser Ala
        515

<210> SEQ ID NO 18
<211> LENGTH: 5
<212> TYPE: PRT
<213> ORGANISM: Artificial Sequence
<220> FEATURE:
<223> OTHER INFORMATION: synthesized

<400> SEQUENCE: 18

Ile Ile Ser Ile Gly
1               5

<210> SEQ ID NO 19
<211> LENGTH: 6
<212> TYPE: PRT
<213> ORGANISM: Artificial Sequence
<220> FEATURE:
<223> OTHER INFORMATION: synthesized

<400> SEQUENCE: 19

Ile Ile Ser Ile Gly Arg
1               5

<210> SEQ ID NO 20
<211> LENGTH: 6
```

```
<212> TYPE: PRT
<213> ORGANISM: Artificial Sequence
<220> FEATURE:
<223> OTHER INFORMATION: synthesized

<400> SEQUENCE: 20

Val Phe Ile Lys Ala Ala
1               5

<210> SEQ ID NO 21
<211> LENGTH: 7
<212> TYPE: PRT
<213> ORGANISM: Artificial Sequence
<220> FEATURE:
<223> OTHER INFORMATION: synthesized

<400> SEQUENCE: 21

Val Phe Ile Lys Ala Ala Ala
1               5

<210> SEQ ID NO 22
<211> LENGTH: 5
<212> TYPE: PRT
<213> ORGANISM: Artificial Sequence
<220> FEATURE:
<223> OTHER INFORMATION: synthesized

<400> SEQUENCE: 22

Val Phe Ile Lys Ala
1               5
```